(12) United States Patent
Jang et al.

(10) Patent No.: US 11,706,975 B2
(45) Date of Patent: *Jul. 18, 2023

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY APPARATUS

(71) Applicant: SAMSUNG SDI CO., LTD., Yongin-si (KR)

(72) Inventors: Kipo Jang, Suwon-si (KR); Jun Seok Kim, Suwon-si (KR); Jinhyun Lui, Suwon-si (KR); Chang Ju Shin, Suwon-si (KR); Sujin Han, Suwon-si (KR); Youngkwon Kim, Suwon-si (KR); Eun Sun Yu, Suwon-si (KR); Sung-Hyun Jung, Suwon-si (KR); Ho Kuk Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 686 days.

This patent is subject to a terminal disclaimer.

(21) Appl. No.: 16/099,507

(22) PCT Filed: Jan. 18, 2017

(86) PCT No.: PCT/KR2017/000619
§ 371 (c)(1),
(2) Date: Nov. 7, 2018

(87) PCT Pub. No.: WO2018/004096
PCT Pub. Date: Jan. 4, 2018

(65) Prior Publication Data
US 2019/0165280 A1 May 30, 2019

(30) Foreign Application Priority Data
Jun. 29, 2016 (KR) .................. 10-2016-0081767

(51) Int. Cl.
*H01L 51/00* (2006.01)
*C07D 405/14* (2006.01)
(Continued)

(52) U.S. Cl.
CPC ........ *H01L 51/0067* (2013.01); *C07D 209/86* (2013.01); *C07D 251/24* (2013.01);
(Continued)

(58) Field of Classification Search
CPC .. C07D 209/86; C07D 251/24; C07D 307/91; C07D 333/76; C07D 405/14;
(Continued)

(56) References Cited

U.S. PATENT DOCUMENTS 6,229,012 B1 5/2001 Hu et al.
9,209,406 B2 12/2015 Mizutani et al.
(Continued)

FOREIGN PATENT DOCUMENTS

CN 102850329 A 1/2013
CN 103380508 A 10/2013
(Continued)

OTHER PUBLICATIONS

Organic Electronics, vol. 38, (2016), pp. 301-306. (Year: 2016).*
(Continued)

*Primary Examiner* — Dawn L Garrett
(74) *Attorney, Agent, or Firm* — Lee IP Law, P.C.

(57) ABSTRACT

Disclosed are a compound for an organic optoelectronic device represented by Chemical Formula 1, a composition for an organic optoelectronic device, an organic optoelectronic device including the same, and a display device. Details of Chemical Formula 1 are the same as defined in the specification.

16 Claims, 1 Drawing Sheet

(51) Int. Cl.
    *C07D 409/14*     (2006.01)
    *C09K 11/06*     (2006.01)
    *C07D 251/24*     (2006.01)
    *C07D 307/91*     (2006.01)
    *H01L 51/50*     (2006.01)
    *C07D 333/76*     (2006.01)
    *C07D 209/86*     (2006.01)
    *C09K 11/02*     (2006.01)

(52) U.S. Cl.
    CPC ......... *C07D 307/91* (2013.01); *C07D 333/76* (2013.01); *C07D 405/14* (2013.01); *C07D 409/14* (2013.01); *C09K 11/02* (2013.01); *C09K 11/06* (2013.01); *H01L 51/00* (2013.01); *H01L 51/0072* (2013.01); *H01L 51/0073* (2013.01); *H01L 51/0074* (2013.01); *H01L 51/50* (2013.01); *H01L 51/508* (2013.01); *C09K 2211/1018* (2013.01); *C09K 2211/1029* (2013.01); *C09K 2211/185* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/5384* (2013.01)

(58) Field of Classification Search
    CPC ...... C07D 409/14; C09K 11/02; C09K 11/06; C09K 2211/1018; C09K 2211/1029; C09K 2211/185; H01L 2251/5384; H01L 51/00; H01L 51/0067; H01L 51/0072; H01L 51/0073; H01L 51/0074; H01L 51/50; H01L 51/5016; H01L 51/5056; H01L 51/5072; H01L 51/5088; H01L 51/5092; H01L 51/5096
    See application file for complete search history.

(56) References Cited

U.S. PATENT DOCUMENTS

| | | | |
|---|---|---|---|
| 9,893,290 B2 * | 2/2018 | Min | H01L 51/0072 |
| 11,158,817 B2 | 10/2021 | Lui et al. | |
| 11,264,574 B2 | 3/2022 | Jang et al. | |
| 2004/0164292 A1 | 8/2004 | Tung | |
| 2006/0046342 A1 | 3/2006 | Karg et al. | |
| 2007/0141387 A1 | 6/2007 | Nakano et al. | |
| 2013/0264560 A1 | 10/2013 | Dobbs et al. | |
| 2014/0001456 A1 | 1/2014 | Mizutani et al. | |
| 2014/0361258 A1 | 12/2014 | Hwang et al. | |
| 2015/0028320 A1 | 1/2015 | Kinoshita et al. | |
| 2015/0171336 A1 | 6/2015 | Park et al. | |
| 2015/0171340 A1 | 6/2015 | Lee et al. | |
| 2015/0207082 A1 | 7/2015 | Dyatkin | |
| 2015/0349268 A1 | 12/2015 | Zeng et al. | |
| 2016/0028021 A1 | 1/2016 | Zeng | |
| 2016/0329502 A1 | 11/2016 | Dyatkin et al. | |
| 2017/0025618 A1 | 1/2017 | Zheng et al. | |
| 2017/0117488 A1 | 4/2017 | Ahn | |
| 2018/0033975 A1 | 2/2018 | Kim | |
| 2018/0337341 A1 | 11/2018 | Heo | |

FOREIGN PATENT DOCUMENTS

| | | | |
|---|---|---|---|
| CN | 104271703 A | 1/2015 |
| CN | 103232843 B | 2/2015 |
| CN | 104812750 A | 7/2015 |
| CN | 104885247 A | 9/2015 |
| CN | 104995187 A | 10/2015 |
| CN | 105153130 A | 12/2015 |
| CN | 105315219 A | 2/2016 |
| CN | 105315265 A | 2/2016 |
| CN | 105359290 A | 2/2016 |
| CN | 105473684 A | 4/2016 |
| CN | 105601612 A | 5/2016 |
| CN | 107093677 A | 8/2017 |
| CN | 107325090 A | 11/2017 |
| CN | 108290854 A | 7/2018 |
| EP | 2 966 706 A2 | 1/2016 |
| EP | 3 268 449 A1 | 2/2016 |
| JP | 2014/040423 A | 3/2014 |
| JP | 2014-123687 A | 7/2014 |
| JP | 5541167 B2 | 7/2014 |
| JP | 2014-157947 A | 8/2014 |
| JP | 5847420 B2 | 1/2016 |
| JP | 2016/019002 A | 2/2016 |
| JP | 2016-506414 A | 3/2016 |
| JP | 2016-525081 A | 8/2016 |
| JP | 2018-514081 A | 5/2018 |
| KR | 10-2011-0096453 | 8/2011 |
| KR | 10-2010-0118690 | 11/2011 |
| KR | 10-2012-0129733 A | 11/2012 |
| KR | 10-2013-0036048 A | 4/2013 |
| KR | 10-2013-0061371 | 6/2013 |
| KR | 10-2014-0005804 A | 1/2014 |
| KR | 10-2014-0010133 | 1/2014 |
| KR | 10-1423067 B1 | 7/2014 |
| KR | 10-2014-0144550 A | 12/2014 |
| KR | 10-2015-0036736 | 4/2015 |
| KR | 10-2015-0042335 A | 4/2015 |
| KR | 10-2015-0070860 A | 6/2015 |
| KR | 10-1542714 B1 | 7/2015 |
| KR | 10-2015-0116776 A | 10/2015 |
| KR | 10-2015-0129282 A | 11/2015 |
| KR | 10-2015-0131998 A | 11/2015 |
| KR | 10-2015-0136942 | 12/2015 |
| KR | 10-2016-0006633 A | 1/2016 |
| KR | 10-1593465 B1 | 2/2016 |
| KR | 10-2016-0028524 A | 3/2016 |
| KR | 10-2016-0034528 A | 3/2016 |
| KR | 2016-37909 | 3/2016 |
| KR | 10-2016-0038006 A | 4/2016 |
| KR | 10-2016-0055556 A | 5/2016 |
| KR | 10-2016-0080090 A | 7/2016 |
| KR | 10-2016-0110078 A | 9/2016 |
| KR | 10-2017-0022865 | 3/2017 |
| KR | 10-2017-0089599 A | 8/2017 |
| KR | 10-2017-0116992 A | 10/2017 |
| KR | 10-2017-0141144 A | 12/2017 |
| TW | 201609712 A | 3/2016 |
| TW | 201619152 A | 6/2016 |
| WO | WO 2010/044342 A1 | 4/2010 |
| WO | WO 2013/077352 A1 | 5/2013 |
| WO | WO 2014/054912 A1 | 4/2014 |
| WO | WO 2014208755 A1 | 12/2014 |
| WO | WO 2015/000549 A1 | 1/2015 |
| WO | WO 2015/156587 A1 | 10/2015 |
| WO | WO 2015/160224 A1 | 10/2015 |
| WO | WO 2016/076384 A1 | 5/2016 |
| WO | WO 2016084962 A1 | 6/2016 |
| WO | WO 2016 148390 A1 | 9/2016 |
| WO | WO 2016/172414 A1 | 10/2016 |
| WO | WO 2017/016630 A1 | 2/2017 |
| WO | WO 2017/146466 A1 | 8/2017 |
| WO | WO 2017/171420 A1 | 10/2017 |
| WO | WO 2018/016742 A1 | 1/2018 |
| WO | WO 2018/021663 A1 | 2/2018 |
| WO | WO 2018/062659 A1 | 4/2018 |
| WO | WO 2018/093026 A1 | 5/2018 |
| WO | WO 2018/097461 A1 | 5/2018 |
| WO | WO 2018/128255 A1 | 7/2018 |

OTHER PUBLICATIONS

Office action received in copending related U.S. Appl. No. 16/097,657.
International Search Report dated Apr. 24, 2017.
European Search Report dated Dec. 19, 2019, Application No. 17820373.3.
European Search Report dated Jan. 8, 2020, Application No. 17820372.5.
U.S. Appl. No. 16/097,657, filed Oct. 30, 2018.
U.S. Appl. No. 16/099,523, filed Nov. 7, 2018.

(56) References Cited

OTHER PUBLICATIONS

U.S. Office Action dated Jan. 13, 2021 from Co-pending U.S. Appl. No. 16/468,779.
Extended European Search Report dated Feb. 17, 2020, European Patent Application No. 17827792.7.
Extended European Search Report dated Feb. 28, 2020, European Patent Application No. 17834608.6.
U.S. Appl. No. 16/468,779, filed Jun. 12, 2019.
Japanese Office action dated Sep. 29, 2020, received in Japanese Application No. 2018-568699;.
Japanese Notice of Allowance dated Oct. 6, 2020, received in Japanese Application No. 2019-503551.
U.S. Appl. No. 16/321,228, filed Jan. 28, 2019.
U.S. Office Action received in Co Pending U.S. Appl. No. 16/321,228 dated Jun. 25, 2021.
U.S. Office action received in co pending U.S. Appl. No. 16/099,523, dated Apr. 19, 2021.
European Office action dated Mar. 25, 2021.
Office Action received in Co-pending U.S. Appl. No. 16/099,523 dated Oct. 7, 2021.
European Office action received in copending Appln. No. EP17834608.6 dated Jan. 21, 2022.
European Office action received in copending Appln. No. EP 17820372.5 dated Dec. 17, 2021.
Machine translation of KR 20170089599 A (publication date Aug. 2017). (Year: 2017).
U.S. Office action received in co pending U.S. Appl. No. 16/099,523 dated May 20, 2022.
U.S. Office action received in co-pending U.S. Appl. No. 16/099,523, dated Nov. 14, 2022.

* cited by examiner

COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY APPARATUS

CROSS REFERENCE TO RELATED APPLICATIONS

This is the U.S. national phase application based on PCT Application No. PCT/KR 2017/000619, filed Jan. 18, 2017, which is based on Korean Patent Application No. 10-2016-0081767, filed Jun. 29, 2016, the entire contents of all of which are hereby incorporated by reference.

TECHNICAL FIELD

A compound for an organic optoelectronic device, a composition for an organic optoelectronic device, an organic optoelectronic device, and a display device are disclosed.

BACKGROUND ART

An organic optoelectronic device is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of an organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light-emitting layer and optionally an auxiliary layer, and the auxiliary layer may be, for example at least one selected from a hole injection layer, a hole transport layer, an electron blocking layer, an electron transport layer, an electron injection layer, and a hole blocking layer for improving efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides a composition for an organic optoelectronic device capable of realizing an organic optoelectronic device having high efficiency and a long life-span.

Another embodiment provides a composition for an organic optoelectronic device including the compound for an organic optoelectronic device.

Yet another embodiment provides an organic optoelectronic device including the compound.

Still another embodiment provides a display device including the organic optoelectronic device.

Technical Solution

According to an embodiment, a compound represented by Chemical Formula 1 for an organic optoelectronic device is provided.

[Chemical Formula 1]

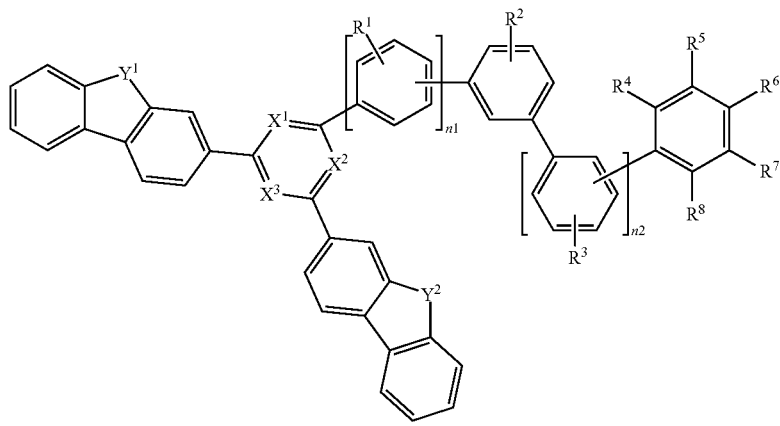

In Chemical Formula 1,
$X^1$ to $X^3$ are independently N or $CR^a$,
at least two of $X^1$ to $X^3$ are N,
$Y^1$ and $Y^2$ are independently O or S,
n1 and n2 are independently an integer of 0 or 1,
$R^a$ and $R^1$ to $R^8$ are independently hydrogen, deuterium, a cyano group, a nitro group, a substituted or unsubstituted C1 to C10 alkyl group, a substituted or unsubstituted C6 to C30 aryl group, a substituted or unsubstituted C2 to C30 heterocyclic group, or a combination thereof, and the "substituted" refers to replacement of at least one hydrogen by deuterium, a C1 to C20 alkyl group, a C6 to C30 aryl group, or a C2 to C30 heteroaryl group.

According to another embodiment, a composition for an organic optoelectronic device includes the first compound for an organic optoelectronic device; and a second compound for an organic optoelectronic device represented by Chemical Formula 2.

[Chemical Formula 2]

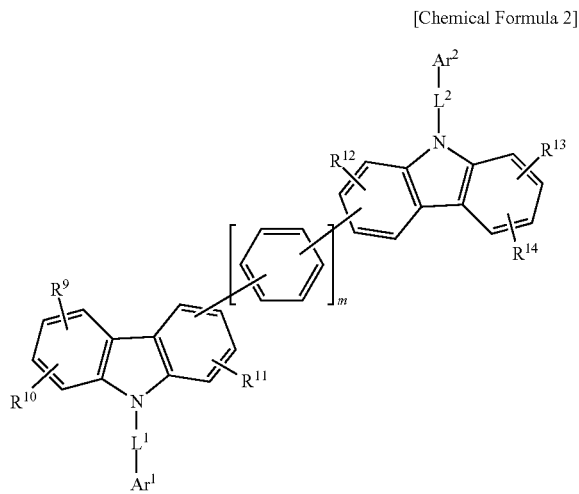

In Chemical Formula 2,

L$^1$ and L$^2$ are independently a single bond, a substituted or unsubstituted C6 to C30 arylene group, a substituted or unsubstituted C2 to C30 heteroarylene group, or a combination thereof, Ar$^1$ and Ar$^2$ are independently a substituted or unsubstituted C6 to C30 aryl group, a substituted or unsubstituted C2 to C30 heterocyclic group, or a combination thereof, R$^9$ to R$^{14}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is an integer of 0 to 2;

wherein the "substituted" refers to replacement of at least one hydrogen by deuterium, a C1 to C4 alkyl group, a C6 to C18 aryl group, or a C2 to C30 heteroaryl group.

According to another embodiment, an organic optoelectronic device includes an anode and a cathode facing each other and at least one organic layer disposed between the anode and the cathode wherein the organic layer includes the compound for an organic optoelectronic device, or the composition for an organic optoelectronic device.

According to another embodiment, a display device including the organic optoelectronic device is provided.

Advantageous Effects

An organic optoelectronic device having high efficiency and a long life-span may be realized.

DESCRIPTION OF SYMBOLS

Figure 1:
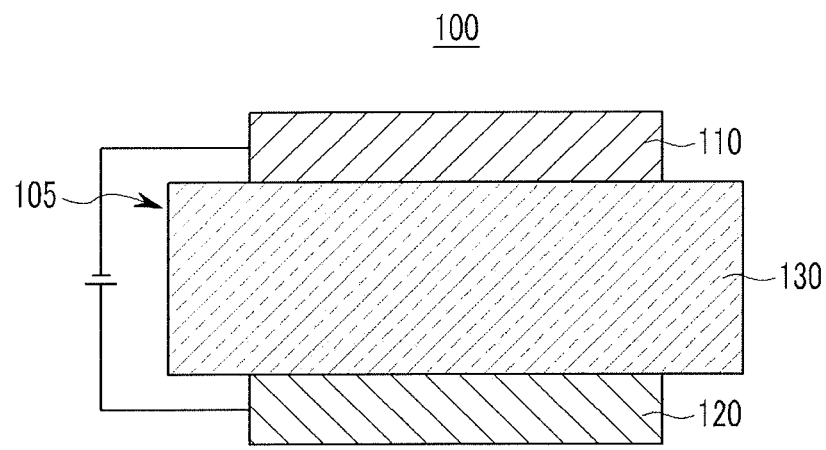
FIGS. 1 and 2 are cross-sectional views showing organic light emitting diodes according embodiments.

100, 200: organic light emitting diode
105: organic layer
110: cathode
120: anode
130: light-emitting layer
140: hole auxiliary layer

MODE FOR INVENTION

Hereinafter, embodiments of the present invention are described in detail. However, these embodiments are exemplary, the present invention is not limited thereto and the present invention is defined by the scope of claims.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a fluoro group, a C1 to C10 trifluoroalkyl group, a cyano group, or a combination thereof.

In one example of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In specific example of the present invention, the "substituted" refers to replacement of at least one hydrogen of a substituent or a compound by deuterium, a C1 to C20 alkyl group, a C6 to C30 aryl group, or a C2 to C30 heteroaryl group. In specific example of the present invention, the "substituted" refers to replacement of at least one hydrogen by deuterium, C1 to C20 alkyl group, a C6 to C30 aryl group, a substituted or unsubstituted pyridinyl group, a substituted or unsubstituted quinolinyl group, a substituted or unsubstituted isoquinolinyl group, a substituted or unsubstituted dibenzofuranyl group, or a substituted or unsubstituted dibenzothiophenyl group. In specific example of the present invention, the "substituted" refers to replacement of at least one hydrogen by deuterium, C1 to C5 alkyl group, a C6 to C18 aryl group, a pyridinyl group, a quinolinyl group, a isoquinolinyl group, a dibenzofuranyl group, or a dibenzothiophenyl group. In another specific example of the present invention, the "substituted" refers to replacement of at least one hydrogen by deuterium, C1 to C5 alkyl group or a C6 to C12 aryl group.

As used herein, when a definition is not otherwise provided, "hetero" refers to one including one to three heteroatoms selected from N, O, S, P, and Si, and remaining carbons in one functional group.

As used herein, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, an "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

As used herein, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, a "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied, and that a hole formed in the anode may be easily injected into a light-emitting layer, and a hole formed in a light-emitting layer may be easily transported into an anode and transported in a light-emitting layer due to conductive characteristics according to a highest occupied molecular orbital (HOMO) level.

In addition, electron characteristics refer to an ability to accept an electron when an electric field is applied and that an electron formed in a cathode may be easily injected into a light-emitting layer, and an electron formed in a light-emitting layer may be easily transported into a cathode and transported in a light-emitting layer due to conductive characteristics according to a lowest unoccupied molecular orbital (LUMO) level. For example, ET core means a core which has electron characteristics.

Hereinafter, a compound for an organic optoelectronic device according to an embodiment is described.

A compound for an organic optoelectronic device according to an embodiment is represented by Chemical Formula 1.

[Chemical Formula 1]

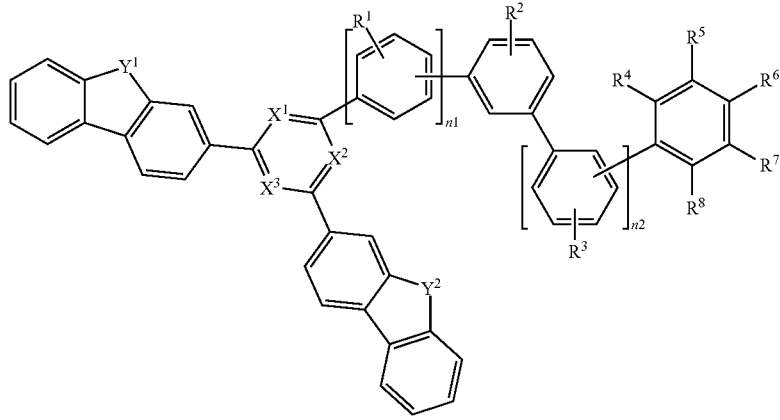

In Chemical Formula 1, $X^1$ to $X^3$ are independently N or $CR^a$, at least two of $X^1$ to $X^3$ are N, $Y^1$ and $Y^2$ are independently O or S, n1 and n2 are independently an integer of 0 or 1, $R^a$ and $R^1$ to $R^8$ are independently hydrogen, deuterium, a cyano group, a nitro group, a substituted or unsubstituted C1 to C10 alkyl group, a substituted or unsubstituted C6 to C30 aryl group, a substituted or unsubstituted C2 to C30 heterocyclic group, or a combination thereof, and the "substituted" refers to replacement of at least one hydrogen by deuterium, a C1 to C20 alkyl group, a C6 to C30 aryl group, or a C2 to C30 heteroaryl group.

A compound for an organic optoelectronic device according to the present invention includes an ET core including an N-containing 6-membered ring that includes a substituent directly linked with at least two dibenzofuran or dibenzothiophene at a position No. 3 without a linking group, and thereby a LUMO energy band is effectively expanded, planarity of a molecular structure is increased, and the compound may become a structure capable of accepting electrons when an electric field is applied, and accordingly an organic optoelectronic device including the compound for an organic optoelectronic device may exhibit a lowered driving voltage. Such a LUMO expansion and ring fusion increase stability for electrons of the ET core and life-span of a device is effectively improved.

In addition, interactions with adjacent molecules may be suppressed and crystallization is decreased due to steric hindrance characteristics by at least one meta-bound arylene and accordingly efficiency and life-span characteristics of an organic optoelectronic device including the compound for an organic optoelectronic device may be improved.

A kinked moiety such as the meta-bound arylene increases a glass transition temperature (Tg) of a compound and stability of a compound may be increased and degradation may be suppressed when it is applied to a device.

In an example embodiment of the present invention, an ET core consisting of $X^1$ to $X^3$ may be pyrimidine or triazine and may be for example represented by Chemical Formula 1-I, Chemical Formula 1-II, or Chemical Formula 1-III. More specifically, it may be represented by Chemical Formula 1-I or Chemical Formula 1-II.

[Chemical Formula 1-I]

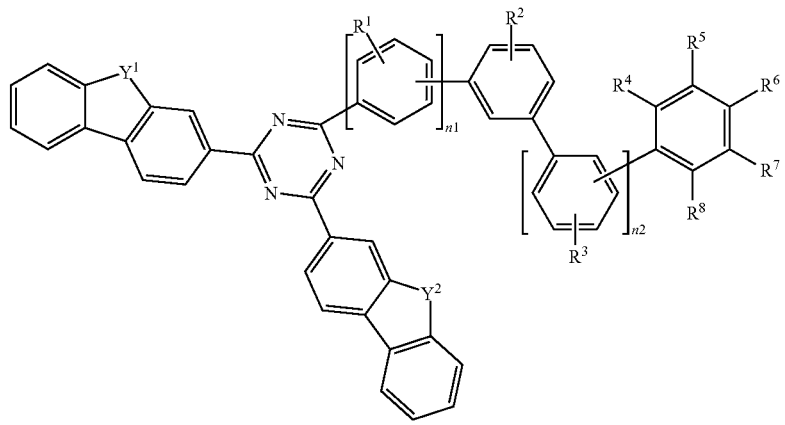

[Chemical Formula 1-II]

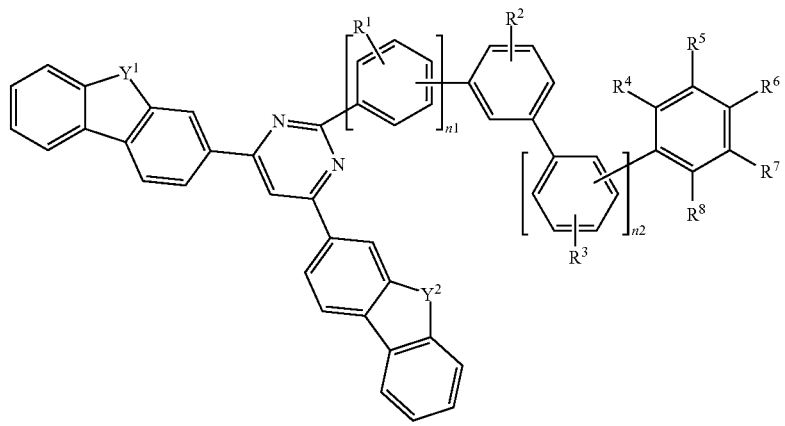

[Chemical Formula 1-III]

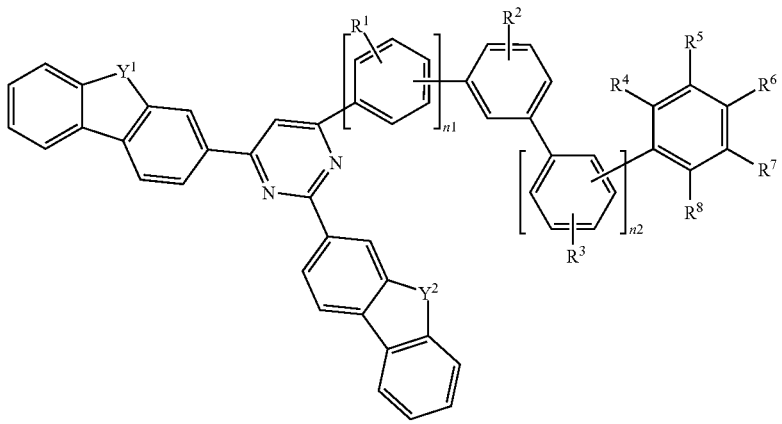

In Chemical Formula 1-I, Chemical Formula 1-II, and Chemical Formula 1-III, $Y^1$ and $Y^2$, n1 and n2 and $R^1$ to $R^8$ are the same as described above.

In an example embodiment of the present invention, $R^1$ to $R^8$ may independently be hydrogen, or a substituted or unsubstituted C6 to C30 aryl group, and specifically hydrogen, a substituted or unsubstituted phenyl group, a substituted or unsubstituted biphenyl group, a substituted or unsubstituted naphthyl group, a substituted or unsubstituted p-terphenyl group, a substituted or unsubstituted m-terphenyl group, a substituted or unsubstituted o-terphenyl group, a substituted or unsubstituted anthracenyl group, a substituted or unsubstituted phenanthrenyl group, a substituted or unsubstituted triphenylenyl group, or a substituted or unsubstituted fluorenyl group, and more specifically hydrogen, a phenyl group, a biphenyl group, a terphenyl group, or a naphthyl group.

For example, $R^1$ to $R^3$ may independently be hydrogen, deuterium, a phenyl group, a biphenyl group, or a naphthyl group.

In one example of the present invention, one of $R^4$ to $R^8$ may be deuterium, a phenyl group, a biphenyl group, or a terphenyl group and the rest is hydrogen.

In one example of the present invention, one of $R^5$ and $R^7$ or all of $R^5$ and $R^7$ may be deuterium, hydrogen, a phenyl group, a biphenyl group, or a terphenyl group, and all $R^4$, $R^6$, and $R^8$ may be hydrogen.

For example, $R^1$ may be hydrogen, or a phenyl group, all $R^2$ and $R^3$ may be hydrogen, and all $R^4$ to $R^8$ may be hydrogen or one of $R^4$ to $R^8$ may be a phenyl group, a biphenyl group, or a terphenyl group and the rest may be hydrogen.

In one example of the present invention, $R^1$ may be a phenyl group.

Chemical Formula 1 may be for example represented by Chemical Formula 1A, Chemical Formula 1B, or Chemical Formula 1C.

[Chemical Formula 1A]

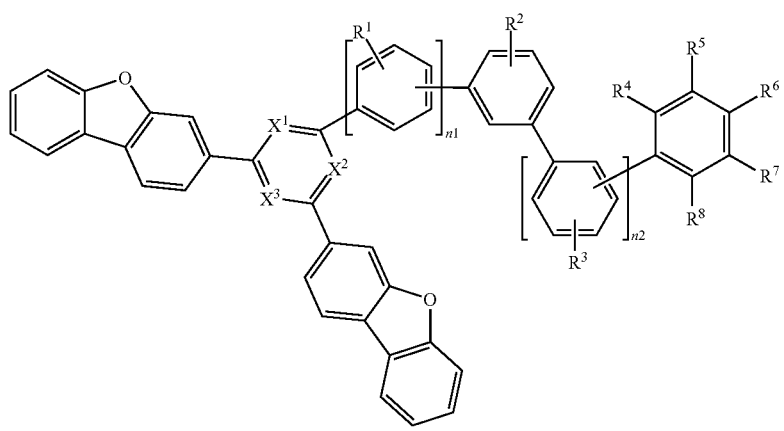

[Chemical Formula 1B]

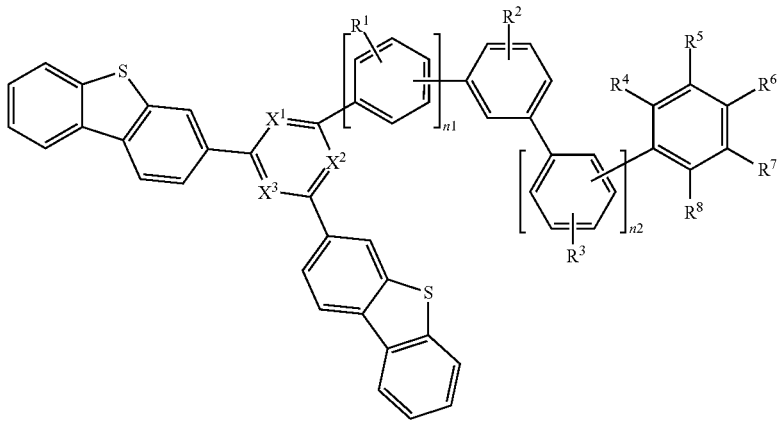

[Chemical Formula 1C]

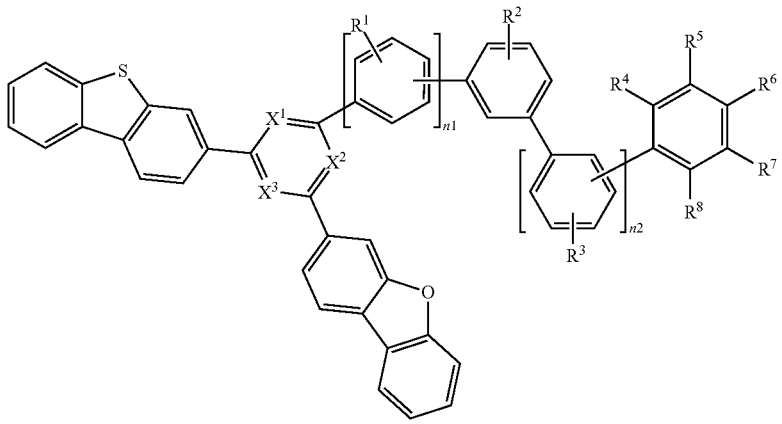

In Chemical Formula 1A, Chemical Formula 1B, and Chemical Formula 1C, n and n2, $R^1$ to $R^8$ are the same as above, and $X^1$ to $X^3$ are independently N or CH provided that at least two of $X^1$ to $X^3$ are N.

As shown in Chemical Formulae 1A to 1C, when the N-containing 6-membered ring includes a substituent directly linked at a position No. 3 of a dibenzofuranyl group and/or a dibenzothiophenyl group without a linking group, an optimal effect in terms of a driving voltage decrease and a life-span increase may be obtained by positioning LUMO phore on one plane and thus maximizing an expansion effect. However, when the dibenzofuran and/or the dibenzothiophene is linked with the N-containing 6-membered ring at not the position No. 3 but the other positions or through an arylene linker and the like therebetween, an effect of the driving voltage decrease through the LUMO expansion and a stability increase through a fusion of rings may be reduced.

In an example embodiment of the present invention, Chemical Formula 1 may be represented by Chemical Formula 1A, or Chemical Formula 1B, for example Chemical Formula 1A.

In an example embodiment of the present invention, both of n1 and n2 are 0 or n1=1, n2=0; or n1=0, n2=1, and Chemical Formula 1 has a structure including a meta-bonded arylene and may be for example represented by Chemical Formula 1-1 or Chemical Formula 1-2 and more specifically represented by Chemical Formula 1-1.

[Chemical Formula 1-1]

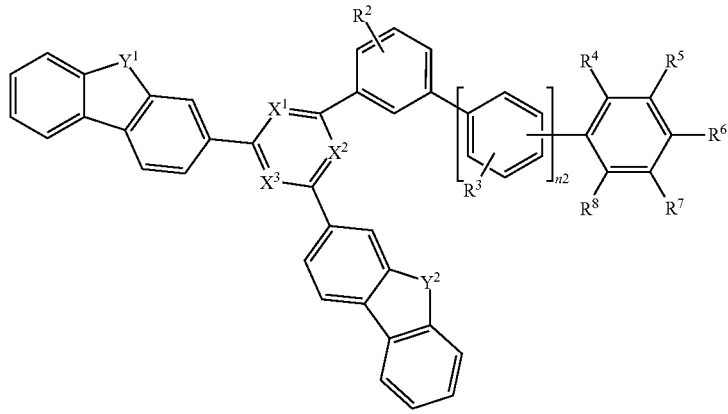

[Chemical Formula 1-2]

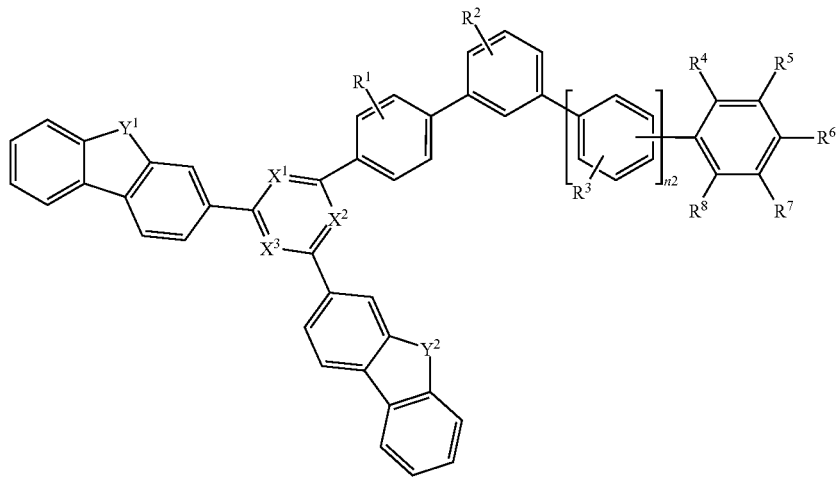

In Chemical Formulae 1-1 to 1-2, $X^1$ to $X^3$, $Y^1$ and $Y^2$, n2, and $R^1$ to $R^8$ are the same as described above.

Particularly, $R^2$ of Chemical Formulae 1-1 and 1-2 may be a substituted or unsubstituted C1 to C10 alkyl group, a substituted or unsubstituted C6 to C30 aryl group, or a substituted or unsubstituted C2 to C30 heterocyclic group, and more specifically $R^2$ may be substituted in a meta position, which may be represented by Chemical Formula 1-1a or Chemical Formula 1-2a. Herein, $R^2$-substituted phenylene may include a kinked terphenyl group.

[Chemical Formula 1-1a]

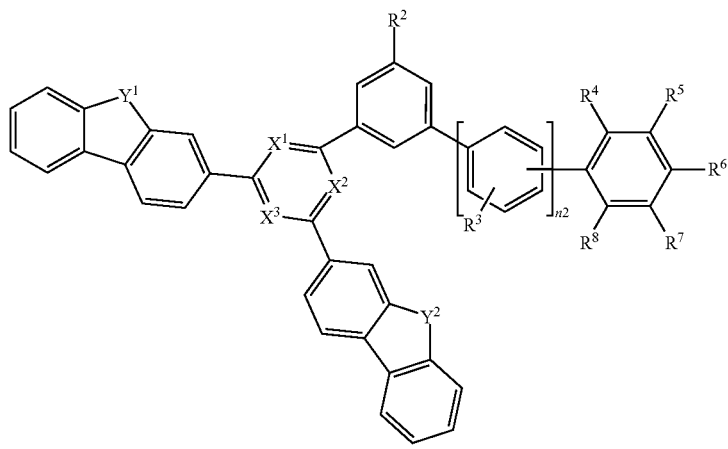

-continued

[Chemical Formula 1-2a]

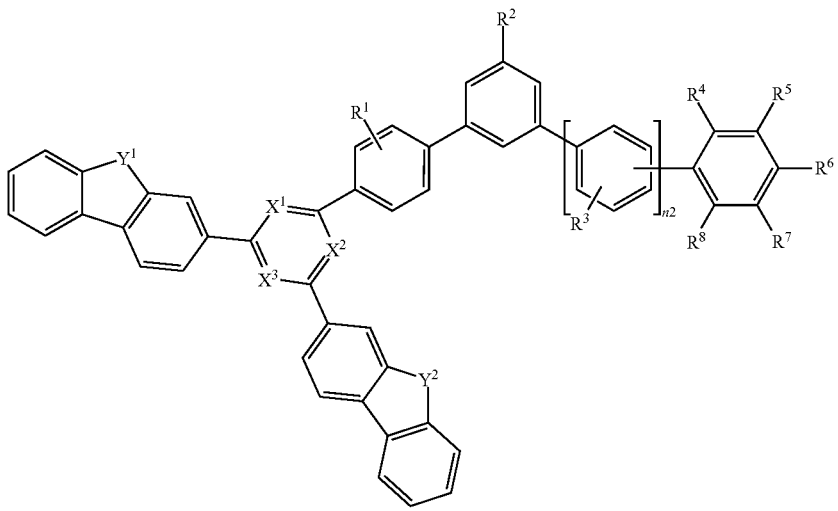

In an example embodiment of the present invention, $R^2$ may be a substituted or unsubstituted C1 to C4 alkyl group or a substituted or unsubstituted C6 to C30 aryl group, for example, a phenyl group, a biphenyl group, a terphenyl group, or a naphthyl group, and more specifically a substituted or unsubstituted phenyl group.

When the kinked terphenyl group is included, a glass transition temperature (Tg) may be increased effectively, and a low molecular weight compound having a high glass transition temperature (Tg) may be designed and thereby thermal characteristics may be ensured and stability and the like may be ensured.

The glass transition temperature (Tg) may have a relation with thermal stability of a compound and a device including the same. That is, when a compound for an organic optoelectronic device having a high glass transition temperature (Tg) is applied to an organic light emitting diode in a form of a thin film, degradation by temperature may be prevented and an organic compound and life-span characteristics of a device may be ensured in subsequent processes after deposition of the compound for an organic optoelectronic device.

In Chemical Formulae 1-1 and 1-2, a linking group represented by

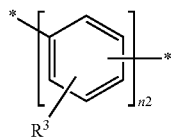

may be linked by a meta bond or a para bond.

The compound for an organic optoelectronic device represented by Chemical Formula 1 may be for example selected from compounds of Group 1, but is not limited thereto.

[Group 1]

[A-1]

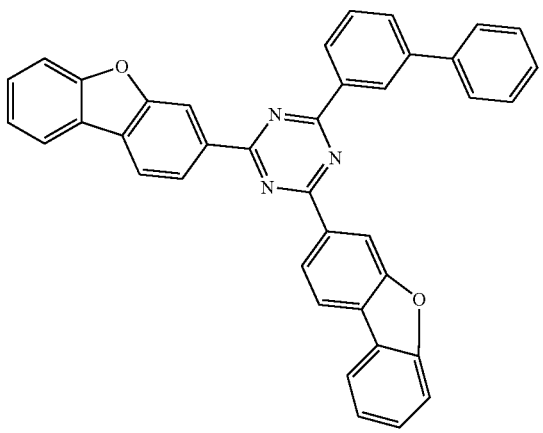

[A-2]

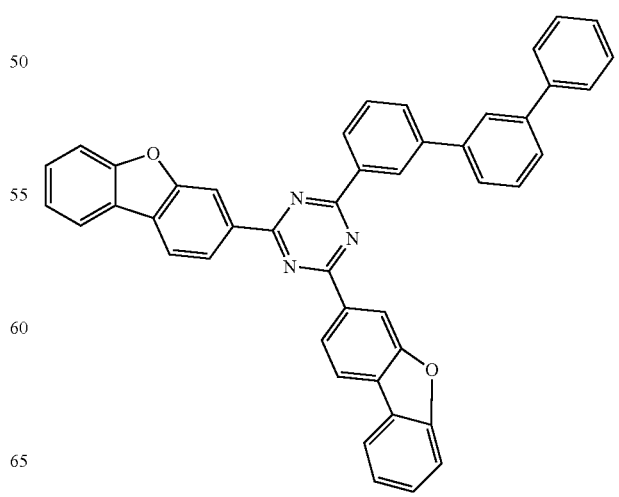

[A-3]
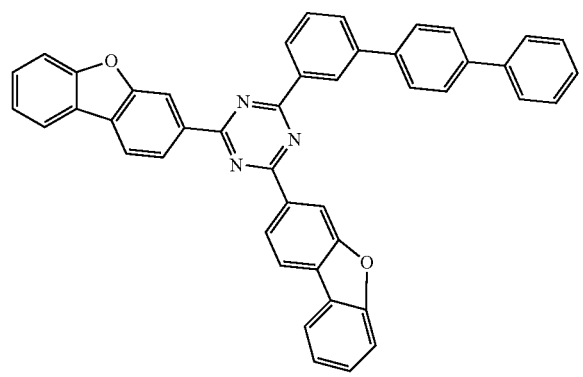
[A-4]
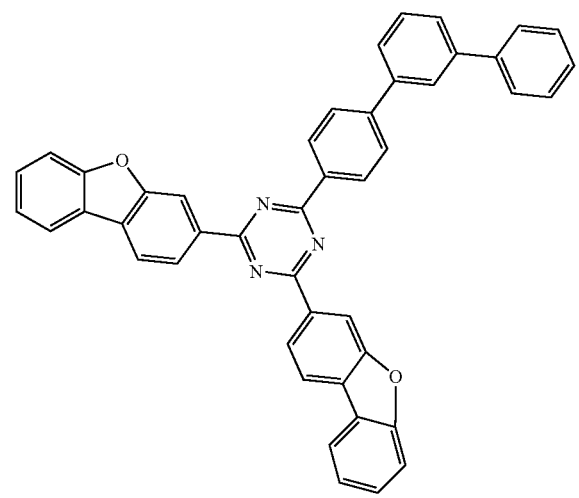
[A-5]
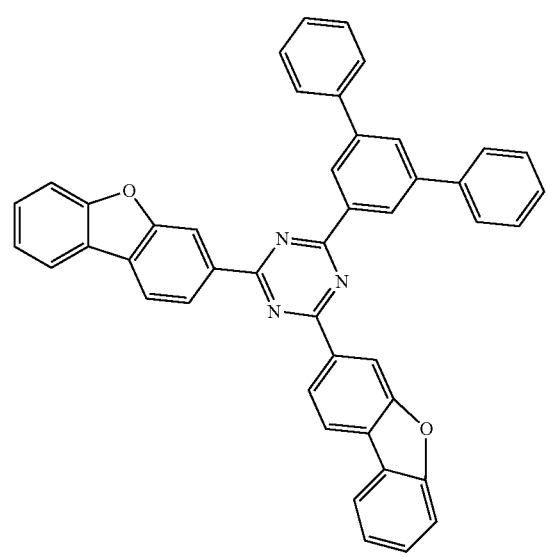
[A-6]
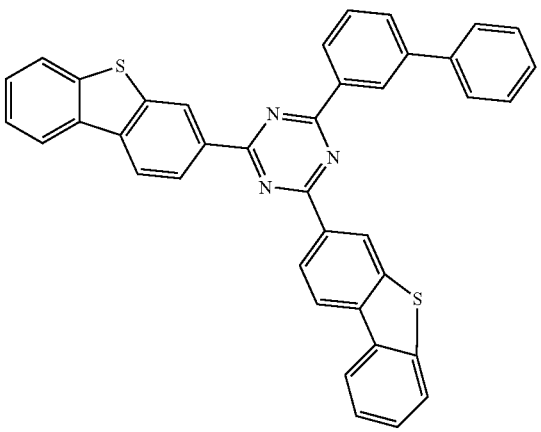
[A-7]
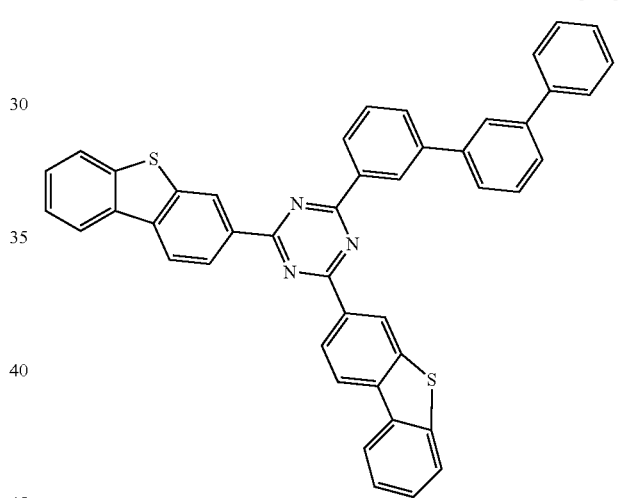
[A-8]
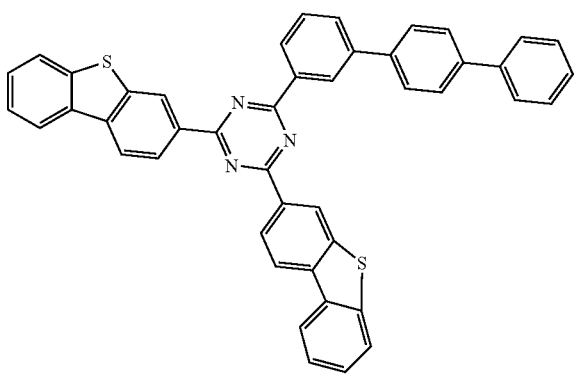

-continued
[A-9]
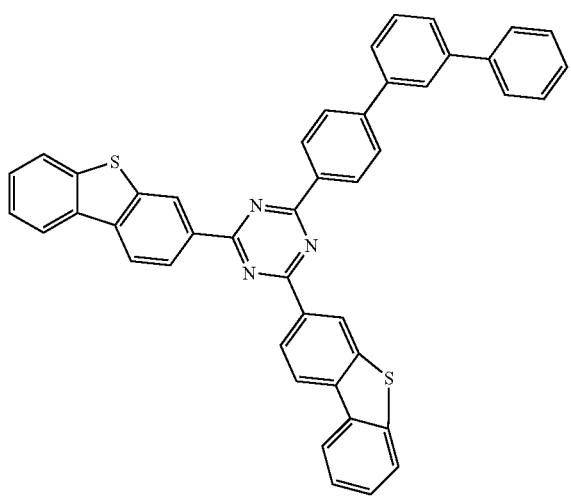
[A-12]
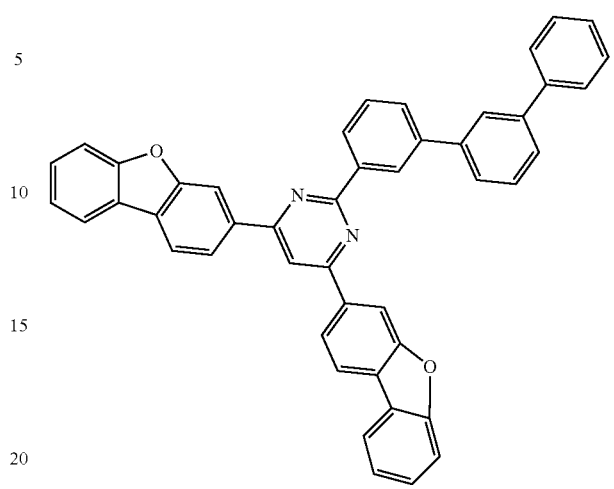
[A-10]
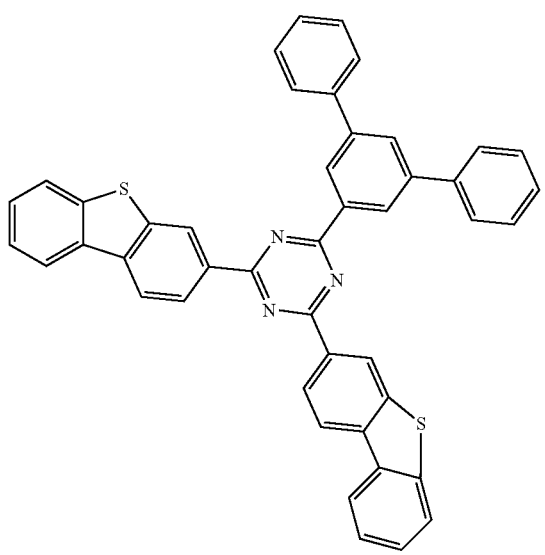
[A-13]
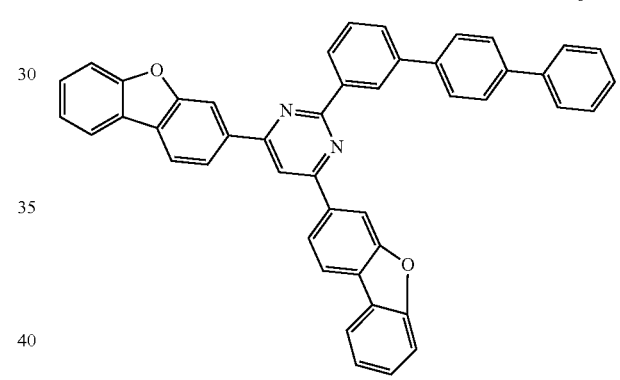
[A-11]
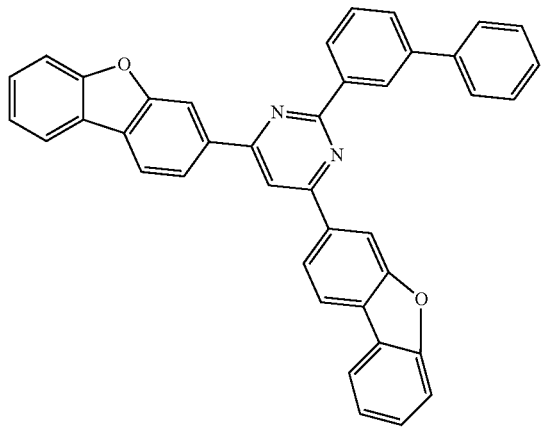
[A-14]
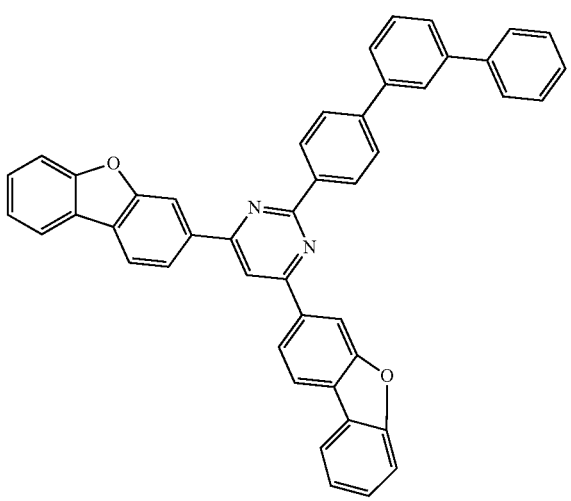

[A-15]

[A-16]

[A-17]

[A-18]

[A-19]

[A-20]

[A-21]
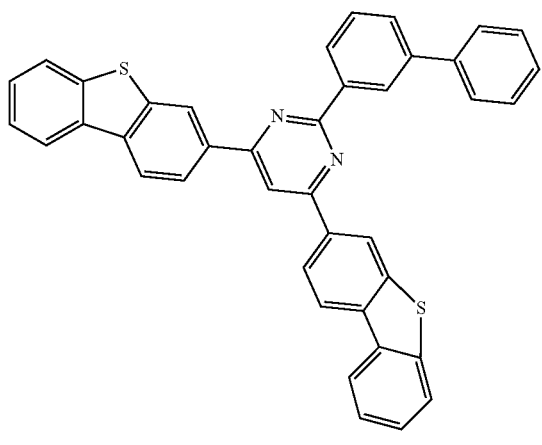
[A-24]
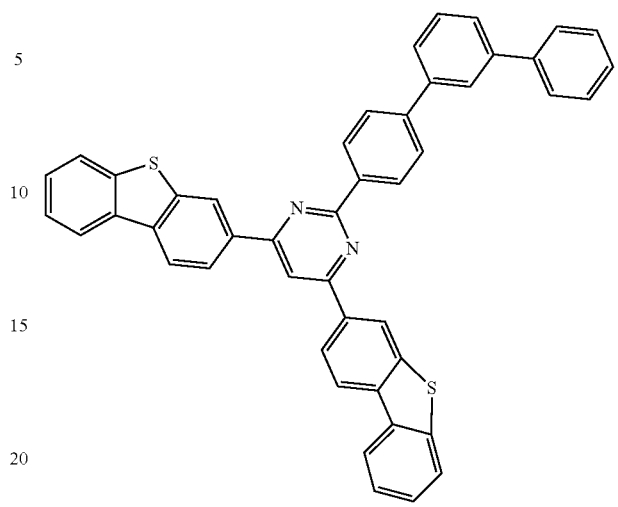
[A-22]
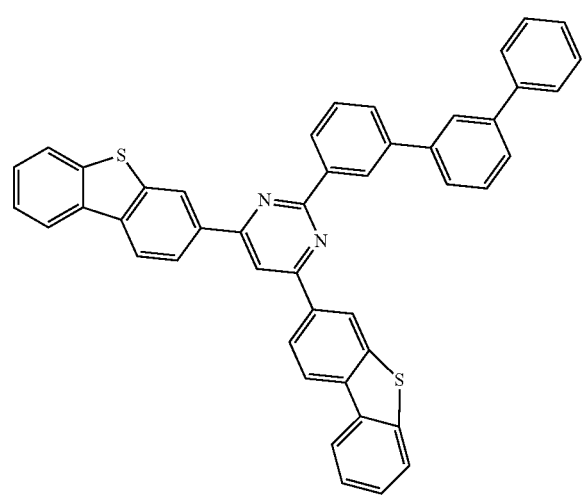
[A-25]
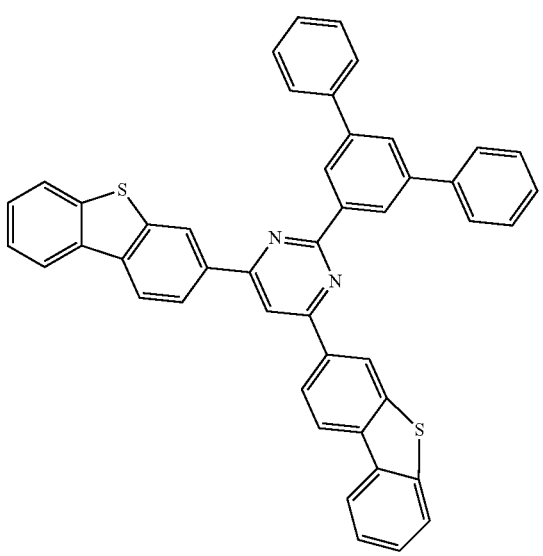
[A-23]
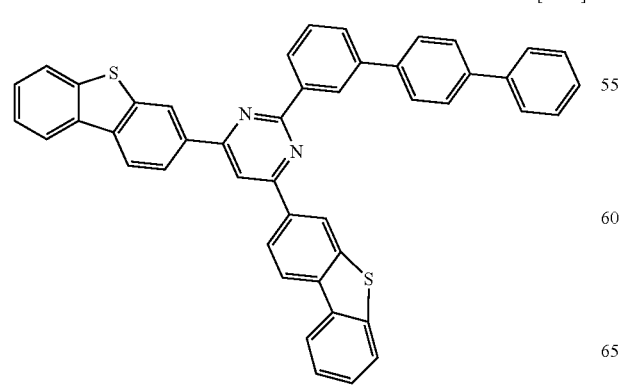
[A-26]
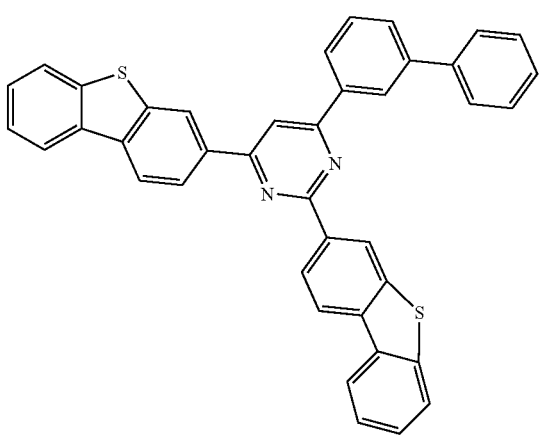

[A-27]

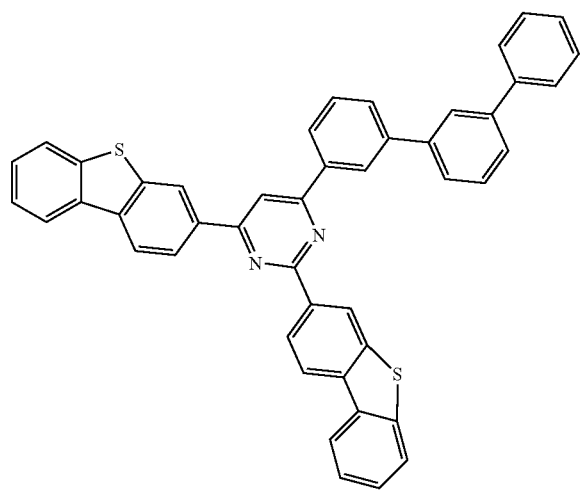

[A-30]

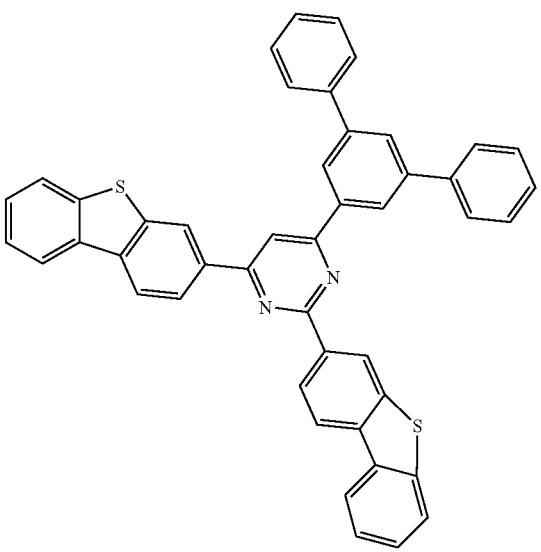

[A-28]

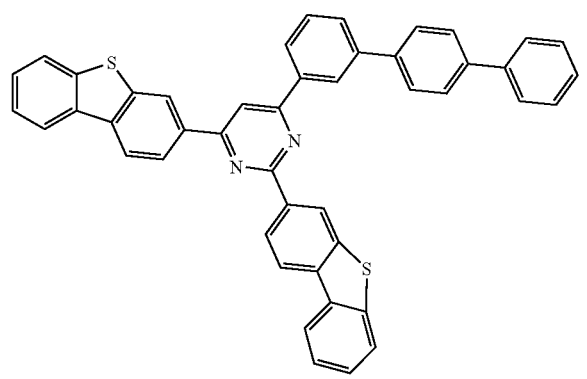

[A-29]

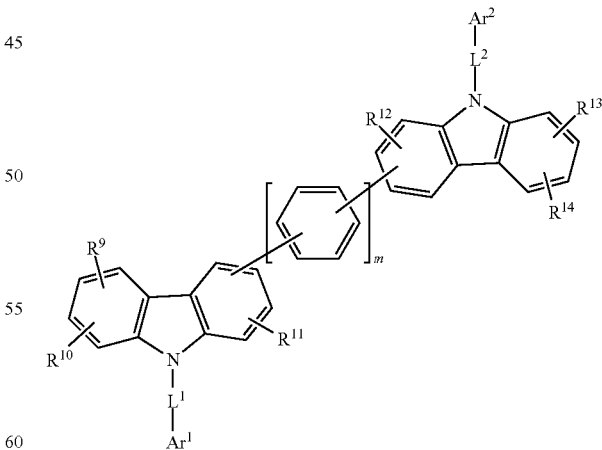

The first compound for an organic optoelectronic device may be applied to an organic optoelectronic device alone or with other compounds for an organic optoelectronic device. When the compound for an organic optoelectronic device is used with other compounds for an organic optoelectronic device, they may be applied in a form of a composition.

Hereinafter, one example of a composition for an organic optoelectronic device including the first compound for an organic optoelectronic device is described.

A composition for an organic optoelectronic device according to another embodiment of the present invention includes the first compound for an organic optoelectronic device; and a second compound for an organic optoelectronic device represented by Chemical Formula 2.

[Chemical Formula 2]

In Chemical Formula 2, $L^1$ and $L^2$ are independently a single bond, a substituted or unsubstituted C6 to C30 arylene group, a substituted or unsubstituted C2 to C30 heteroarylene group, or a combination thereof, Ar¹ and Ar² are independently a substituted or unsubstituted C6 to C30 aryl group, a substituted or unsubstituted C2 to C30 heterocyclic group, or a combination thereof, R⁹ to R¹⁴ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is an integer of 0 to 2;

wherein the "substituted" refers to replacement of at least one hydrogen by deuterium, a C1 to C4 alkyl group, a C6 to C18 aryl group, or a C2 to C30 heteroaryl group.

In an example embodiment of the present invention, L¹ and L² of Chemical Formula 2 may independently be a single bond, or a substituted or unsubstituted C6 to C18 arylene group.

In an example embodiment of the present invention, Ar¹ and Ar² of Chemical Formula 2 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted triazinyl group, a substituted or unsubstituted quinolinyl group, a substituted or unsubstituted isoquinolinyl group, a substituted or unsubstituted carbazolyl group, a substituted or unsubstituted fluorenyl group, or a combination thereof.

In an example embodiment of the present invention, Ar¹ and Ar² of Chemical Formula 2 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted quinolinyl group, a substituted or unsubstituted isoquinolinyl group, a substituted or unsubstituted carbazolyl group, a substituted or unsubstituted fluorenyl group, or a combination thereof.

In an example embodiment of the present invention, R⁹ to R¹⁴ of Chemical Formula 2 may independently be hydrogen, deuterium, or a substituted or unsubstituted C6 to C12 aryl group.

In an example embodiment of the present invention, m of Chemical Formula 2 may be 0 or 1.

In a specific example embodiment of the present invention, Chemical Formula 2 may be one of structures of Group II and *-L¹-Ar¹ and *-L²-Ar² may be one of substituents of Group III.

[Group II]

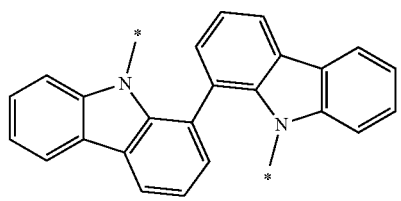

C-1

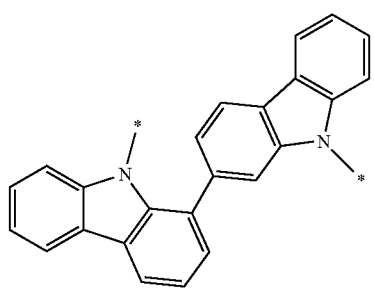

C-2

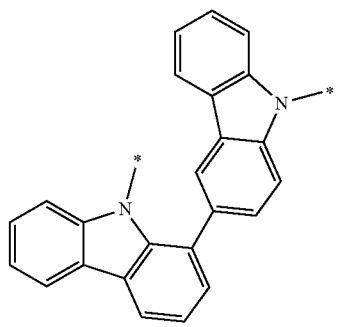

C-3

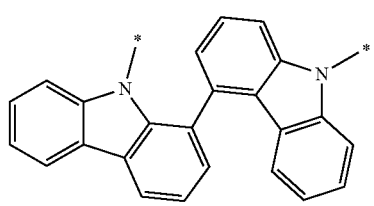

C-4

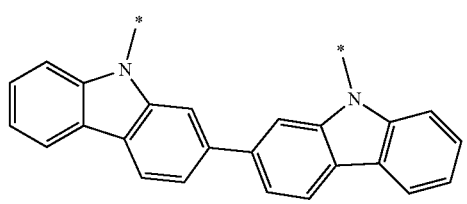

C-5

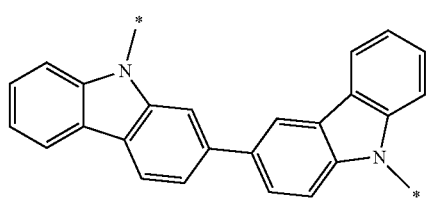

C-6

C-7
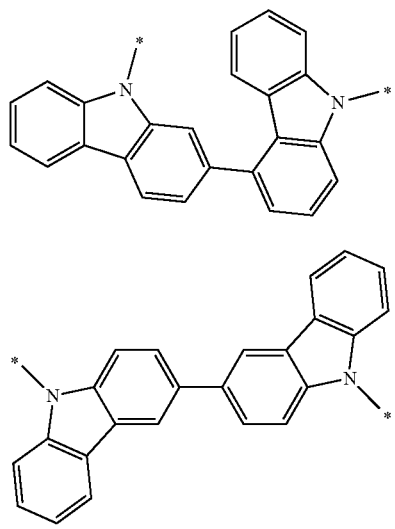
C-8
C-9
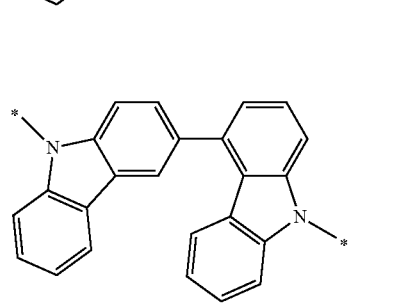
C-10
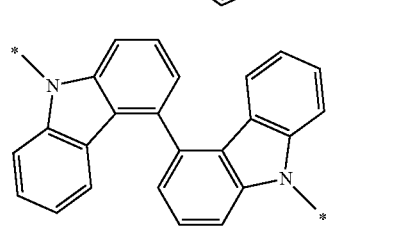
C-11
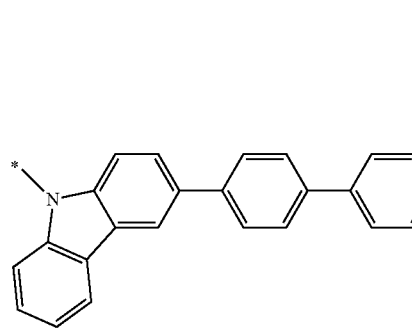
C-12
C-13
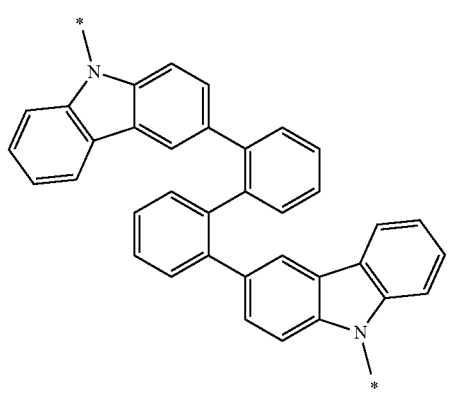
C-14
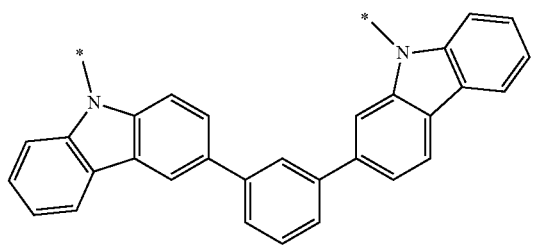
C-15
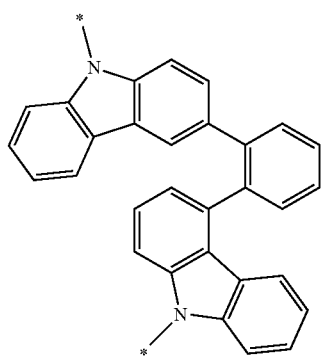
C-16
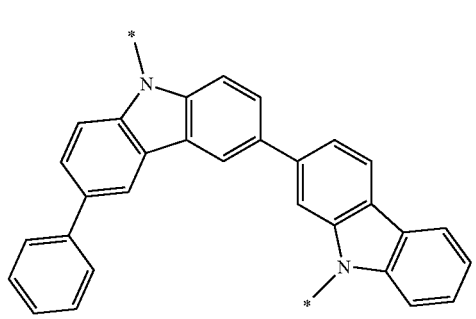

C-17
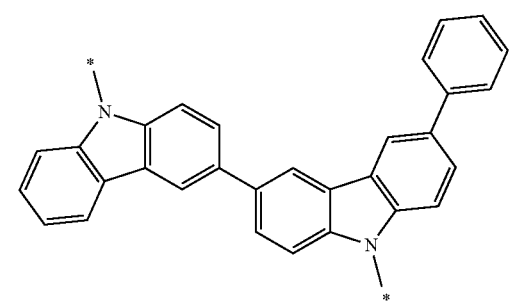
C-18
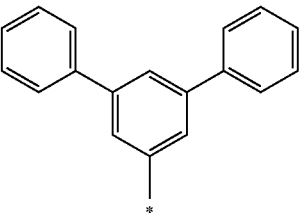
[Group III]
B-1
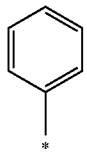
B-2
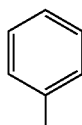
B-3
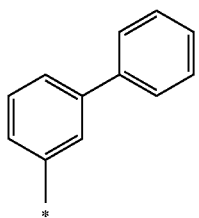
B-4
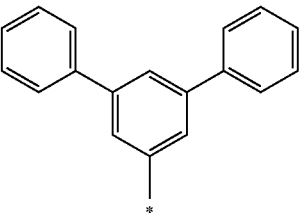
B-5
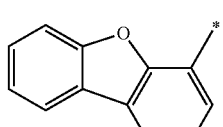
B-6
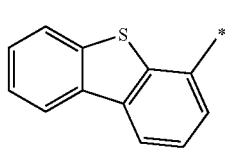
B-7
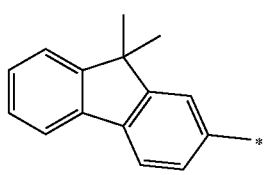
B-8
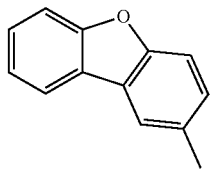
B-9
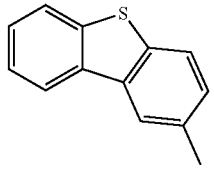
B-10
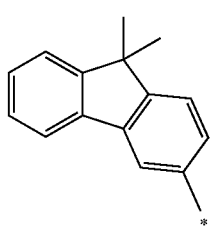

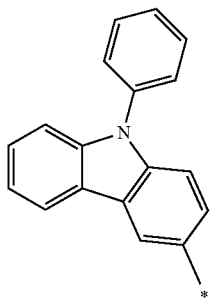
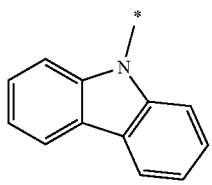
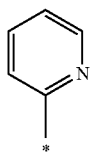
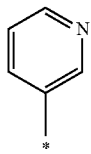
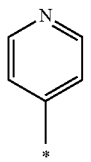
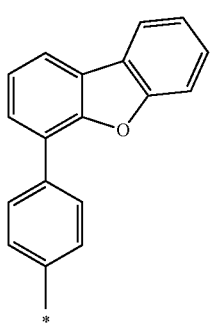
B-11
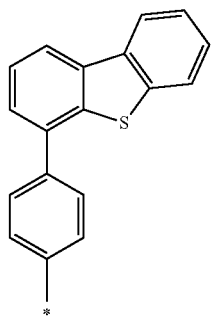
B-12
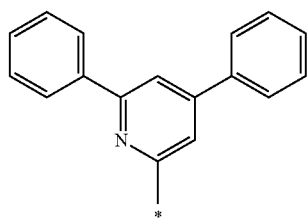
B-13
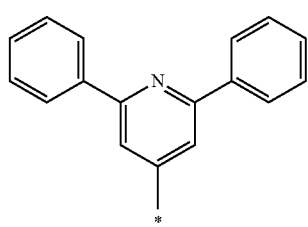
B-14
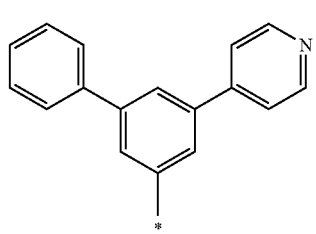
B-15
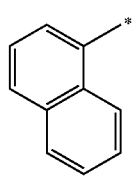
B-16
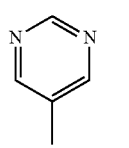
B-17
B-18
B-19
B-20
B-21
B-22
B-23
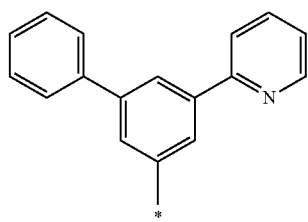

-continued
B-24
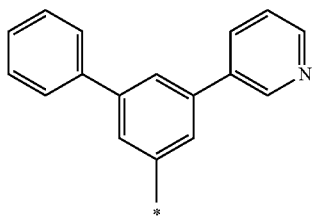
B-25
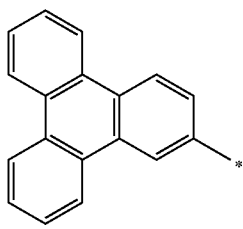
B-26
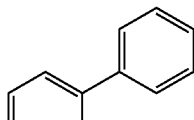
B-27
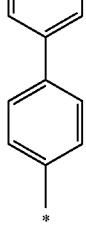
B-28
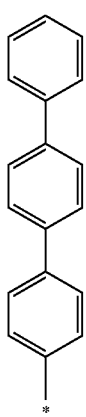
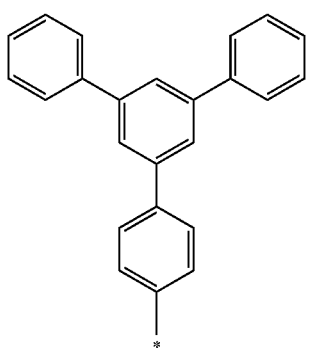
In Groups II and III, * is a linking point.
The second compound for an organic optoelectronic device represented by Chemical Formula 2 may be for example selected from compounds of Group 2.
[Group 2]
[E-1]
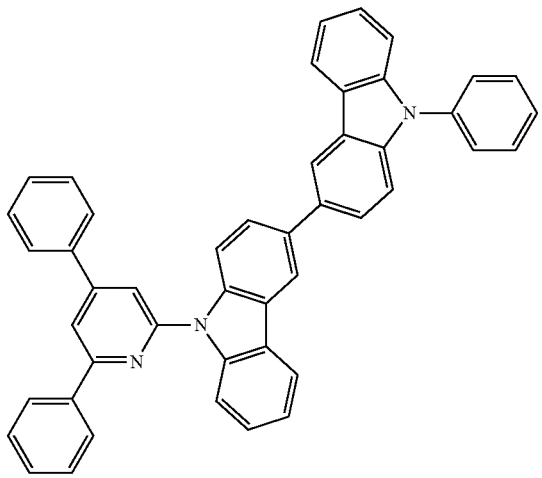
[E-2]
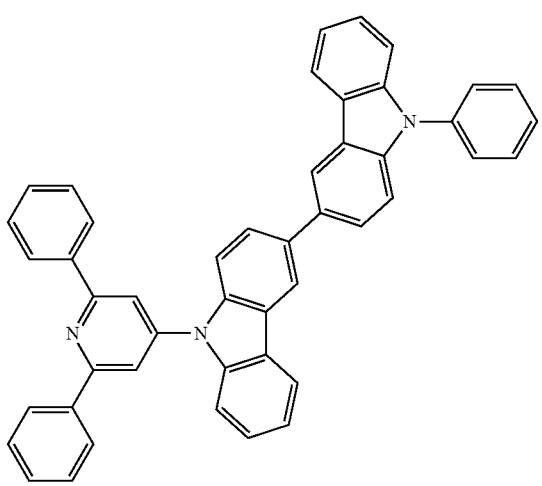
[E-3]
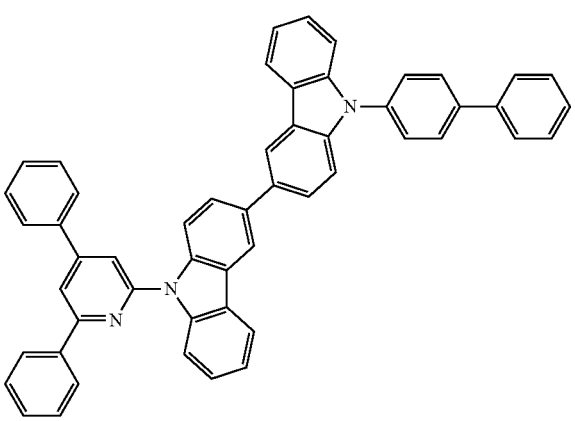

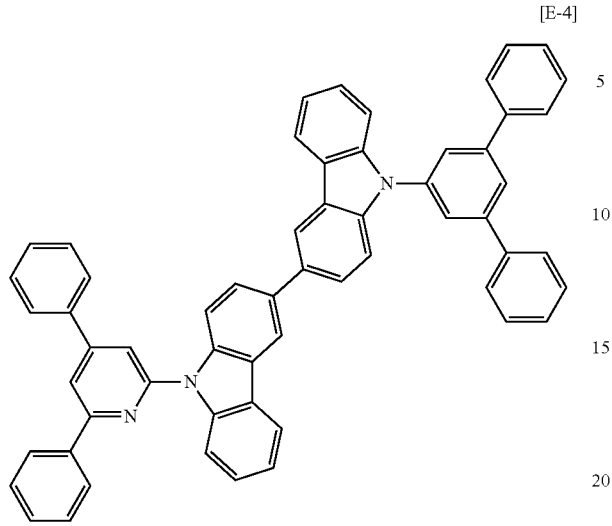
[E-4]
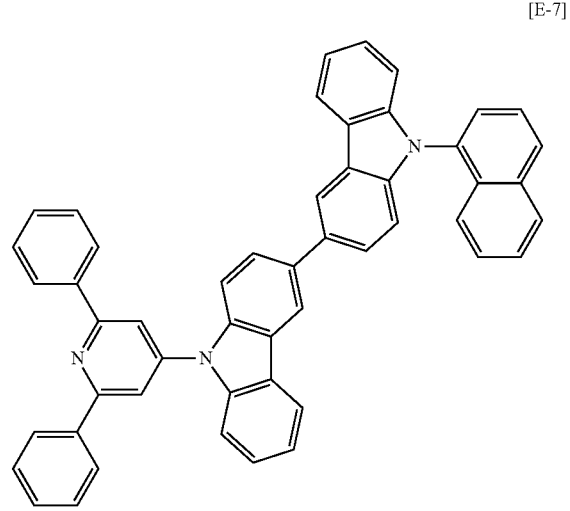
[E-7]
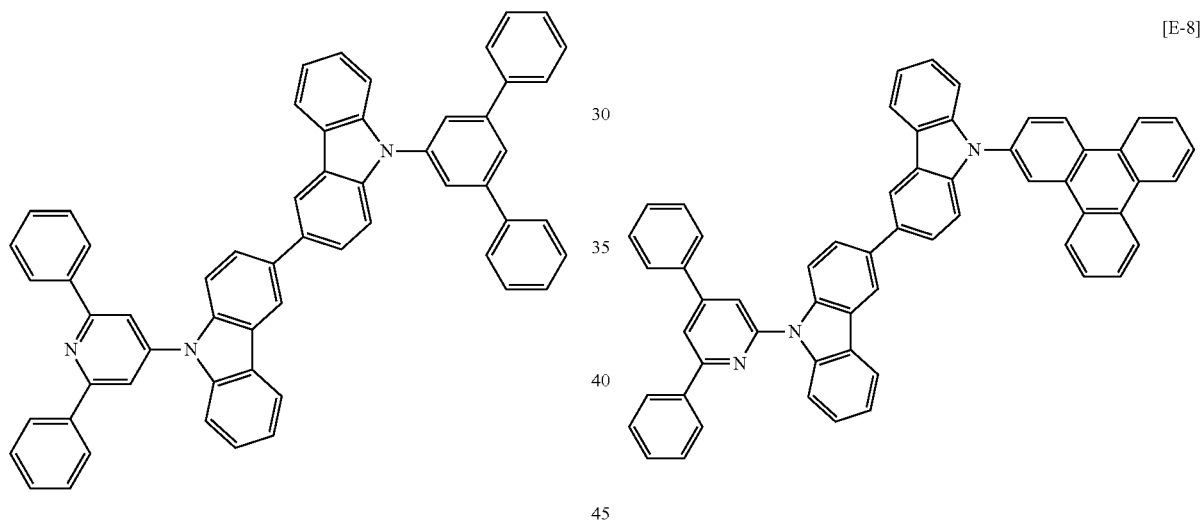
[E-5] [E-8]
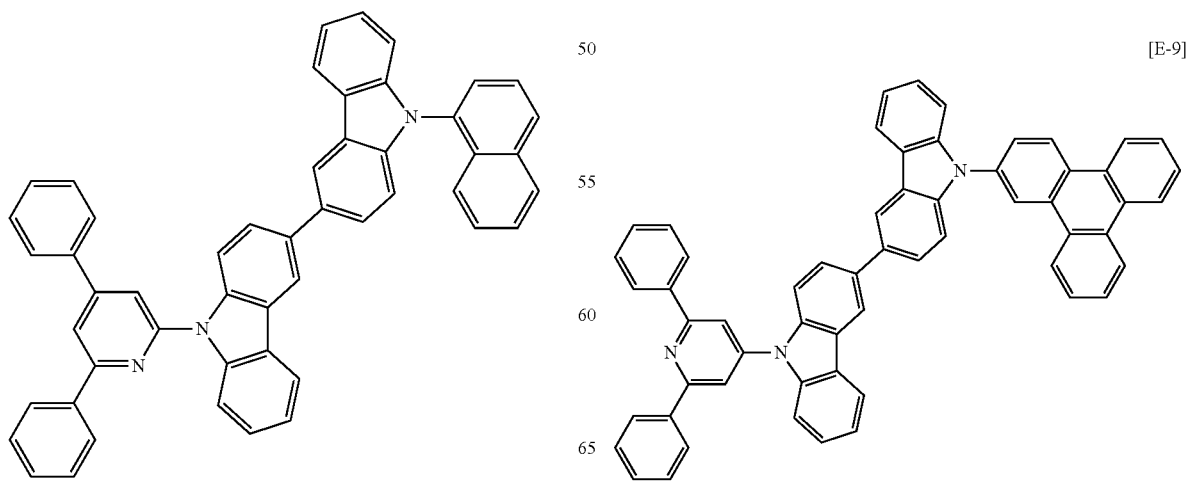
[E-6] [E-9]

[E-10]
[E-11]
[E-12]
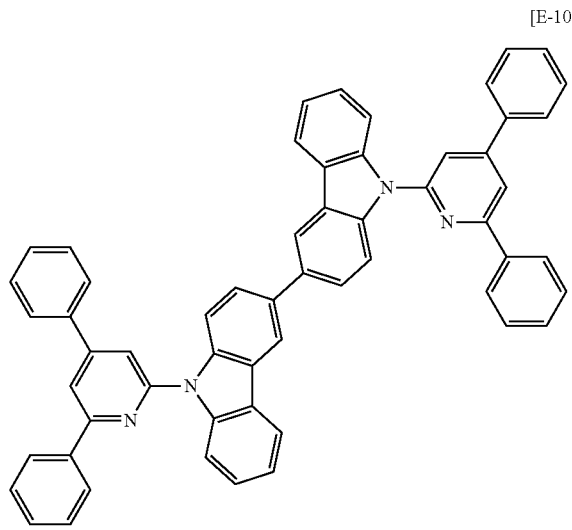
[E-13]
[E-14]
[E-15]
[E-16]
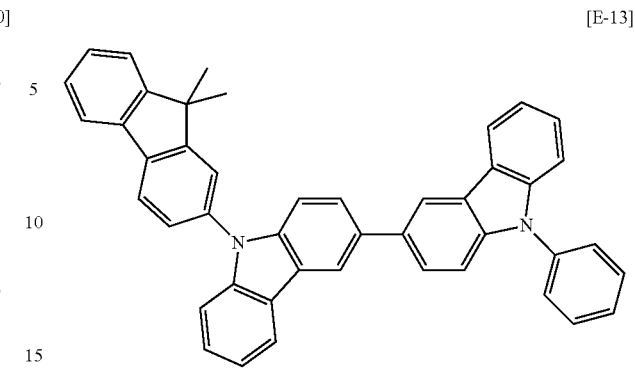
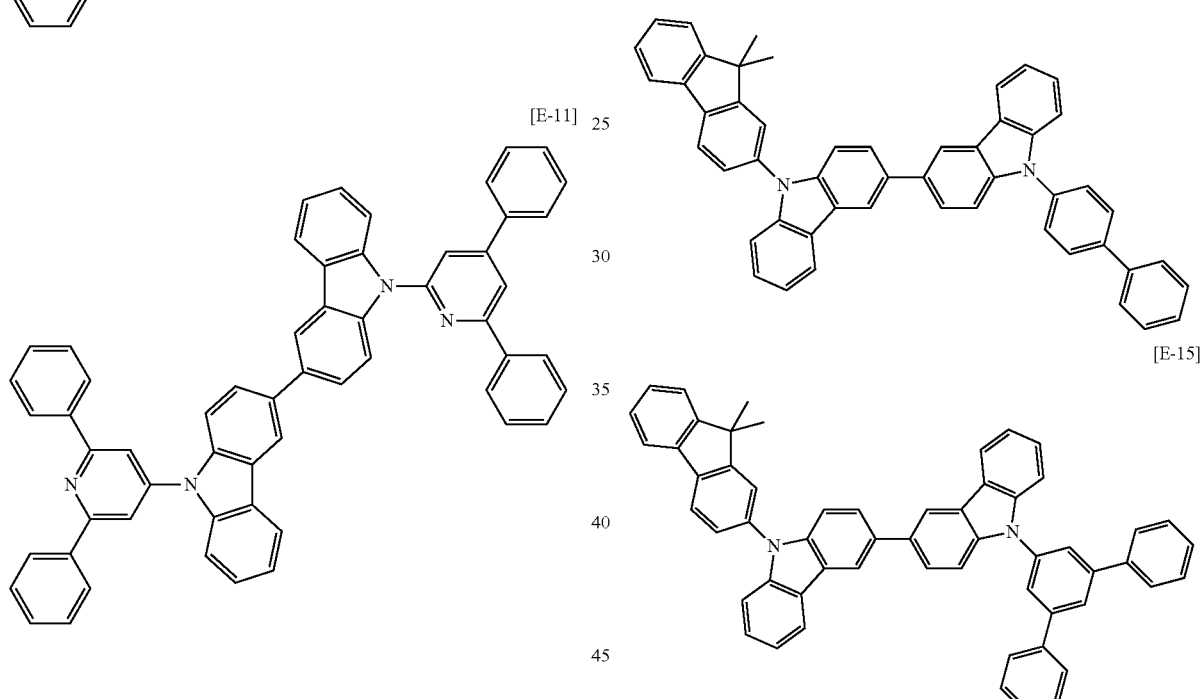
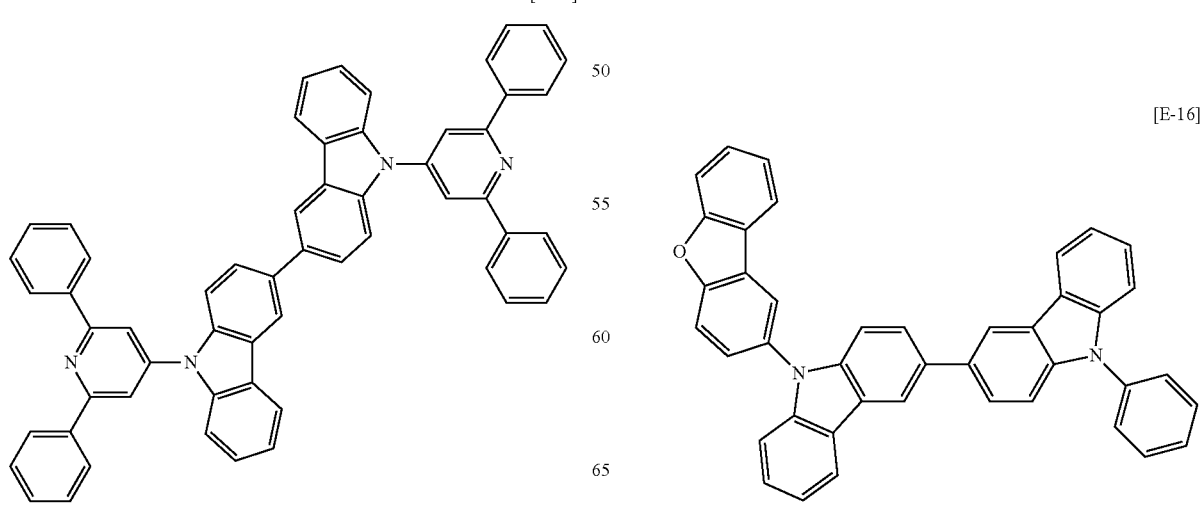

[E-17]
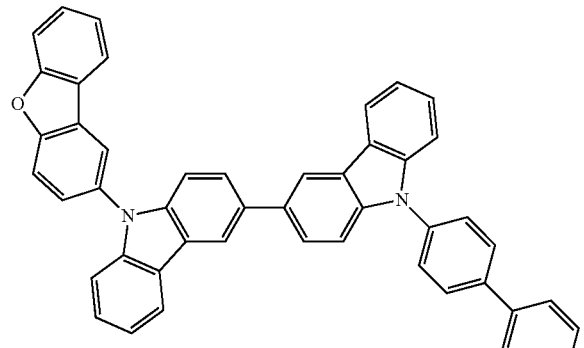
[E-18]
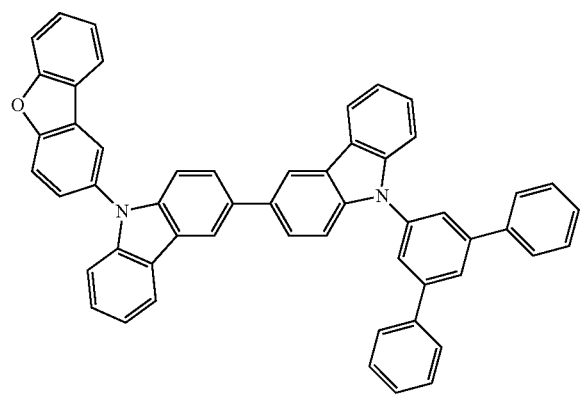
[E-19]
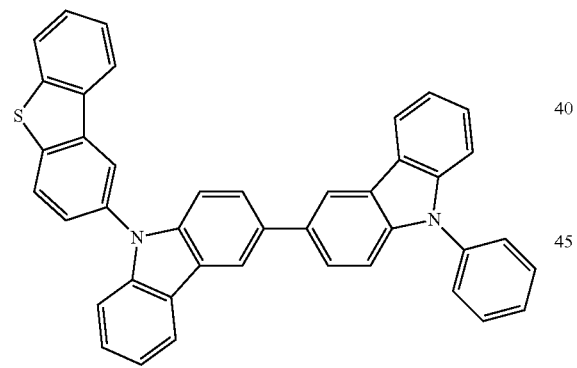
[E-20]
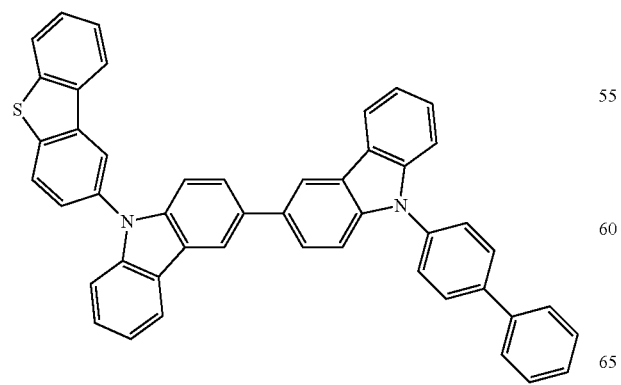
[E-21]
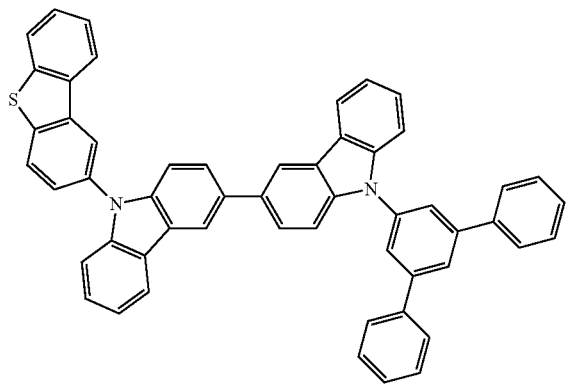
[E-22]
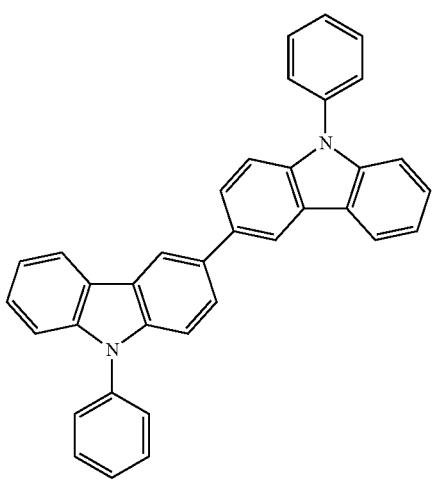
[E-23]
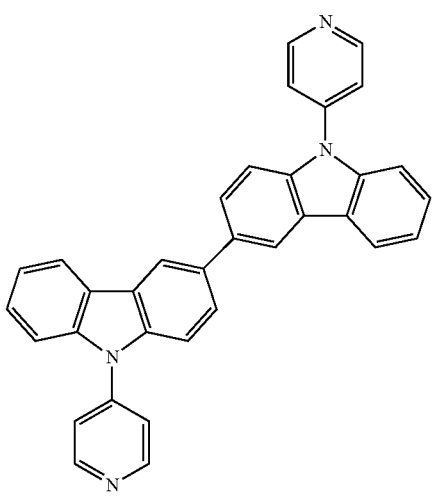

[E-24]
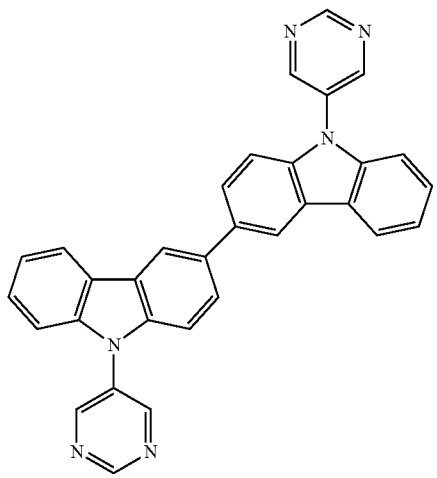
[E-26]
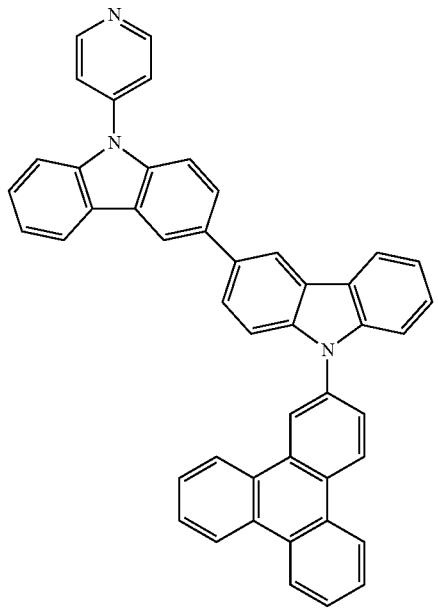
[E-27]
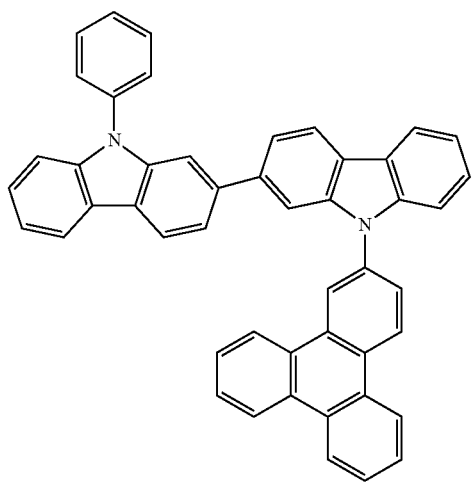
[E-25]
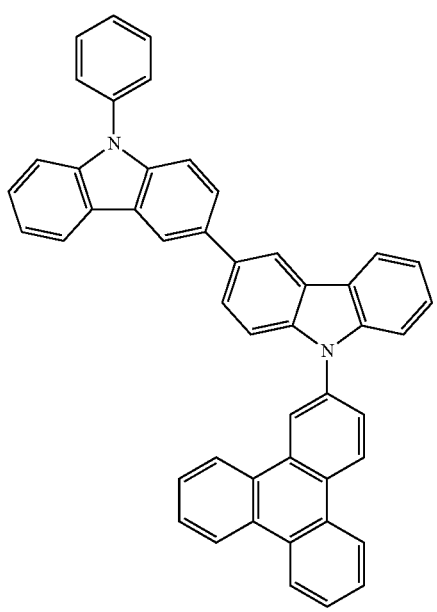
[E-28]
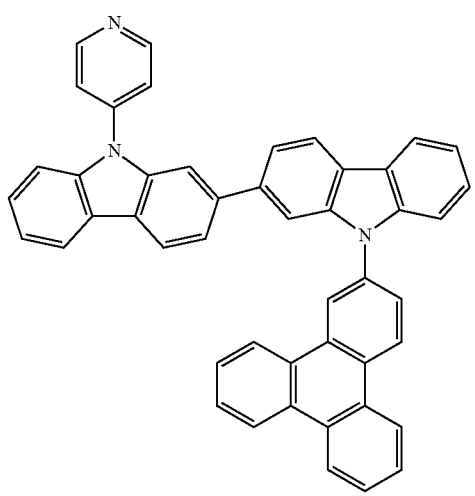

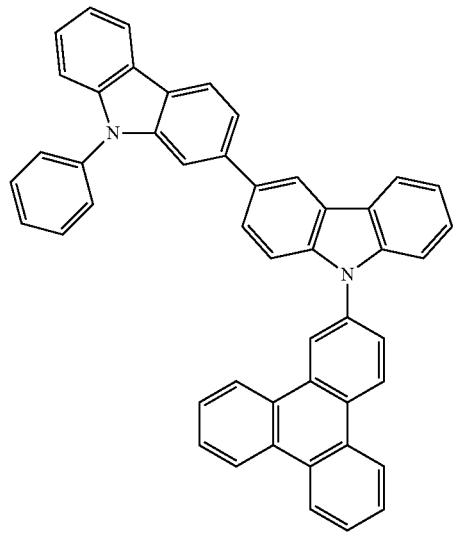
[E-29]
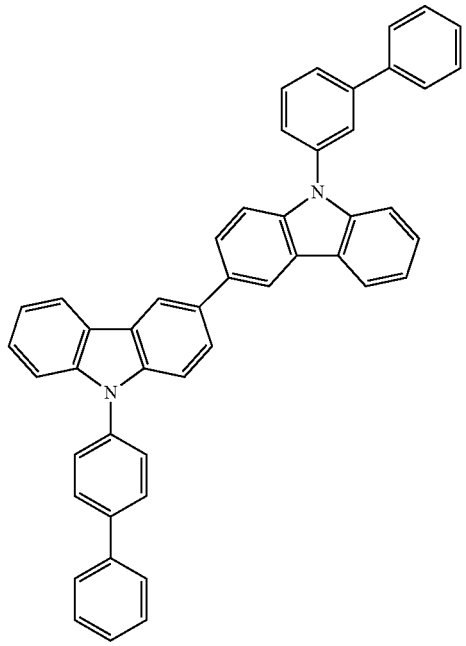
[E-31]
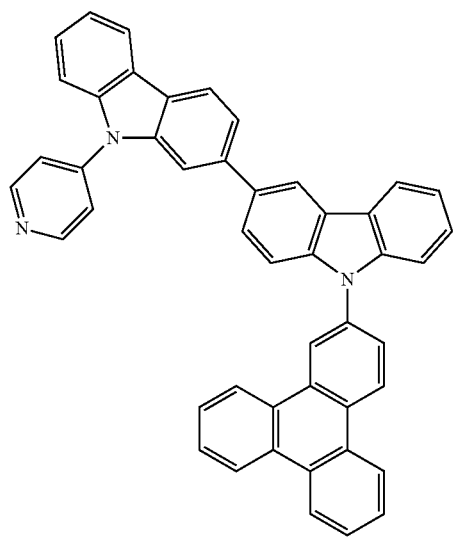
[E-30]
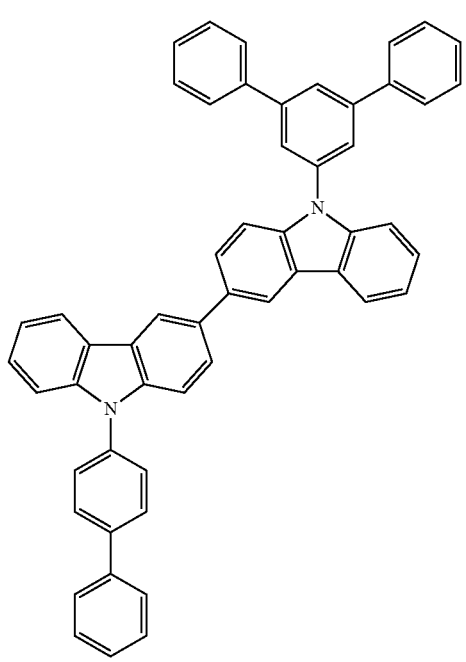
[E-32]

[E-33]
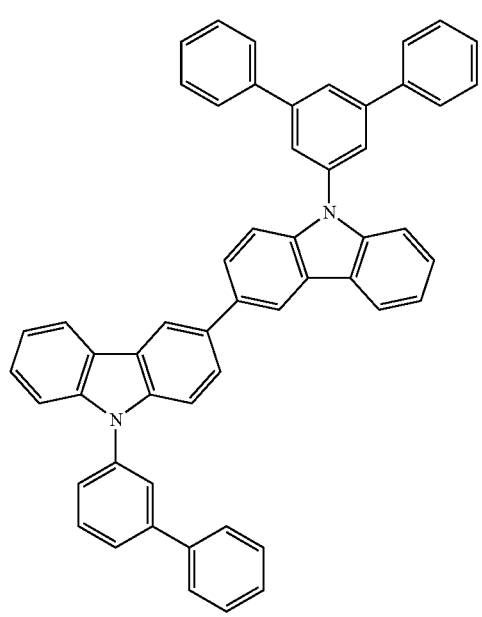
[E-34]
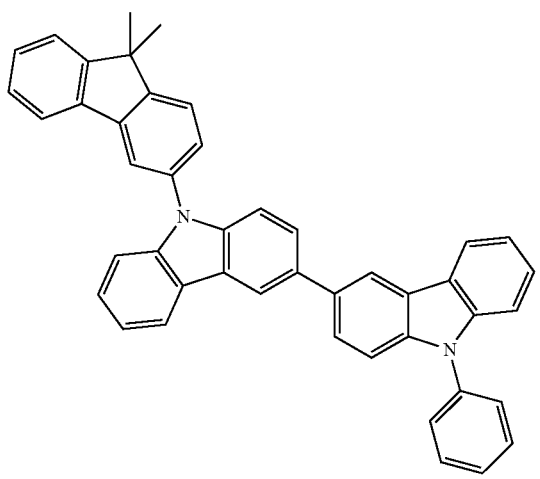
[E-35]
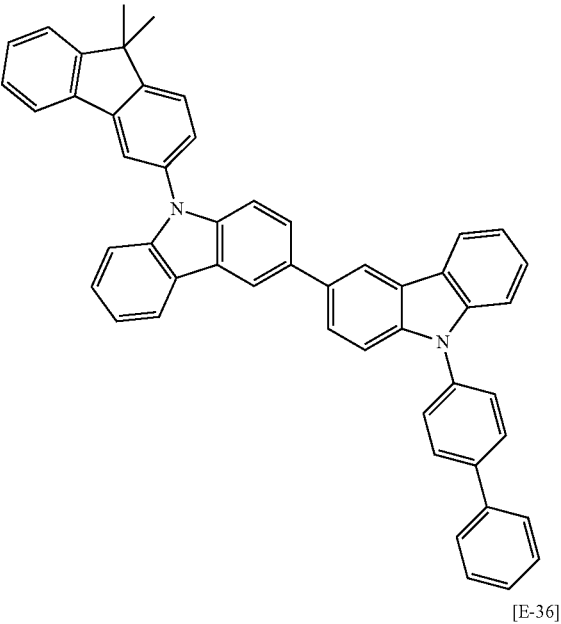
[E-36]
[E-37]
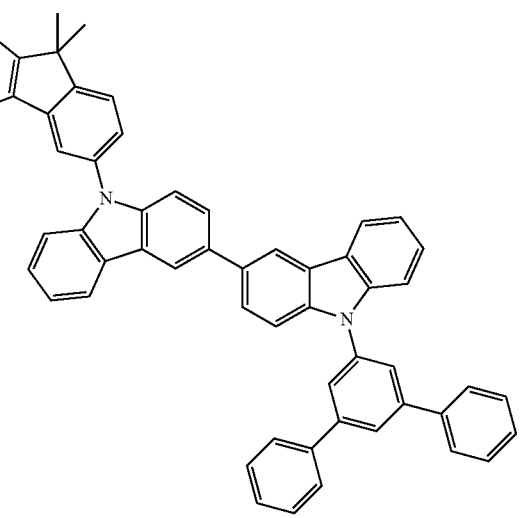

[E-38]
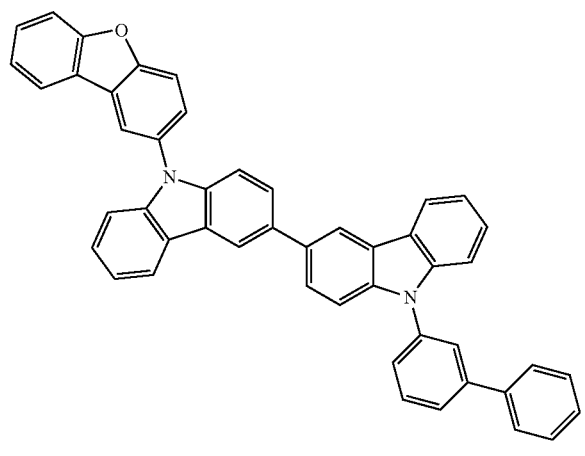
[E-41]
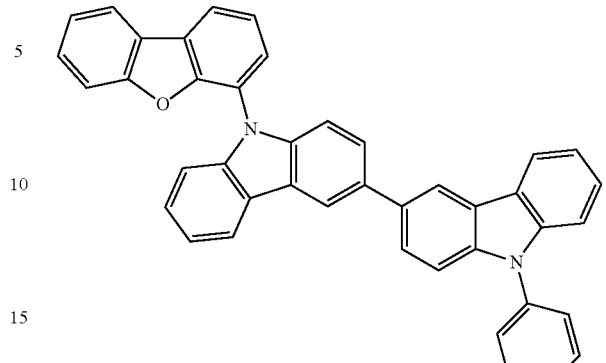
[E-39]
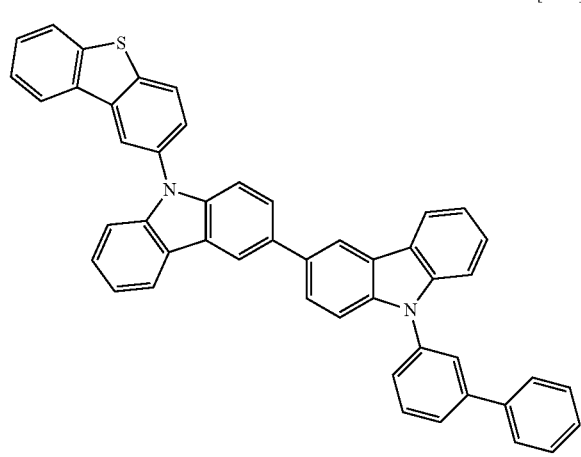
[E-42]
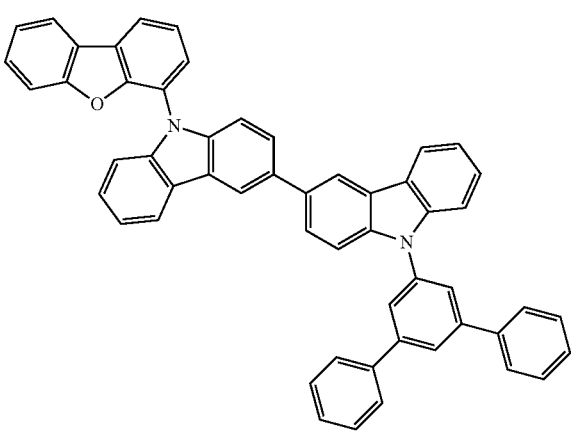
[E-40]
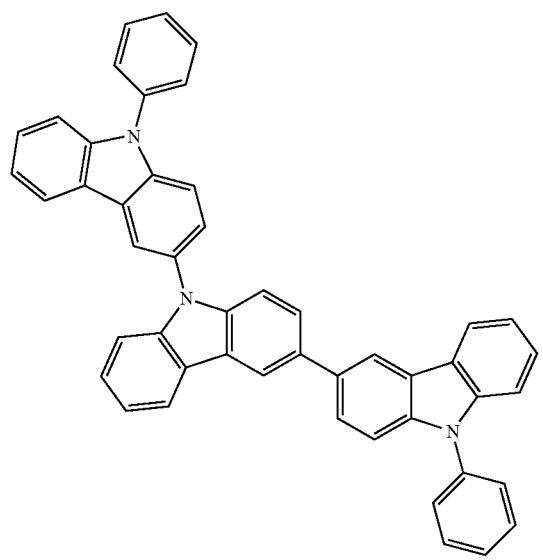
[E-43]

-continued
[E-44]
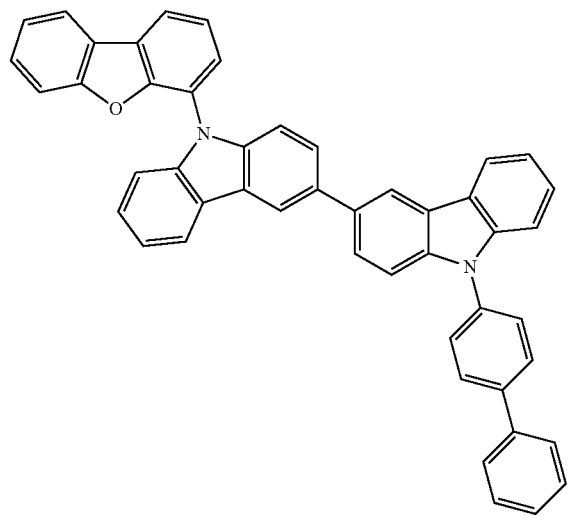
[E-45]
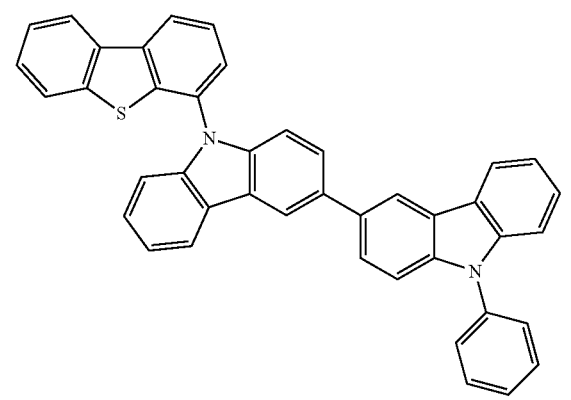
[E-46]
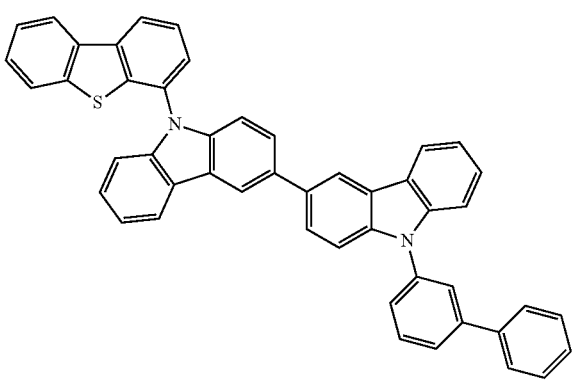
-continued
[E-47]
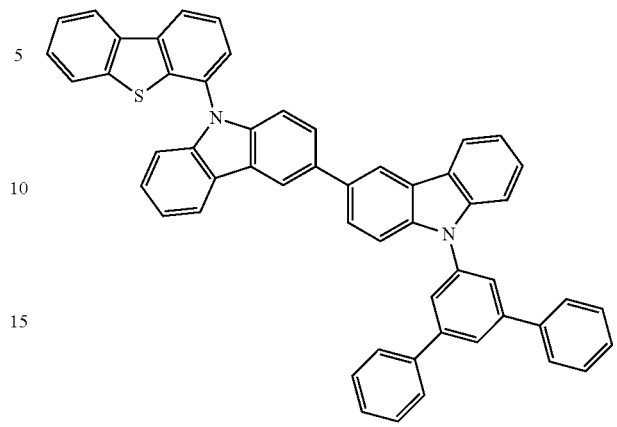
[E-48]
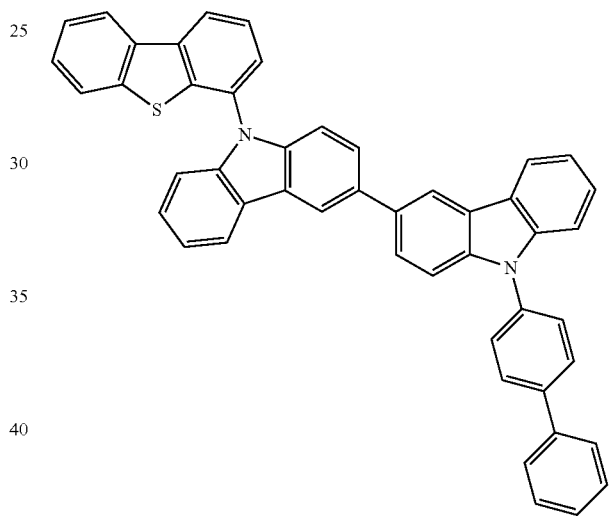
[E-49]
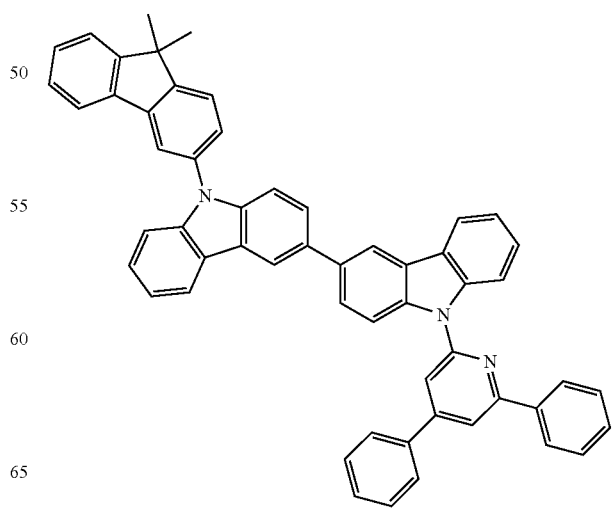

[E-50]
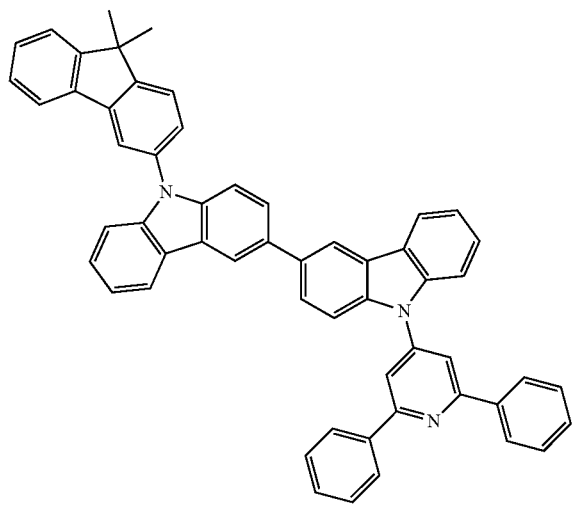
[E-53]
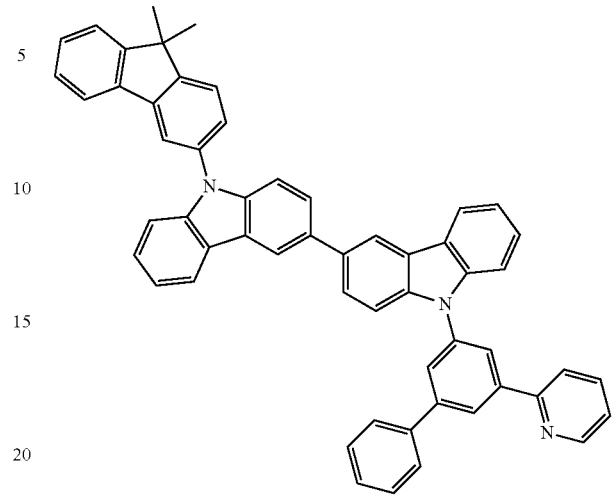
[E-51]
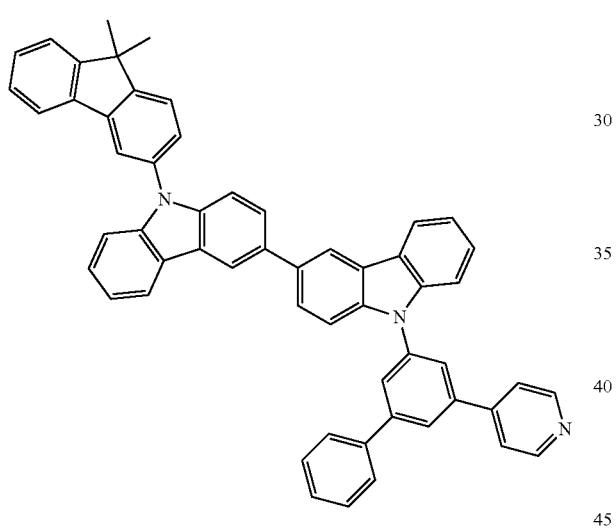
[E-54]
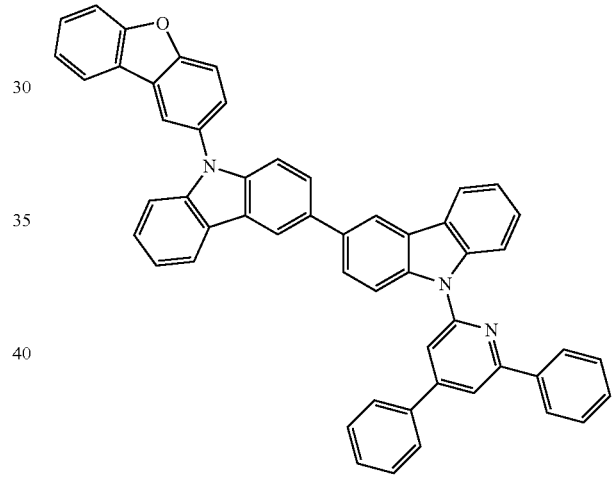
[E-52]
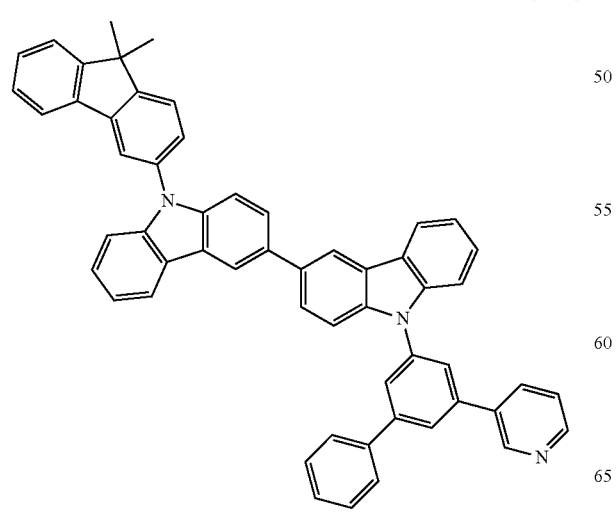
[E-55]
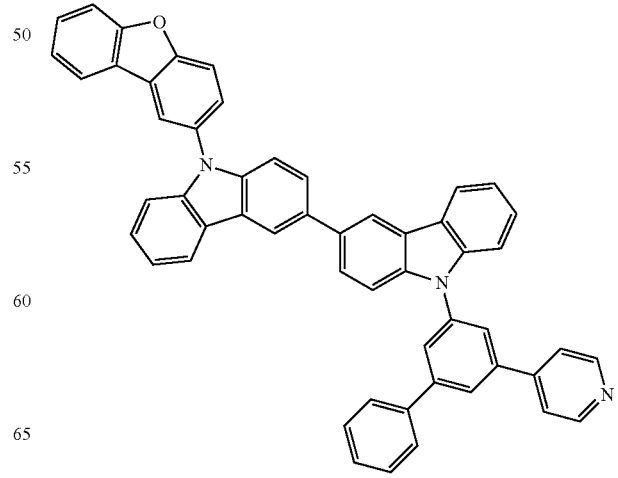

[E-56]
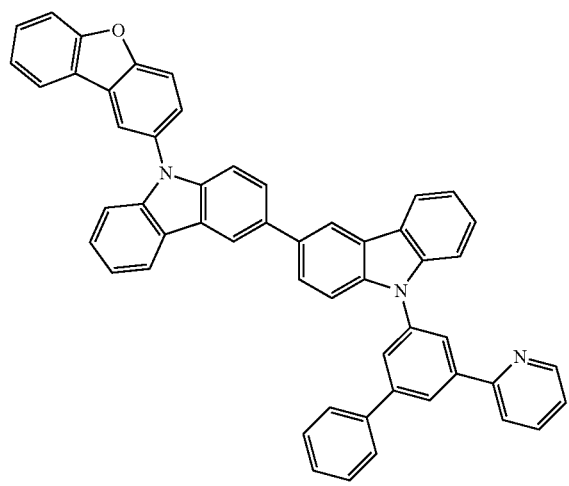
[E-59]
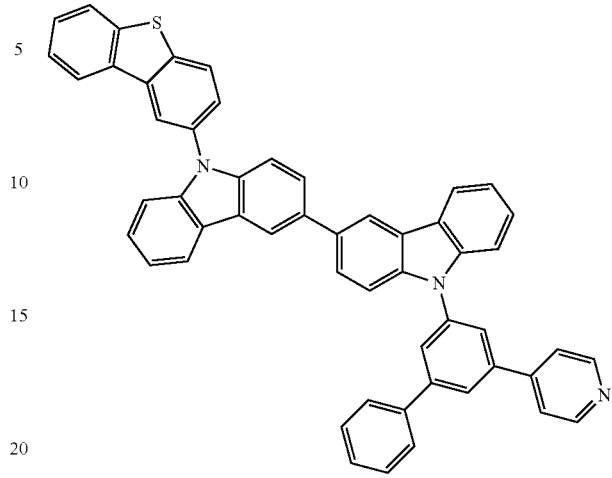
[E-57]
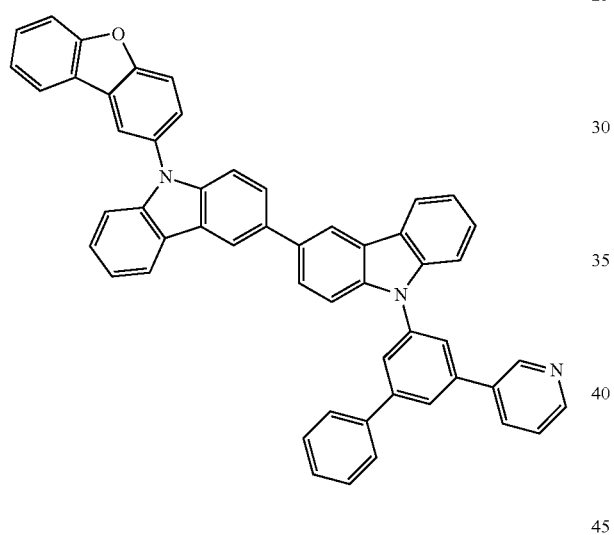
[E-60]
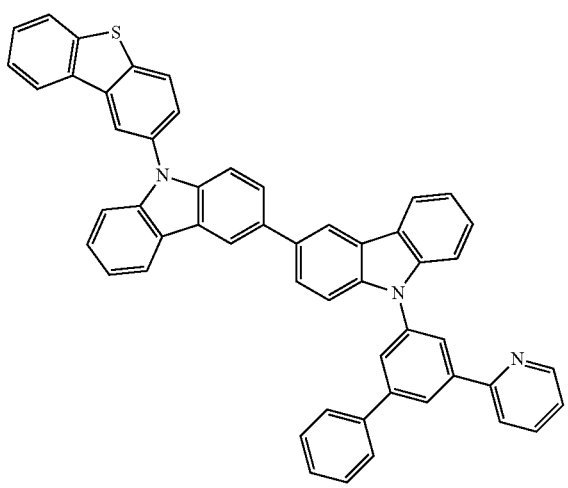
[E-58]
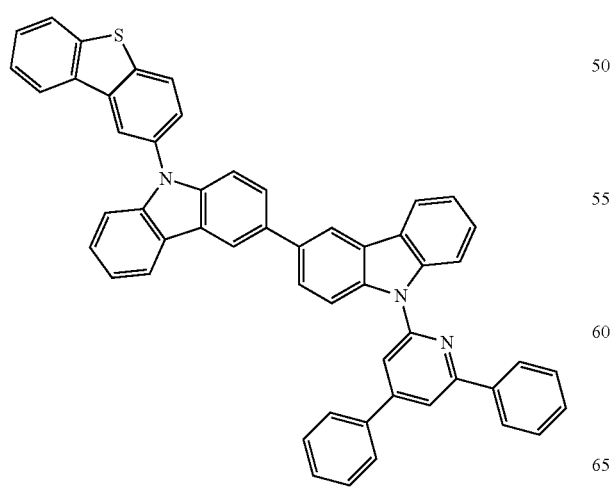
[E-61]
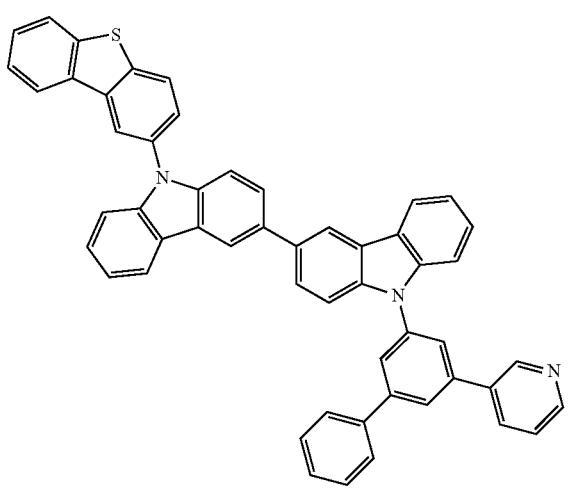

[E-62]
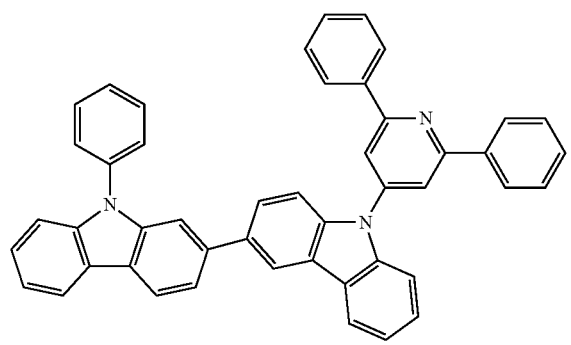
[E-63]
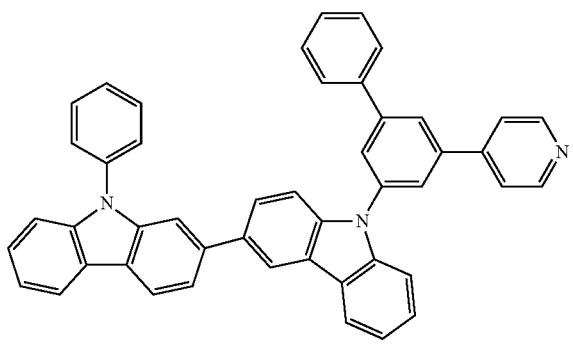
[E-64]
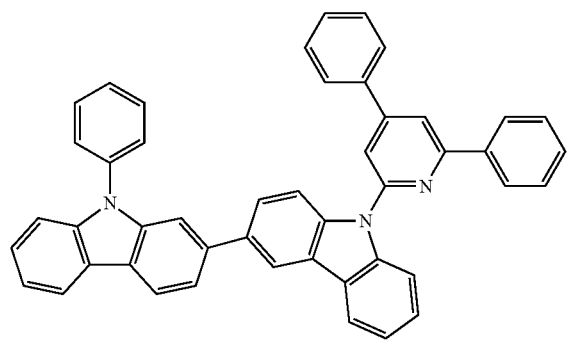
[E-65]
[E-66]
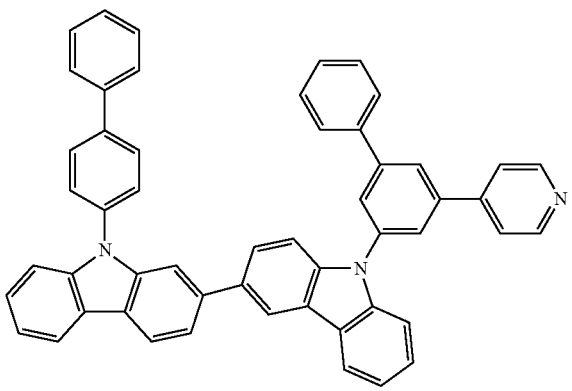
[E-67]
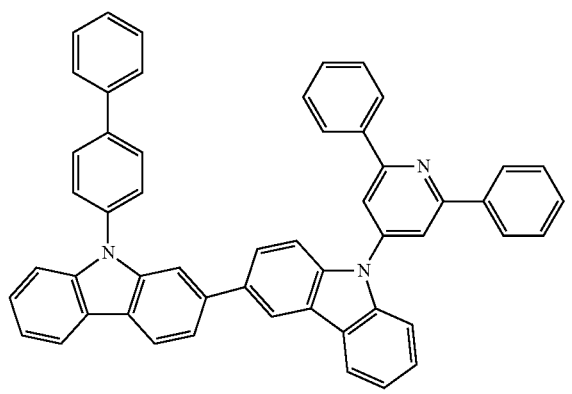
[E-68]
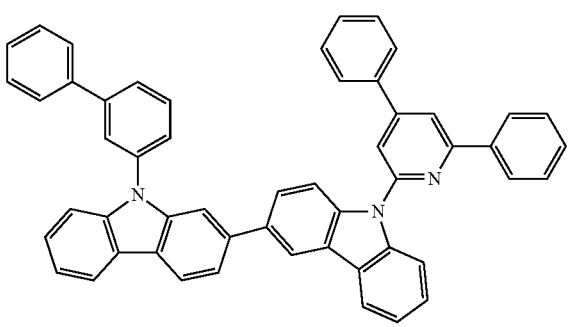
[E-69]
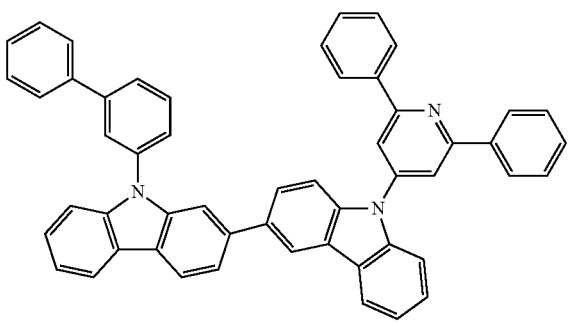

[E-70]
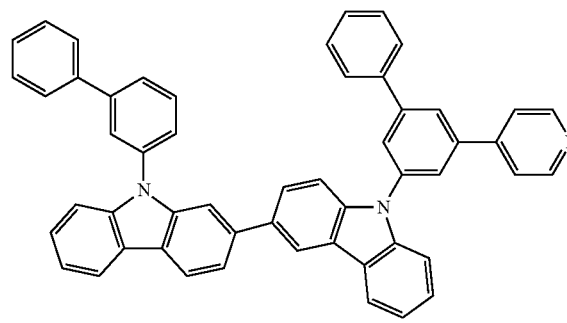
[E-74]
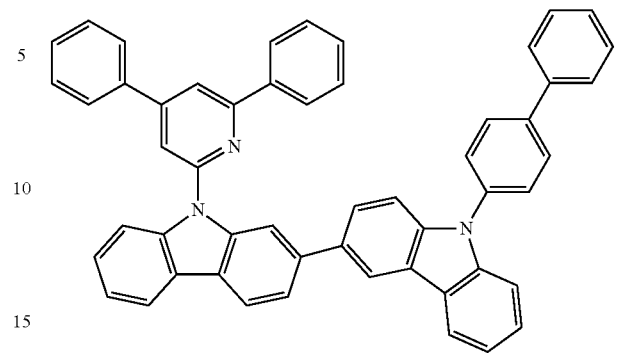
[E-71]
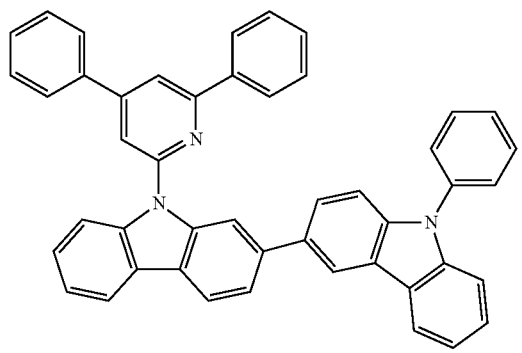
[E-75]
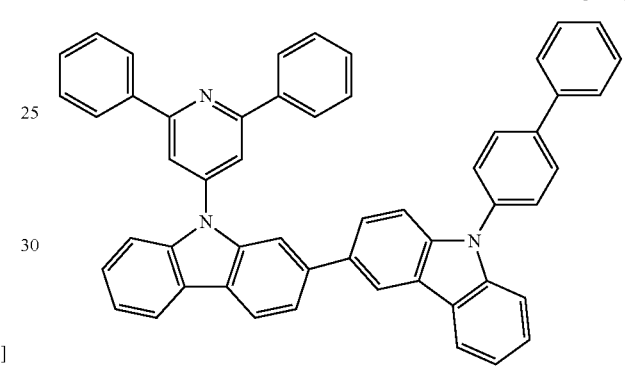
[E-72]
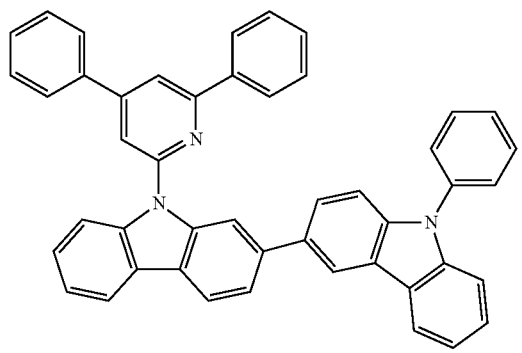
[E-76]
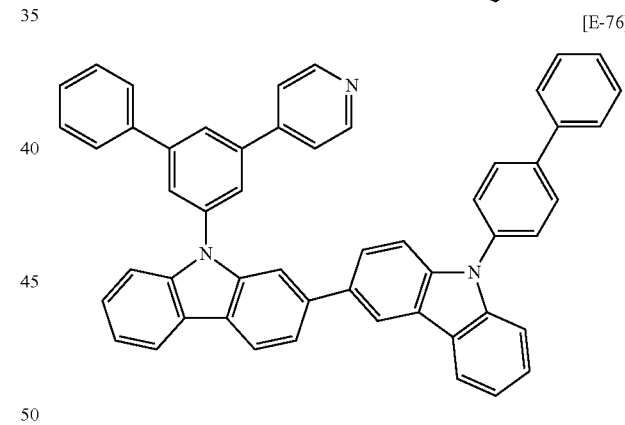
[E-73]
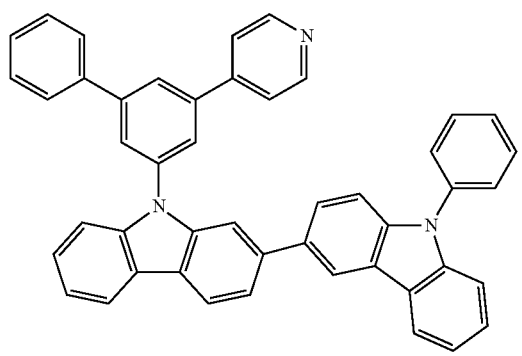
[E-77]
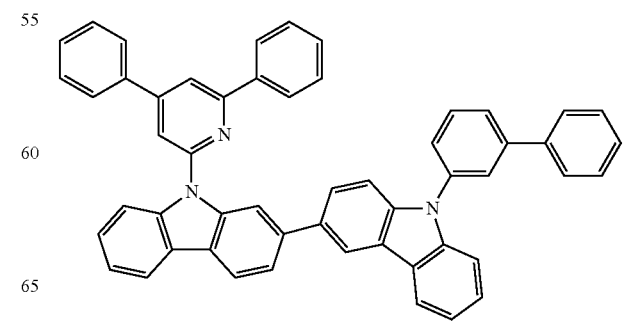

[E-78]
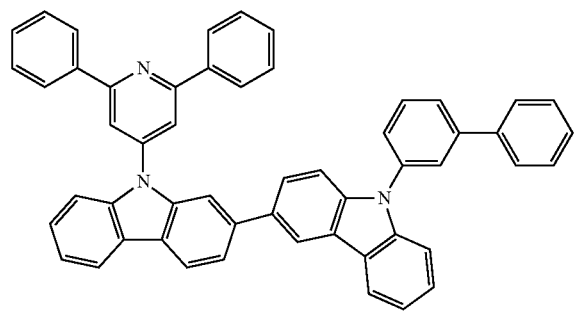
[E-82]
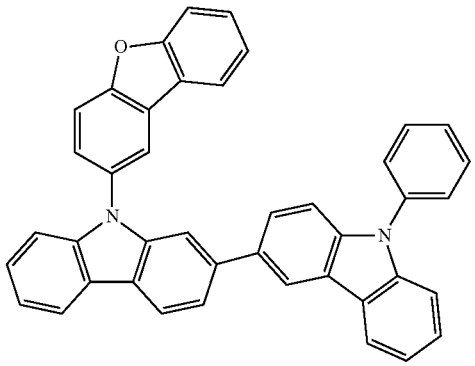
[E-79]
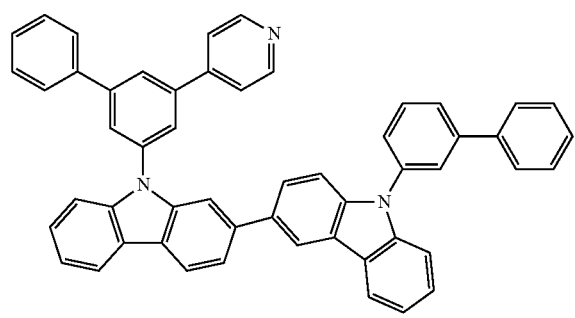
[E-83]
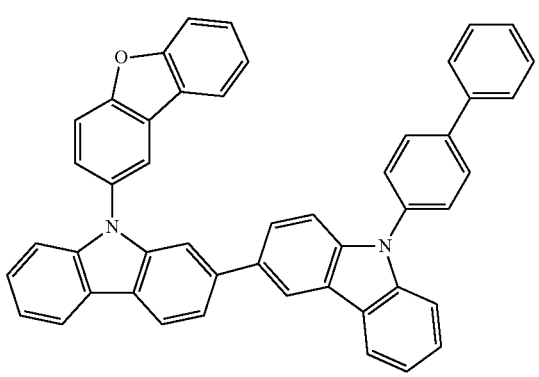
[E-80]
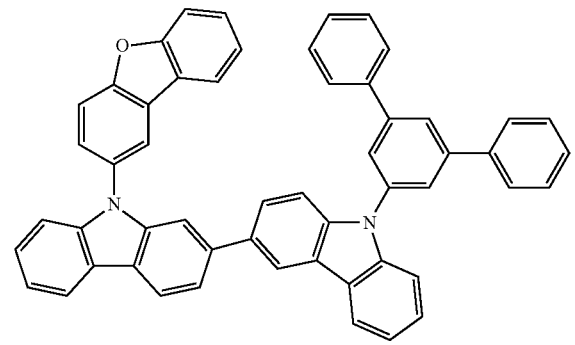
[E-84]
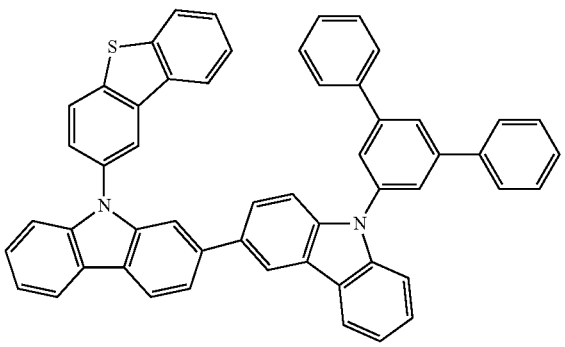
[E-81]
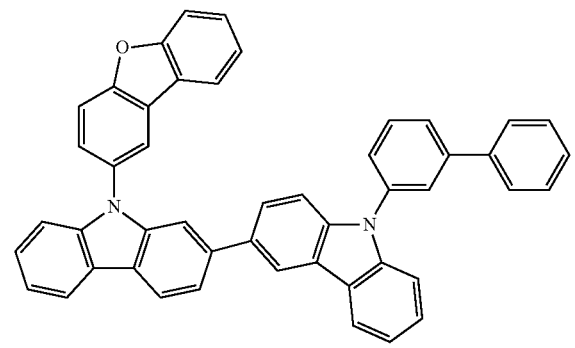
[E-85]

[E-86]
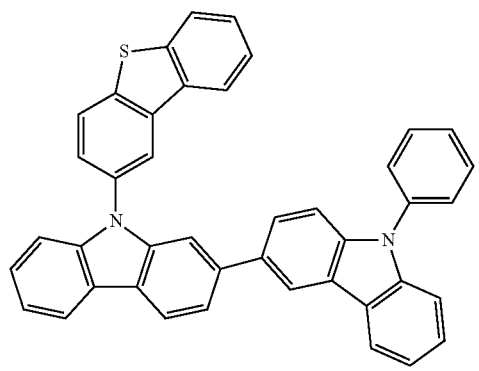
[E-90]
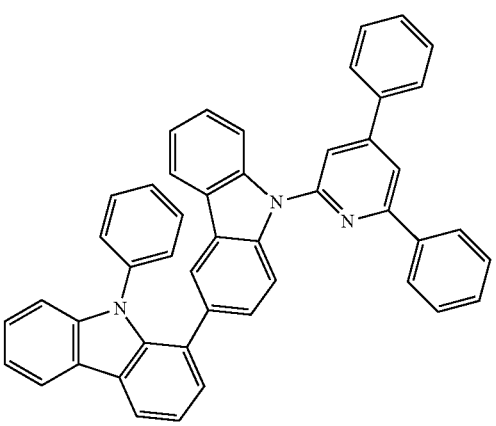
[E-87]
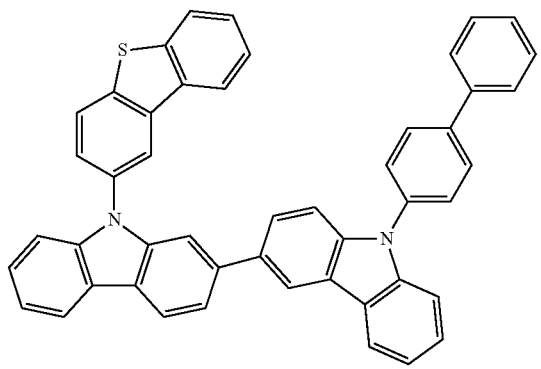
[E-91]
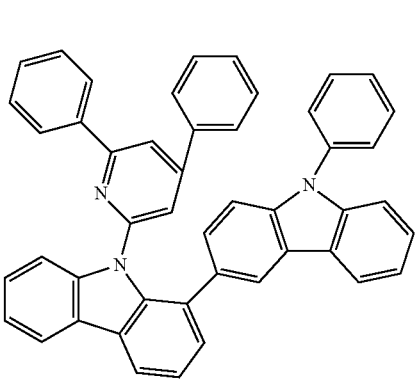
[E-88]
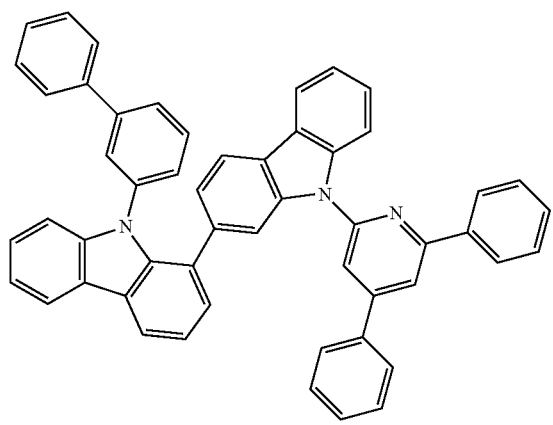
[E-92]
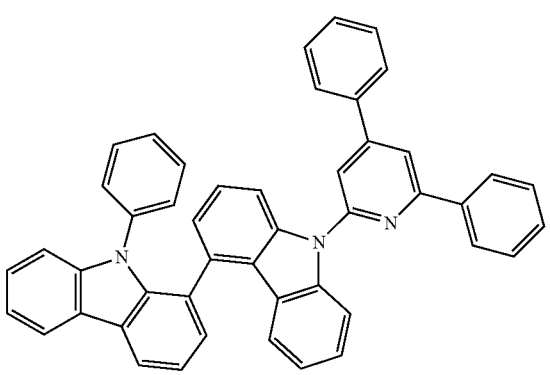
[E-89]
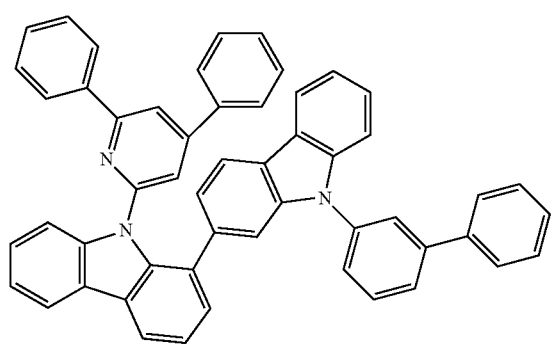
[E-93]
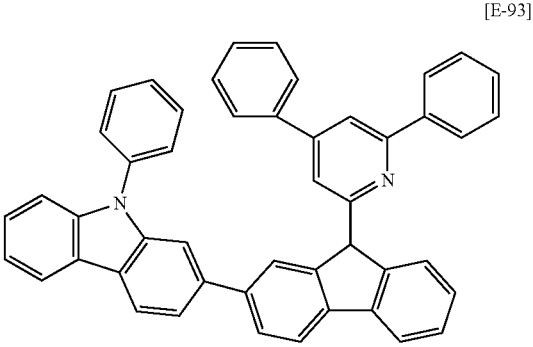

[E-94]
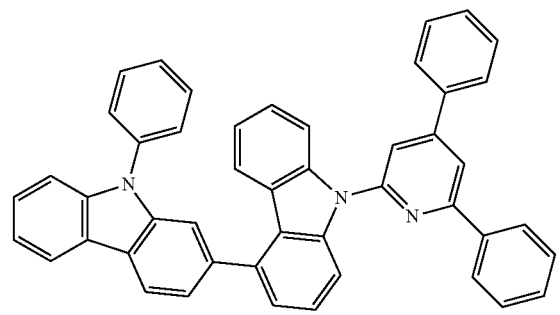
[E-98]
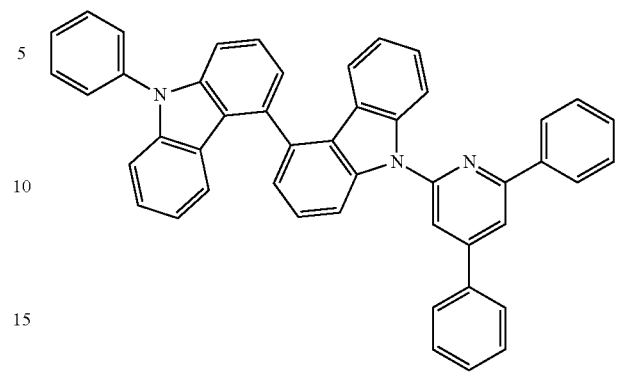
[E-95]
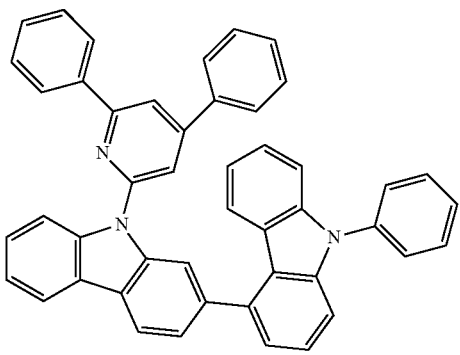
[E-99]
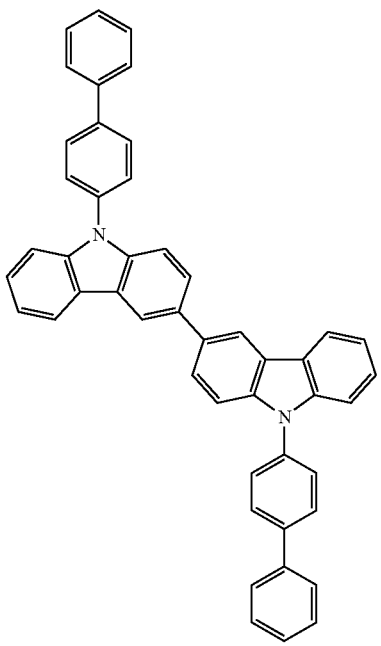
[E-96]
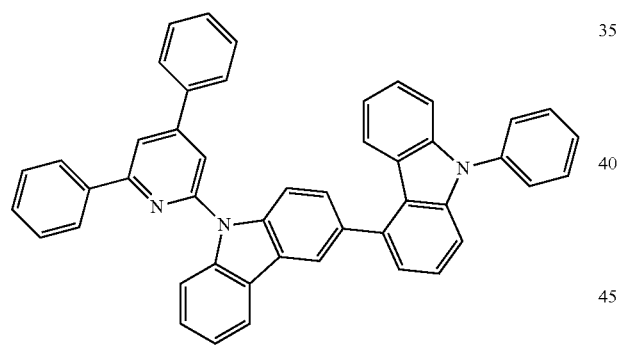
[E-100]
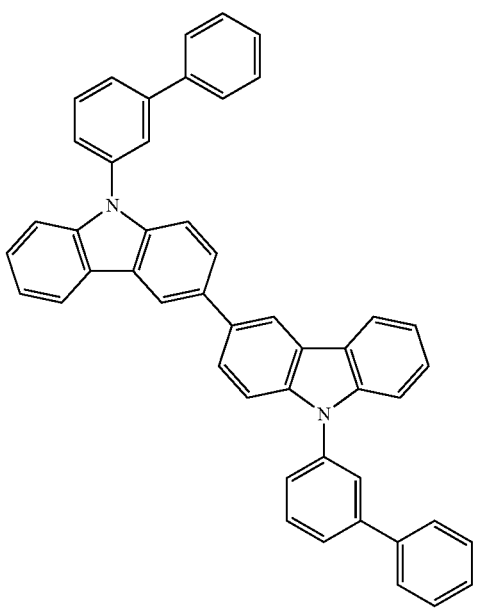
[E-97]
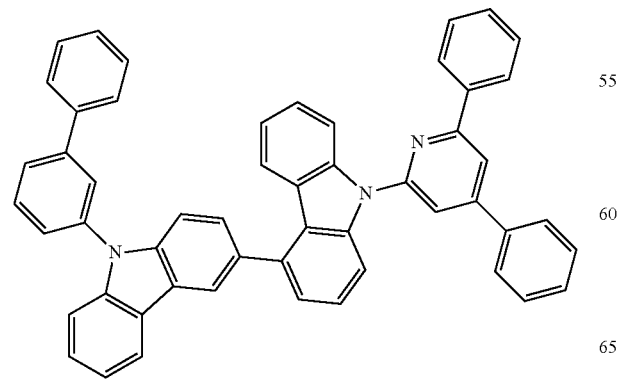

[E-101]
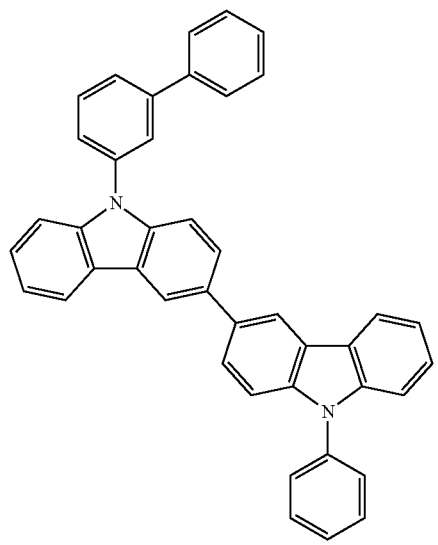
[E-102]
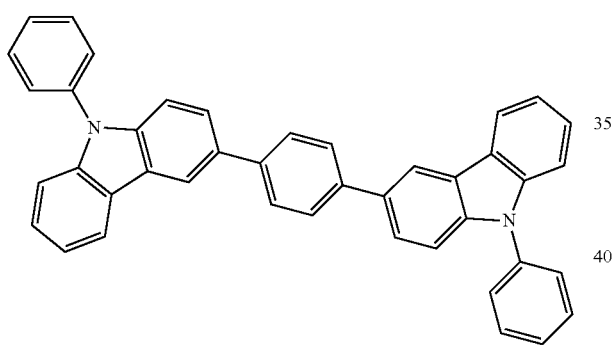
[E-103]
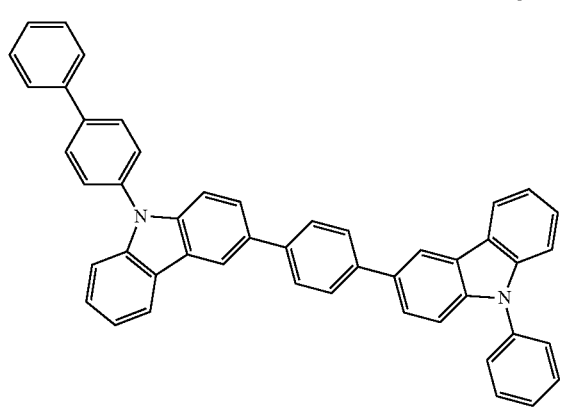
[E-104]
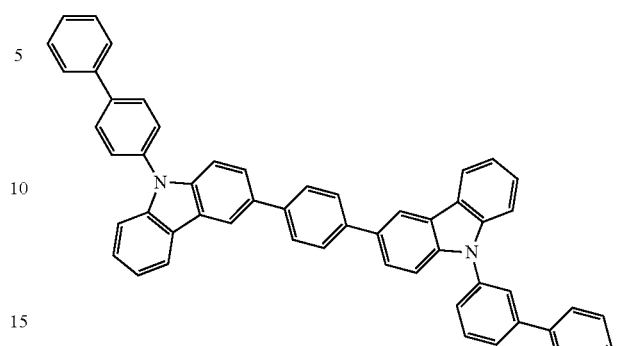
[E-105]
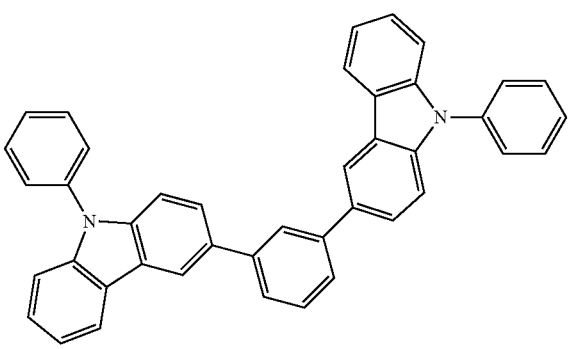
[E-106]
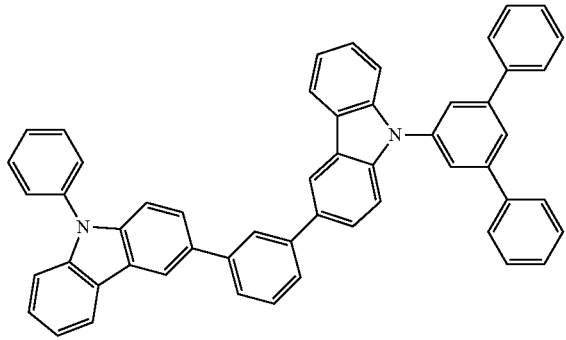
[E-107]
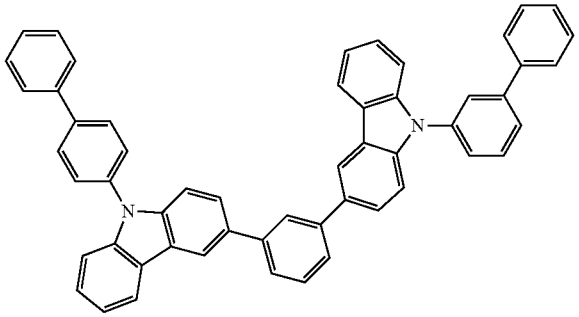

[E-108]
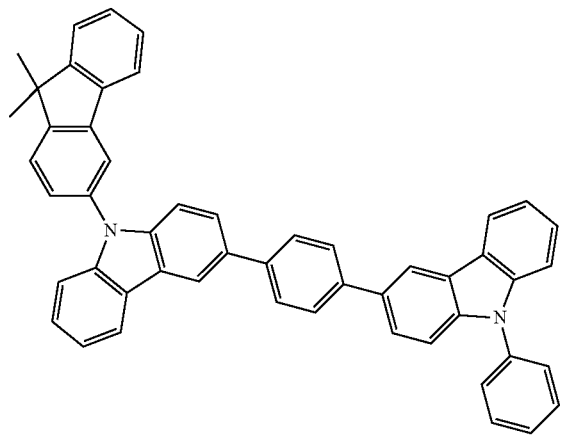
[E-109]
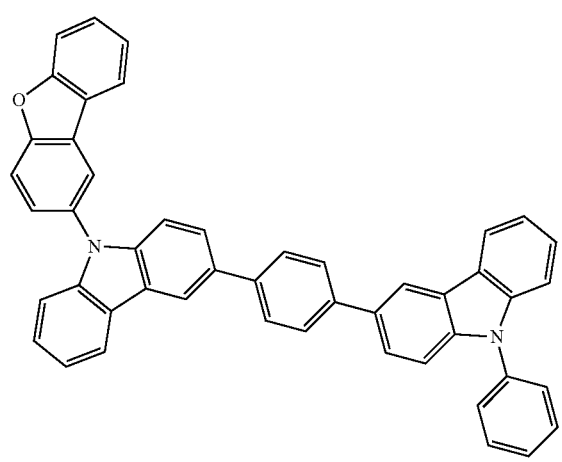
[E-110]
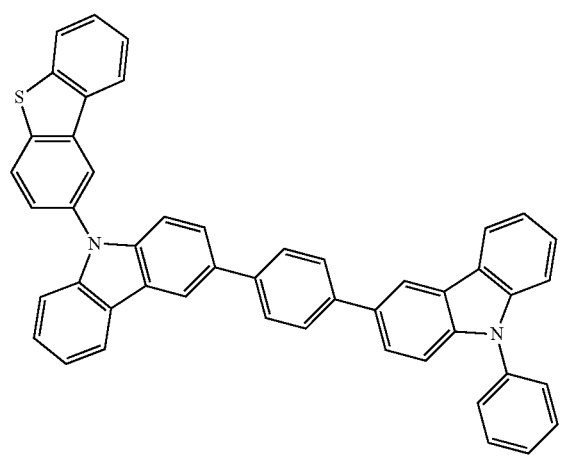
[E-111]
[E-112]
[E-113]
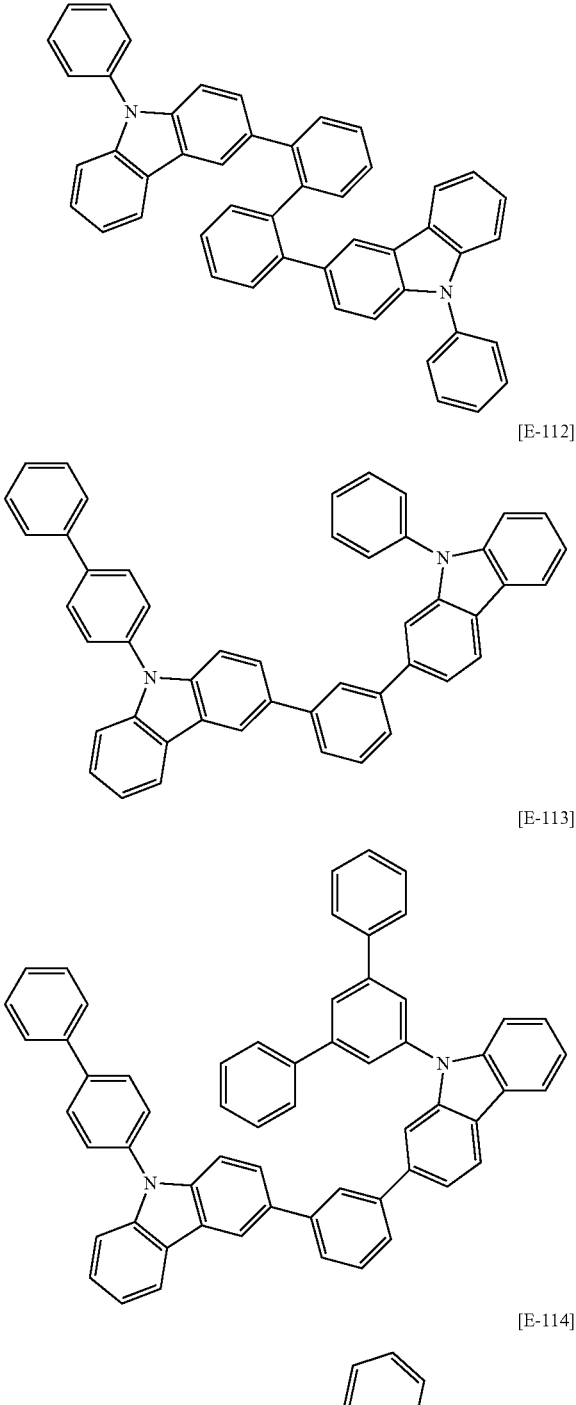
[E-114]
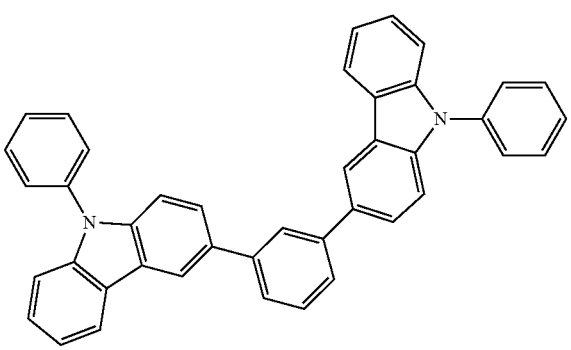

[E-115]
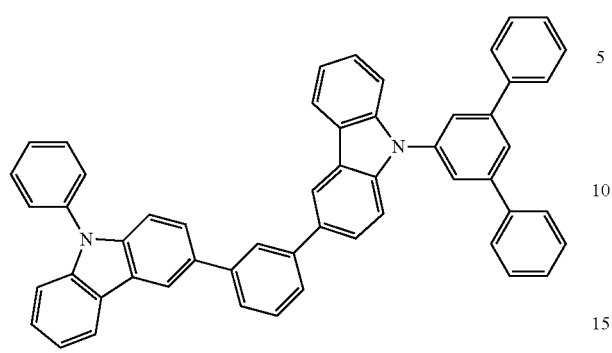
[E-118]
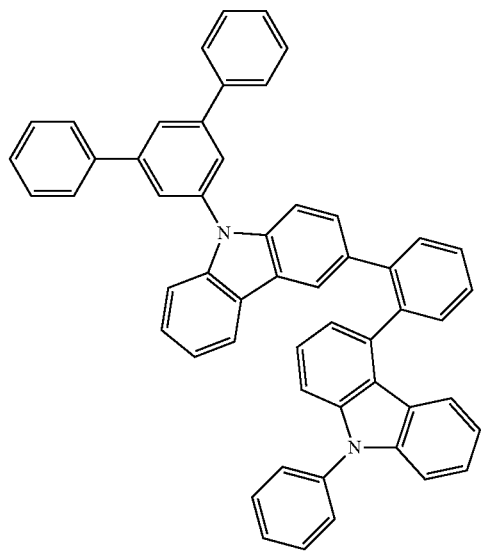
[E-116]
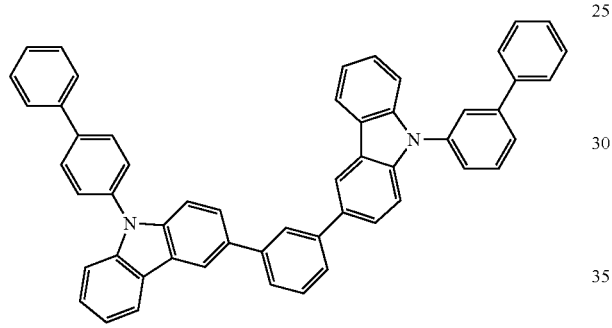
[E-119]
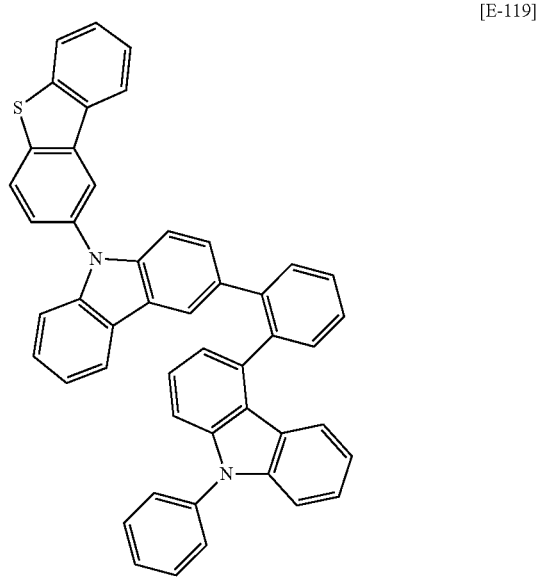
[E-117]
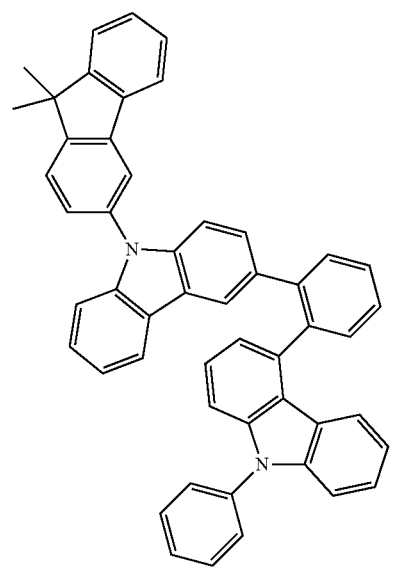
[E-120]
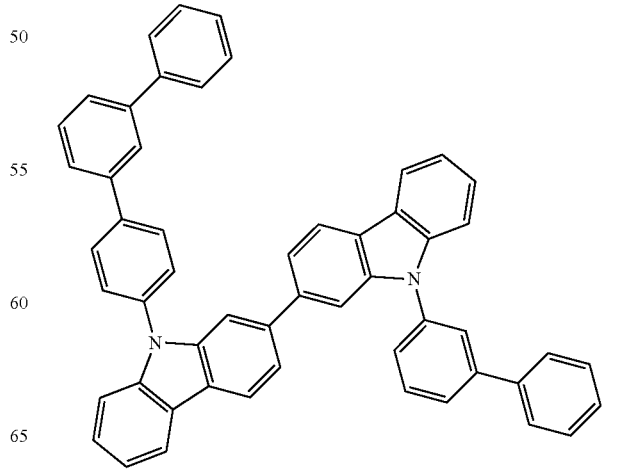

[E-121]
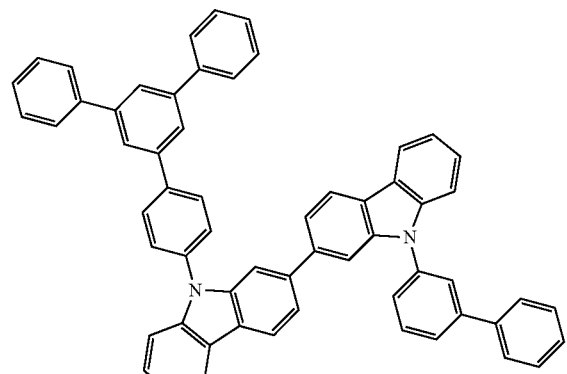
[E-122]
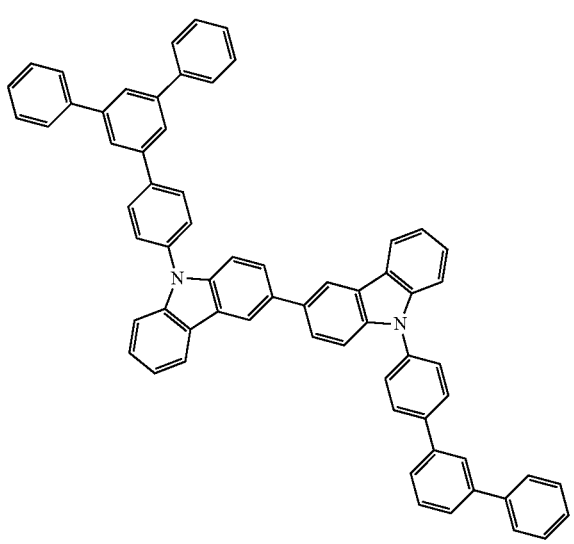
[E-123]
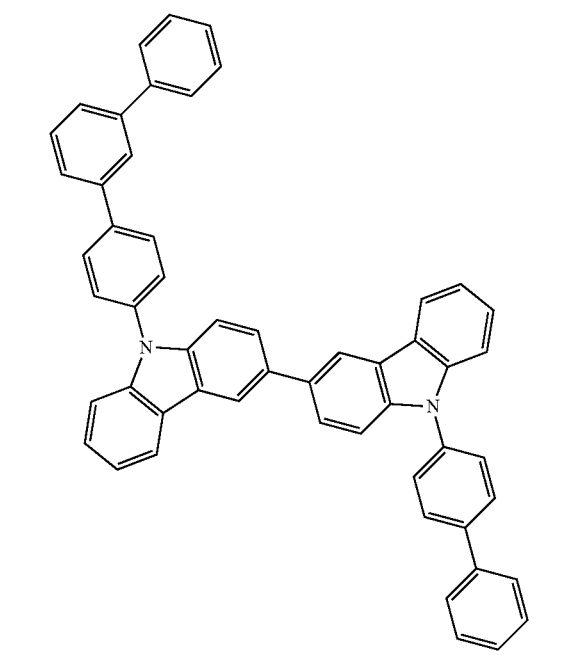
[E-124]
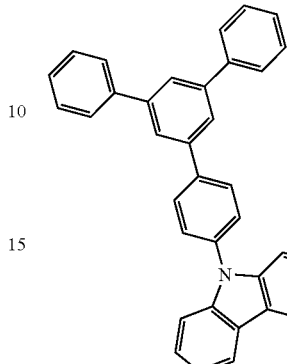
[E-125]
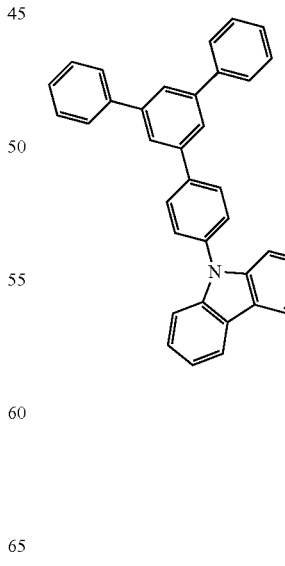

[E-126]
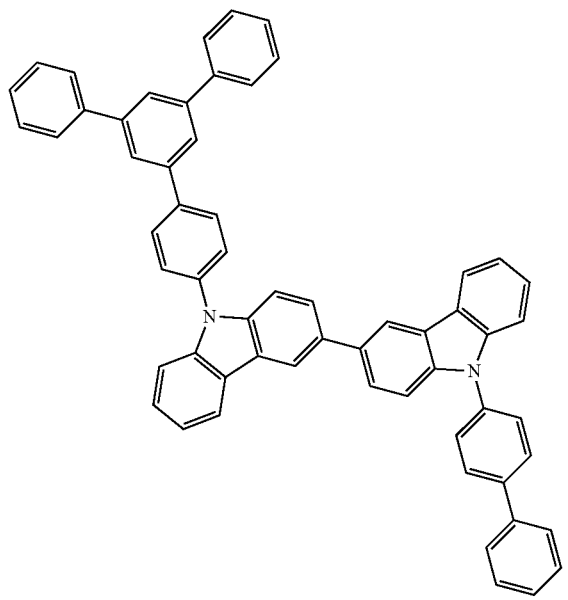
[E-128]
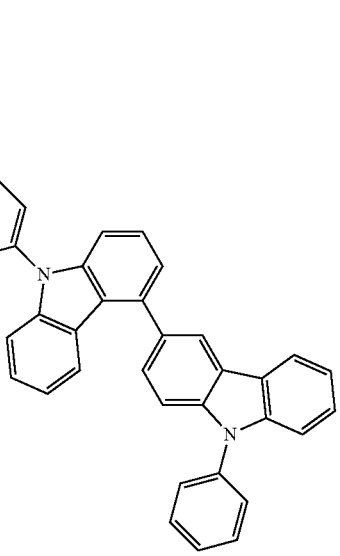
[E-127]
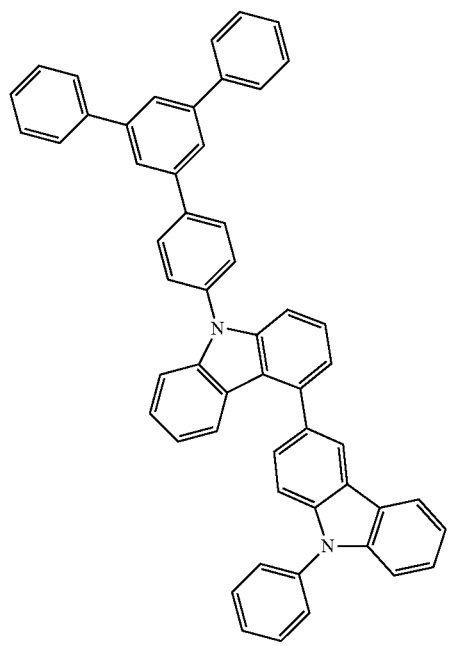
[E-129]
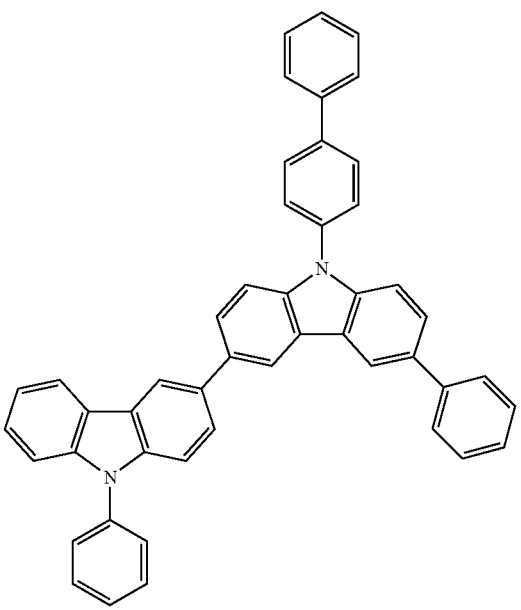

[E-130]
[E-133]
[E-131]
[E-134]
[E-132]
[E-135]
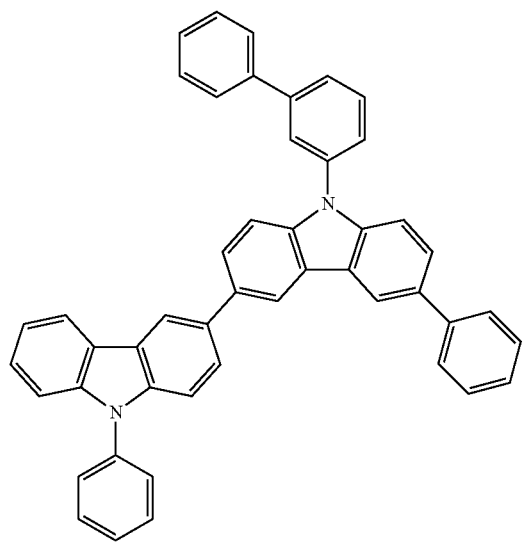
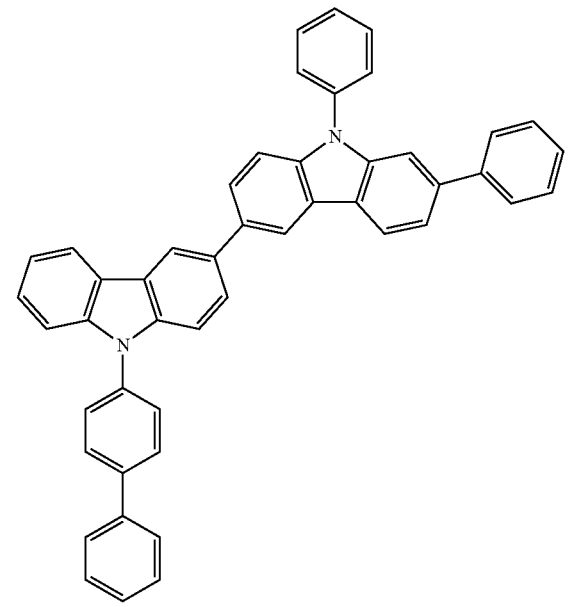
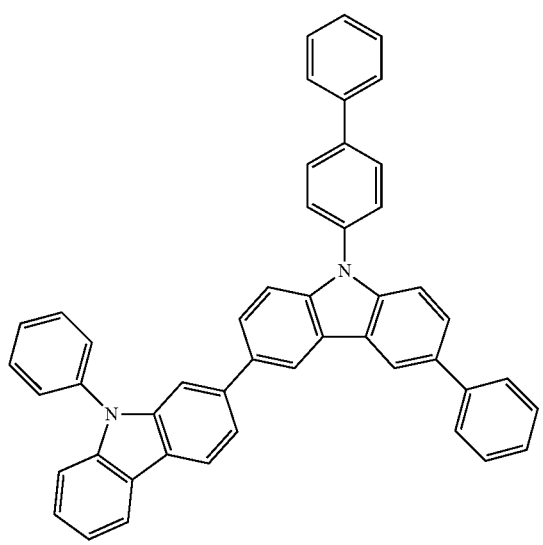
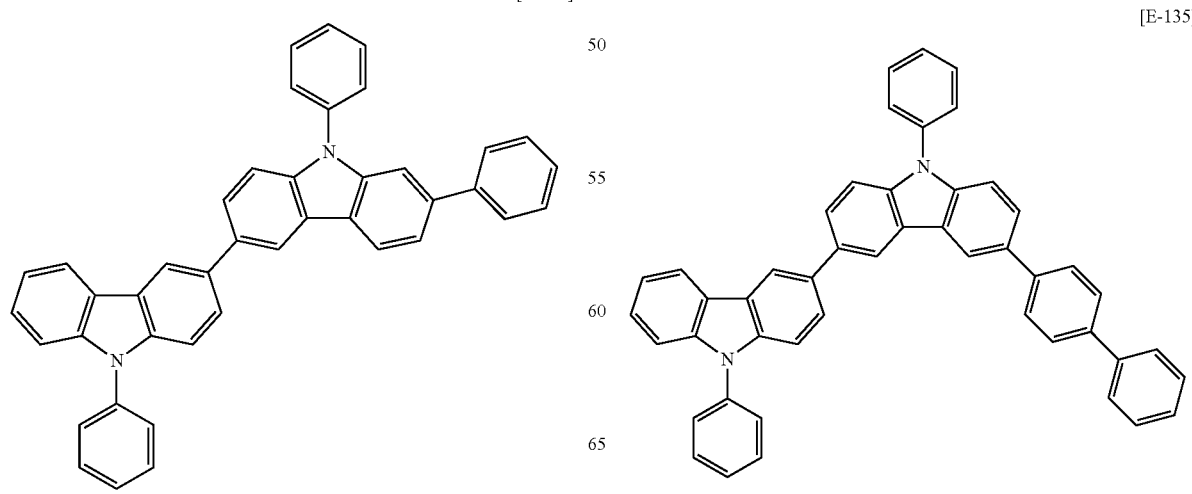

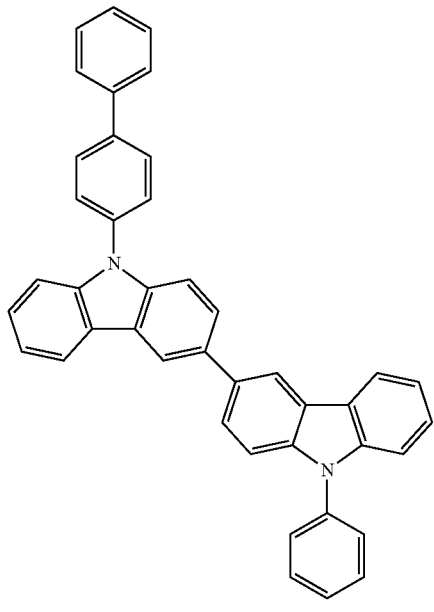

[E-136]

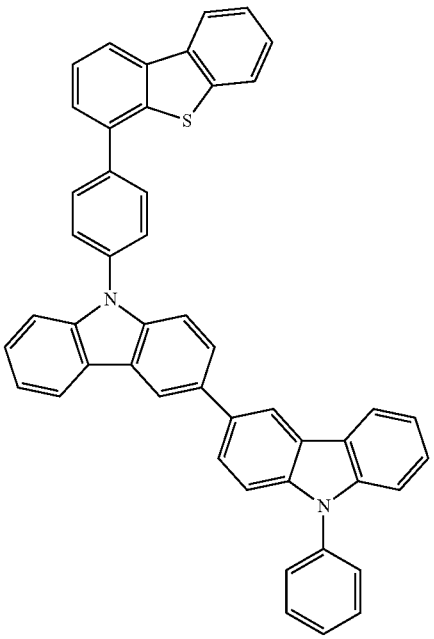

[E-138]

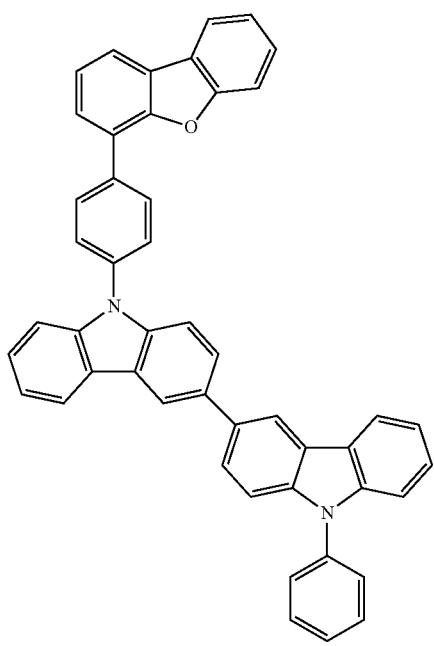

[E-137]

The first host compound and the second host compound may variously be combined to provide various compositions.

A composition according to an example embodiment of the present invention includes a compound represented by Chemical Formula 1-I or Chemical Formula 1-II as a first host, and a compound represented by Chemical Formula C-8 or Chemical Formula C-17 of Group II as a second host.

In addition, a first host represented by Chemical Formula 1-A, or Chemical Formula 1-B and a second host represented by Chemical Formula C-8 or Chemical Formula C-17 of Group II may be included.

A first host represented by Chemical Formula 1-1 and a second host represented by Chemical Formula C-8 or Chemical Formula C-17 of Group II may be included.

For example, *-$L^1$-$Ar^1$ and *-$L^2$-$Ar^2$ of Chemical Formula 2 may be selected from B-1, B-2, B-3, and B-16 of Group III.

The second compound for an organic optoelectronic device is used with the first compound for an organic optoelectronic device in a light-emitting layer, and thereby charge mobility and stability are increased and luminous efficiency and life-span characteristics are improved. In addition, a ratio between the second compound for an organic optoelectronic device and the first compound for an organic optoelectronic device is controlled and thereby charge mobility may be controlled.

For example, the first compound for an organic optoelectronic device and the second compound for an organic optoelectronic device may be included in a weight ratio of about 1:9 to 9:1, specifically 2:8 to 8:2, 3:7 to 7:3, 4:6 to 6:4, or 5:5, and for example the first compound for an organic optoelectronic device and the second compound for an organic optoelectronic device may be included in a weight ratio of 3:7. Within the ranges, efficiency and life-span may be improved simultaneously.

The composition may further include one or more organic compound in addition to the first compound for an organic optoelectronic device and the second compound for an organic optoelectronic device.

The compound for an organic optoelectronic device may further include a dopant. The dopant may be a red, green, or blue dopant.

The dopant is a material in small amount to cause light emission and may be generally a material such as a metal complex that emits light by multiple excitation into a triplet or more. The dopant may be for example an inorganic, organic, or organic/inorganic compound, and one or more kinds thereof may be used.

One example of the dopant may be a phosphorescent dopant and examples of the phosphorescent dopant may be an organometal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be for example, Ir, Pt, Os, Ti, Zr, Hf, Eu, Tb, Tm, Fe, Co, Ni, Ru, Rh, Pd, or a combination thereof and L and X may be for example a bidendate ligand.

Hereinafter, an organic optoelectronic device including the compound for an organic optoelectronic device or the composition for an organic optoelectronic device is described.

An organic optoelectronic device according to another embodiment includes an anode and a cathode facing each other and at least one organic layer disposed between the anode and the cathode, wherein the organic layer includes the compound for an organic optoelectronic device or the composition for an organic optoelectronic device.

For example, the organic layer may include a light-emitting layer and the light-emitting layer may include the compound for an organic optoelectronic device or the composition for an organic optoelectronic device.

Specifically, the compound for an organic optoelectronic device or the composition for an organic optoelectronic device may be included as a green host of the light-emitting layer.

In addition, the organic layer includes a light-emitting layer and at least one auxiliary layer selected from a hole injection layer, a hole transport layer, an electron blocking layer, an electron transport layer, an electron injection layer, and a hole blocking layer and the auxiliary layer may include the compound for an organic optoelectronic device or the composition for an organic optoelectronic device.

The auxiliary layer may further include an electron transport auxiliary layer that is adjacent to the light-emitting layer and the electron transport auxiliary layer may include the compound for an organic optoelectronic device, or the composition for an organic optoelectronic device.

In an example embodiment of the present invention, the compound for an organic optoelectronic device in the electron transport auxiliary layer may be represented by Chemical Formula 1-I, Chemical Formula 1A, or Chemical Formula 1-1.

The organic optoelectronic device may be any device to convert electrical energy into photoenergy and vice versa without particular limitation, and may be, for example an organic photoelectric diode, an organic light emitting diode, an organic solar cell, and an organic photo conductor drum.

Herein, an organic light emitting diode as one example of an organic optoelectronic device is described referring to drawings.

Figure 2:
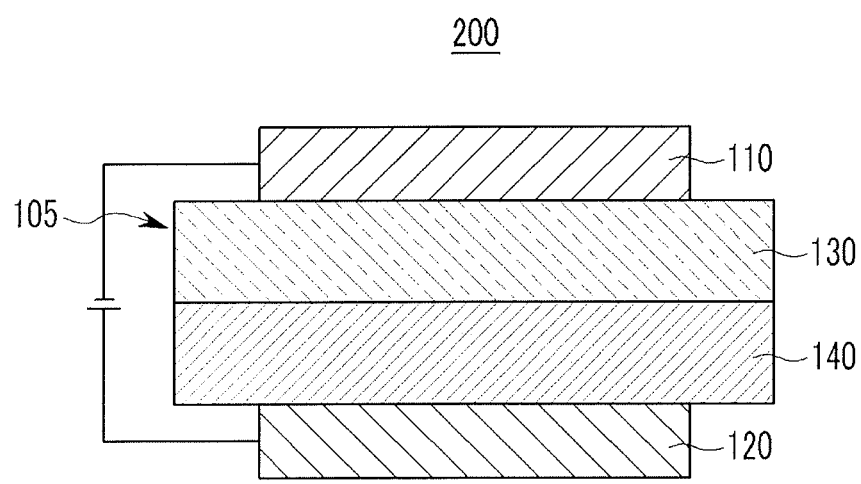

FIGS. 1 and 2 are cross-sectional views showing organic light emitting diodes according to embodiments.

Referring to FIG. 1, an organic light emitting diode 100 according to an embodiment includes an anode 120 and a cathode 110 facing each other and an organic layer 105 between the anode 120 and the cathode 110.

The anode 120 may be made of a conductor having a large work function to help hole injection, and may be for example a metal, a metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal or an alloy thereof such as magnesium, calcium, sodium, potassium, titanium, indium, yttrium, lithium, gadolinium, aluminum, silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes a light-emitting layer 130 including the compound for an organic optoelectronic device.

FIG. 2 is a cross-sectional view of an organic light emitting diode according to another embodiment.

Referring to FIG. 2, an organic light emitting diode 200 further includes a hole auxiliary layer 140 in addition to the light-emitting layer 130. The hole auxiliary layer 140 may further increase hole injection and/or hole mobility and block electrons between the anode 120 and the light-emitting layer 130. The hole auxiliary layer 140 may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound for an organic optoelectronic device of the present invention may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co., Ltd. or TCI Inc. as far as there is no particular comment or were synthesized by known methods.

(Preparation of Compound for Organic Optoelectronic Device)

The compound as one specific examples of the present invention was synthesized through the following steps.

(First Compound for Organic Optoelectronic Device)

Synthesis Example 1: Synthesis of Compound A-1

[Reaction Scheme 1]

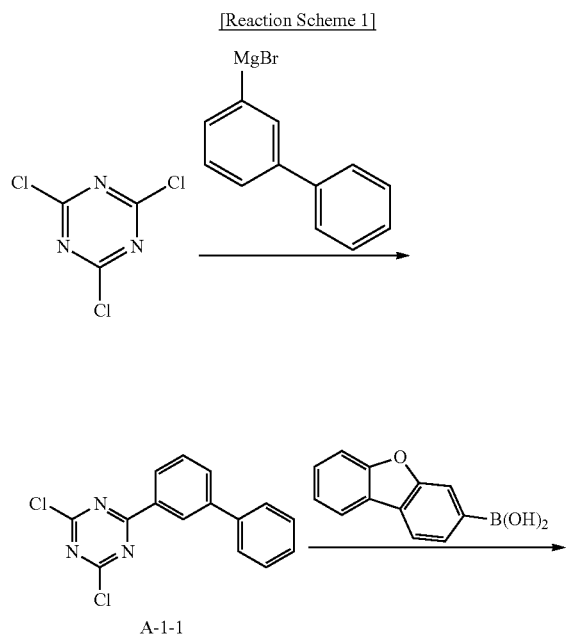

-continued

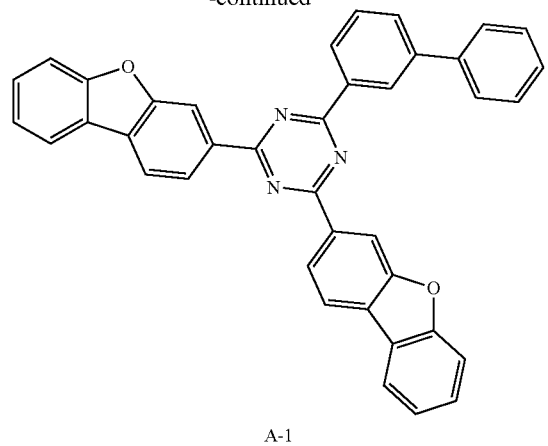

A-1 a) Synthesis of Intermediate A-1-1

Cyanuric chloride (15 g, 81.34 mmol) was dissolved in anhydrous tetrahydrofuran (200 mL) in a 500 mL round-bottomed flask, 1 equivalent of a 3-biphenyl magnesium bromide solution (0.5 M tetrahydrofuran) was added thereto in a dropwise fashion at 0° C. under a nitrogen atmosphere, and the temperature was slowly increased up to room temperature. A reaction solution was stirred at room temperature for 1 hour and then, added to ice water (500 mL) to separate layers. An organic layer was separated therefrom, treated with anhydrous magnesium sulfate, and concentrated. Concentrated residue was recrystallized with tetrahydrofuran and methanol to obtain Intermediate A-1-1 (17.2 g).

b) Synthesis of Compound A-1

Intermediate A-1-1 (17.2 g, 56.9 mmol) was added to tetrahydrofuran (200 mL) and distilled water (100 mL) in a 500 mL round-bottomed flask, 2 equivalents of dibenzofuran-3-boronic acid (cas: 395087-89-5), 0.03 equivalents of tetrakistriphenylphosphine palladium, and 2 equivalents of potassium carbonate were added thereto, and the mixture was heated and refluxed under a nitrogen atmosphere. After 18 hours, a reaction solution was cooled down, and a solid precipitated therein was filtered and washed with water (500 mL). The solid was recrystallized with monochlorobenzene (500 mL) to obtain Compound A-1 (12.87 g).

LC/MS calculated for: C39H23N3O2 Exact Mass: 565.1790 found for: 566.18 [M+H].

Synthesis Example 2: Synthesis of Compound A-2

[Reaction Scheme 2]

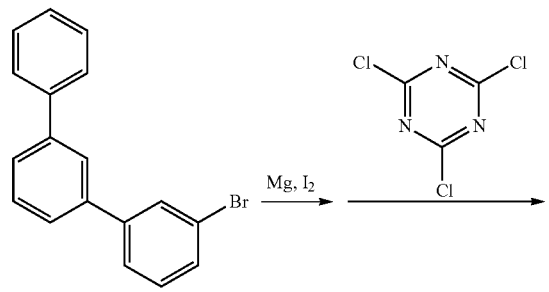

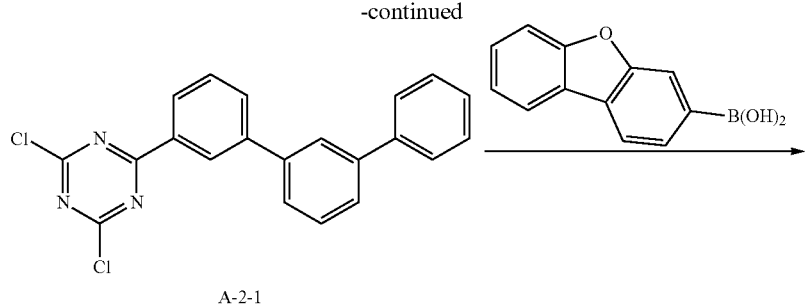

A-2-1

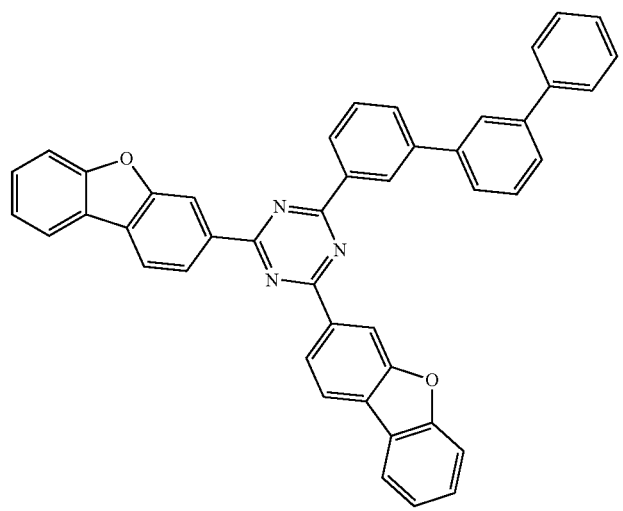

A-2 a) Synthesis of Intermediate A-2-1

Magnesium (7.86 g, 323 mmol) and iodine (1.64 g, 6.46 mmol) were added to tetrahydrofuran (THF, 0.1 L) under a nitrogen environment and mixed therewith for 30 minutes, and 3-bromo-m-terphenyl (100 g, 323 mmol) dissolved in THF (0.3 L) was slowly added thereto in a dropwise fashion at 0° C. for 30 minutes. This mixed solution was slowly added in a dropwise fashion to cyanuric chloride (64.5 g, 350 mmol) dissolved in THF (0.5 L) at 0° C. over 30 minutes. After the reaction was complete, water was added to the reaction solution, the mixture was extracted with dichloromethane (DCM) and treated with anhydrous MgSO$_4$ to remove moisture, and the resultant was filtered and concentrated under a reduced pressure. The obtained residue was separated and purified through flash column chromatography to obtain Intermediate A-2-1 (85.5 g, 70%).

b) Synthesis of Compound A-2

Compound A-2 was synthesized according to the same method as b) of Synthesis Example 1 by using Intermediate A-2-1.

LC/MS calculated for: C45H27N3O2 Exact Mass: 641.2103 found for 642.21 [M+H].

Synthesis Example 3: Synthesis of Compound A-5

[Reaction Scheme 3]

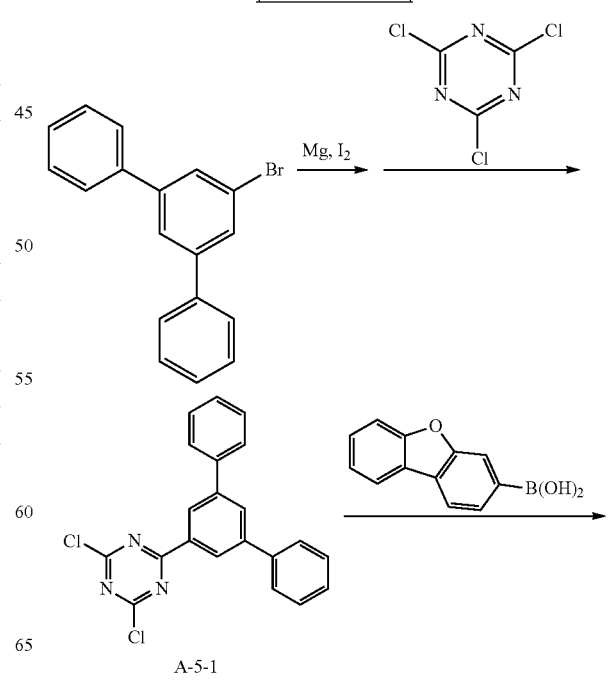

A-5-1

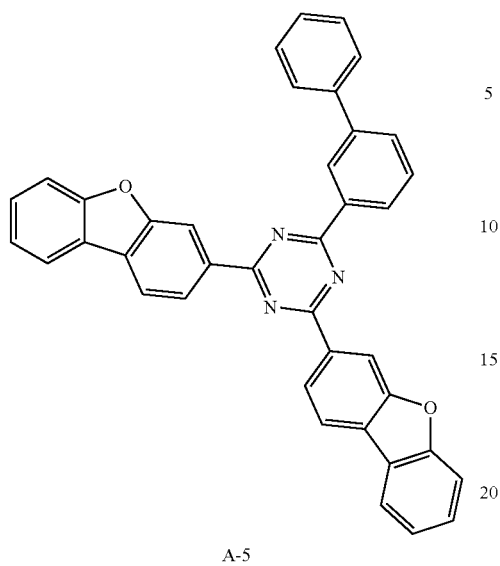

A-5

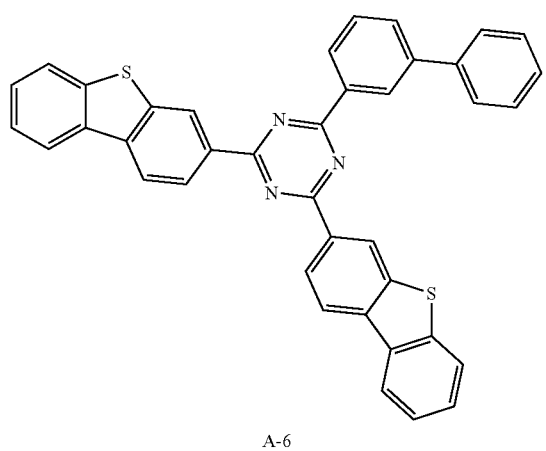

A-6 a) Synthesis of Intermediate A-5-1

Magnesium (7.86 g, 323 mmol) and iodine (1.64 g, 6.46 mmol) were added to tetrahydrofuran (THF, 0.1 L) and stirred therewith for 30 minutes under a nitrogen environment, and 1-bromo-3,5-diphenylbenzene (100 g, 323 mmol) dissolved in THF (0.3 L) was slowly added thereto in a dropwise fashion at 0° C. for 30 minutes. This mixed solution was slowly added in a dropwise fashion to cyanuric chloride (64.5 g, 350 mmol) dissolved in THF (0.5 L) at 0° C. for 30 minutes. After the reaction was complete, water was added to the reaction solution, the mixture was extracted with dichloromethane (DCM) and treated with anhydrous MgSO$_4$ to remove moisture, and the resultant was filtered and concentrated under a reduced pressure. The obtained residue was separated and purified through flash column chromatography to obtain Intermediate A-5-1 (79.4 g, 65%).

b) Synthesis of Compound A-5

Compound A-5 was synthesized according to the same method as b) of Synthesis Example 1 by using Intermediate A-5-1.

LC/MS calculated for: C45H27N3O2 Exact Mass: 641.2103 found for 642.21 [M+H].

Synthesis Example 4: Synthesis of Compound A-6 a) Synthesis of Compound A-6

Compound A-6 was synthesized according to the same method as b) of Synthesis Example 1 by using dibenzothiophene-3-boronic acid (Cas No.: 108847-24-1) instead of Intermediate A-1-1 and dibenzofuran-3-boronic acid (Cas No.: 395087-89-5).

LC/MS calculated for: C39H23N3S2 Exact Mass: 597.1333 found for 598.13 [M+H].

Synthesis Example 5: Synthesis of Compound A-15

[Reaction Scheme 5]

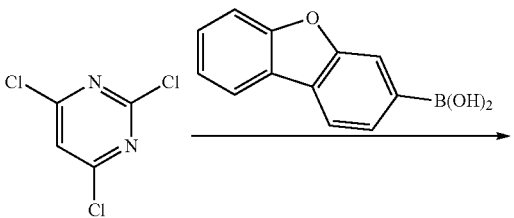

[Reaction Scheme 4]

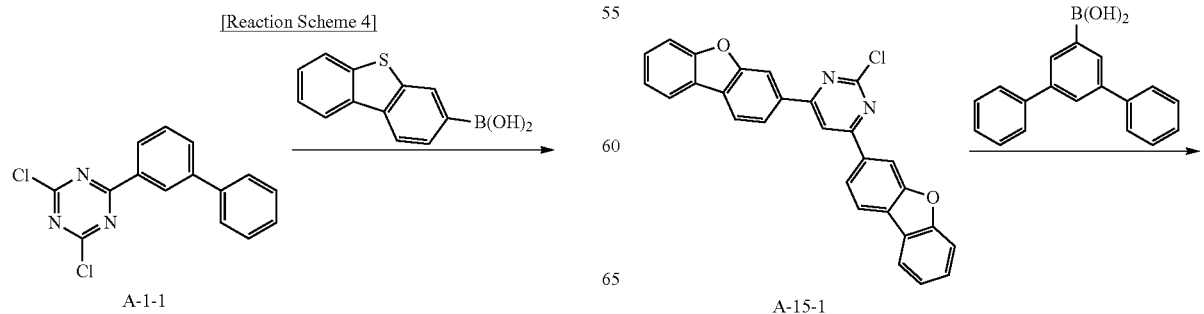

A-1-1

A-15-1

-continued

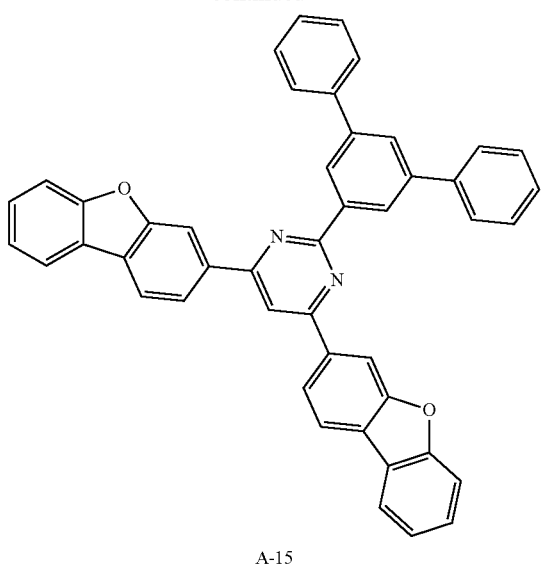

A-15 a) Synthesis of Intermediate A-15-1

2,4,6-trichloropyrimidine (18.3 g, 100 mmol) was added to tetrahydrofuran (200 mL) and distilled water (100 mL) in a 500 mL round-bottomed flask, 1.9 equivalents of dibenzofuran-3-boronic acid (Cas No.: 395087-89-5), 0.03 equivalents of tetrakistriphenylphosphine palladium, and 2 equivalents of potassium carbonate were added thereto, and the mixture was heated and refluxed under a nitrogen atmosphere. After 18 hours, the reaction solution was cooled down, and a solid precipitated therein was filtered and washed with water (500 mL). The solid was recrystallized with monochlorobenzene (500 mL) to obtain Intermediate A-15-1 (26.8 g, a yield of 60%).

b) Synthesis of Compound A-15

Compound A-15 was synthesized according to the same method as b) of Synthesis Example 1 by using Intermediate A-15-1 and 1.1 equivalents of 3,5-diphenylbenzene boronic acid.

LC/MS calculated for: C46H28N2O2 Exact Mass: 640.2151 found for 641.21 [M+H].

Synthesis Example 6: Synthesis of Compound A-21

[Reaction Scheme 6]

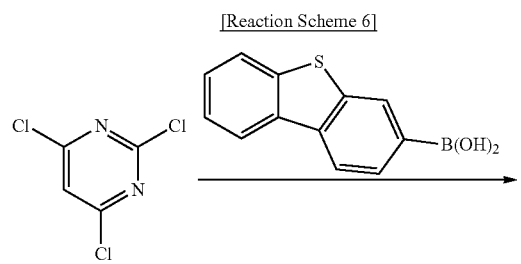

-continued

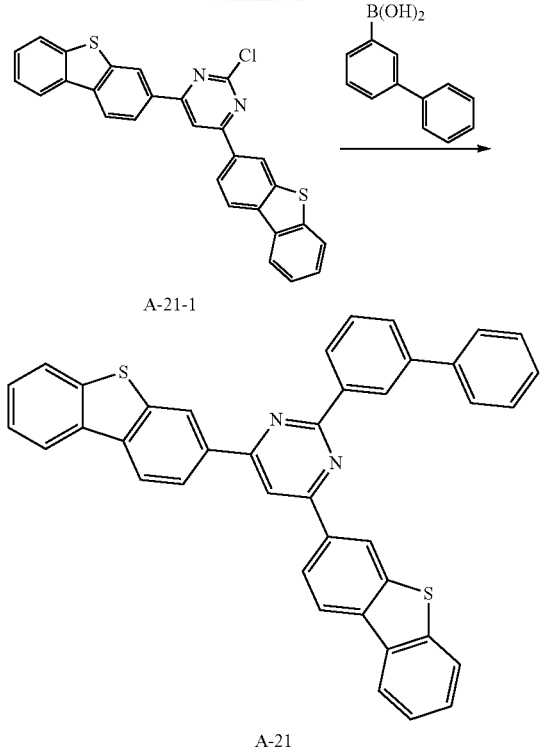

A-21 a) Synthesis of Intermediate A-21-1

Intermediate A-21-1 was synthesized according to the same method as a) of Synthesis Example 5 by using the dibenzothiophene-3-boronic acid (Cas No. 108847-24-1) instead of the dibenzofuran-3-boronic acid (cas: 395087-89-5).

b) Synthesis of Compound A-21

Compound A-21 was synthesized according to the same method as b) of Synthesis Example 5 by using Intermediate A-21-1 and 1.1 equivalents of biphenyl-3-boronic acid.

LC/MS calculated for: C40H24N2S2 Exact Mass: 596.1381 found for 597.14 [M+H].

Synthesis of Second Compound for Organic Optoelectronic Device

Synthesis Example 7: Synthesis of Compound E-130

[Reaction Scheme 7]

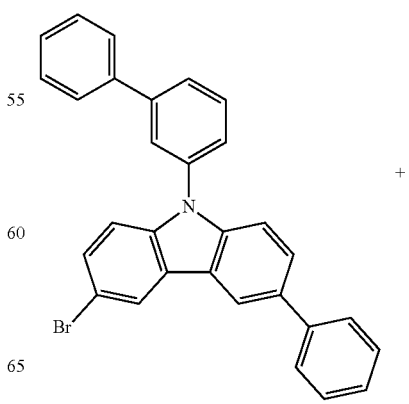

+

-continued

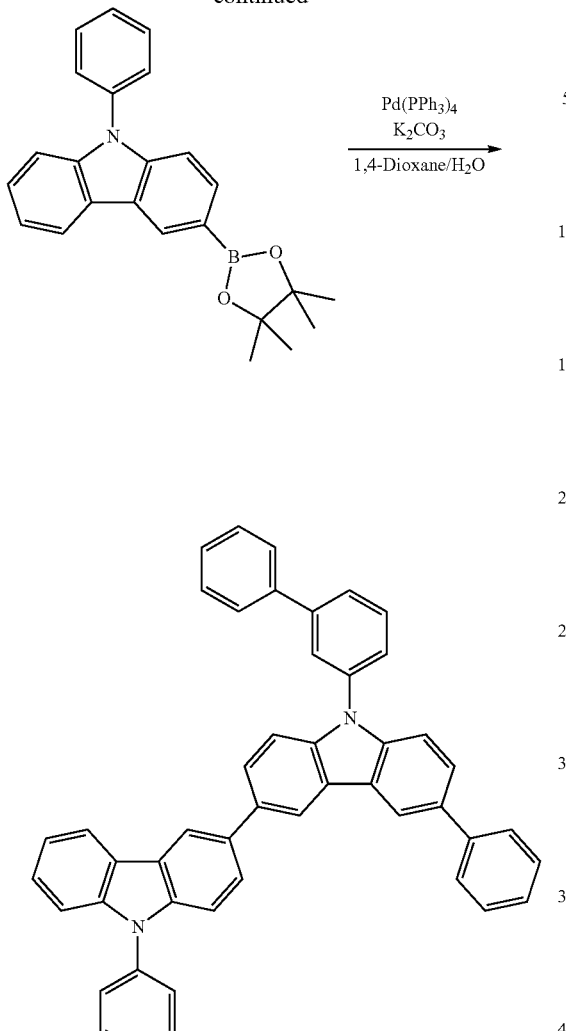

Compound E-130

Synthesis Example 8: Synthesis of Compound E-137

[Reaction Scheme 8]

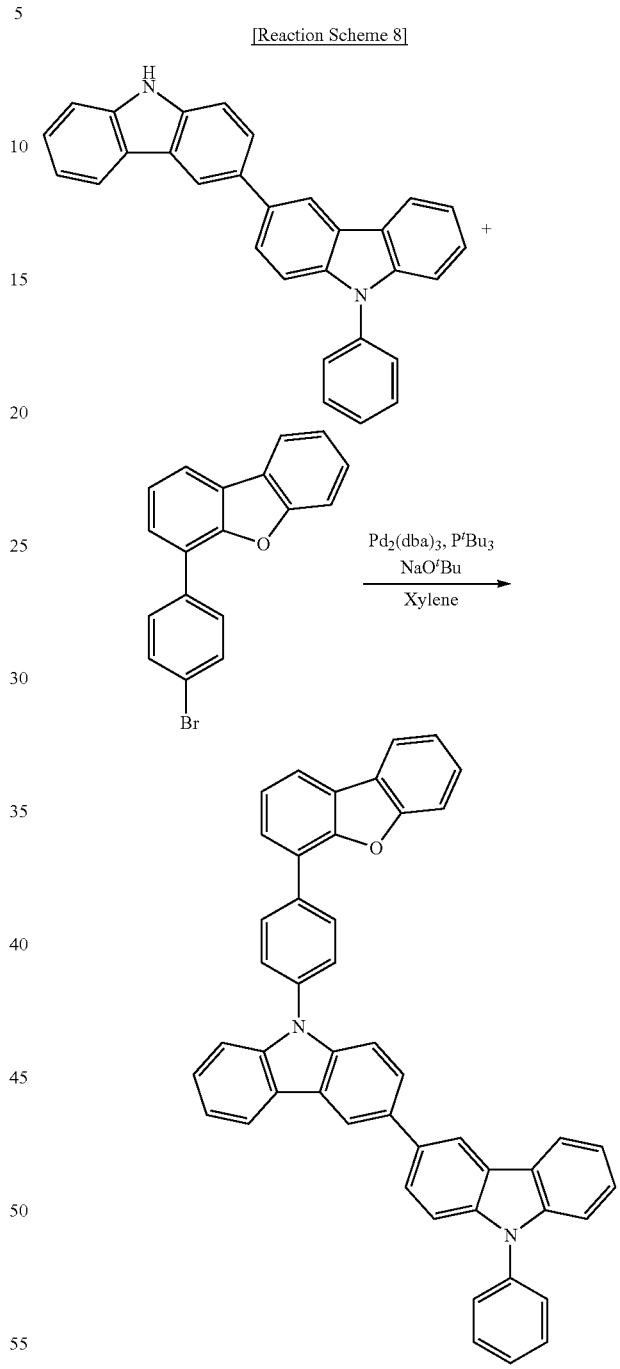

3-bromo-6-phenyl-N-metabiphenylcarbazole (20.00 g, 42.16 mmol) and N-phenylcarbazole-3-boronic ester (17.12 g, 46.38 mmol) were mixed with a mixture of tetrahydrofuran:toluene (1:1, 175 mL) and a 2 M-potassium carbonate aqueous solution (75 mL) under a nitrogen atmosphere in a 500 mL round-bottomed flask equipped with an agitator, tetrakistriphenylphosphinepalladium (0) (1.46 g, 1.26 mmol) was added thereto, and the obtained mixture was heated and refluxed under a nitrogen flow for 12 hours. When the reaction was complete, the reactant was poured into methanol, and a solid produced therein was filtered, sufficiently washed with water and methanol, and dried. The resulting material was dissolved in chlorobenzene (700 mL) through heating, the solution was silica gel-filtered, and after completely removing a solvent therefrom, a solid obtained therefrom was dissolved in chlorobenzene (400 mL) through heating and recrystallized to obtain Compound E-130 (18.52 g, a yield of 69%).

calcd. $C_{42}H_{32}N_2$: C, 90.54; H, 5.07; N, 4.40; found: C, 90.54; H, 5.07; N, 4.40.

N-phenyl-3,3-bicarbazole (6.3 g, 15.4 mmol), 4-(4-bromophenyl)dibenzo[b,d]furan (5.0 g, 15.4 mmol), sodium t-butoxide (3.0 g, 30.7 mmol), tris(dibenzylideneacetone)dipalladium (0.9 g, 1.5 mmol), and tri t-butylphosphine (1.2 mL, 50% in toluene) were mixed with xylene (100 mL) in a 250 mL round flask, and the mixture was heated and refluxed under a nitrogen flow for 15 hours. The obtained mixture was added to methanol (300 mL), and a solid crystallized therein was dissolved in dichlorobenzene, filtered with silica gel/Celite, and after removing an appropriate amount of an organic solvent, recrystallized with methanol to obtain Compound E-137 (7.3 g, a yield of 73%).

calcd. C48H30N2O: C, 88.59; H, 4.65; N, 4.30; O, 2.46; found: C, 88.56; H, 4.62; N, 4.20; O, 2.43.

Comparative Synthesis Example 1: Synthesis of Comparative Compound 1

[Reaction Scheme 9]

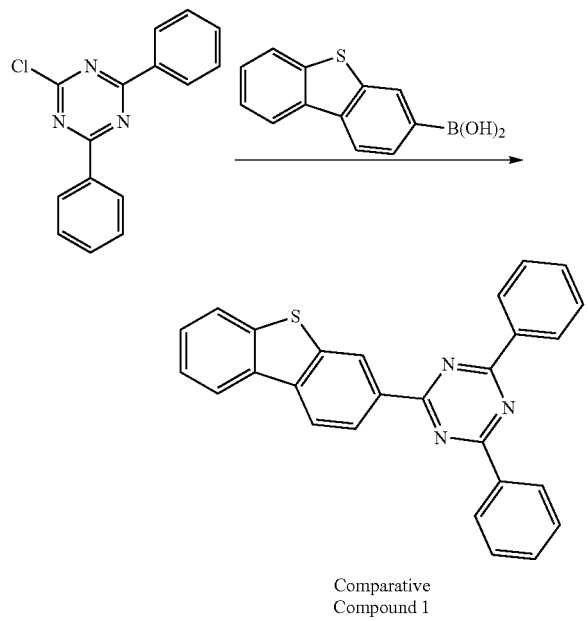

Comparative Compound 1 a) Synthesis of Comparative Compound 1

Comparative Compound 1 was synthesized according to the same method as b) of Synthesis Example 1 by using 2-chloro-4,6-diphenyltriazine and dibenzothiophene-3-boronic acid.

LC/MS calculated for: C27H17N3S Exact Mass: 415.1143 found for 416.11 [M+H].

Comparative Synthesis Example 2: Synthesis of Comparative Compound 2

[Reaction Scheme 10]

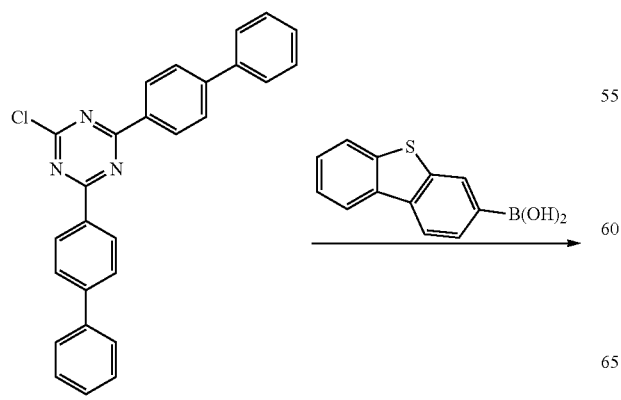

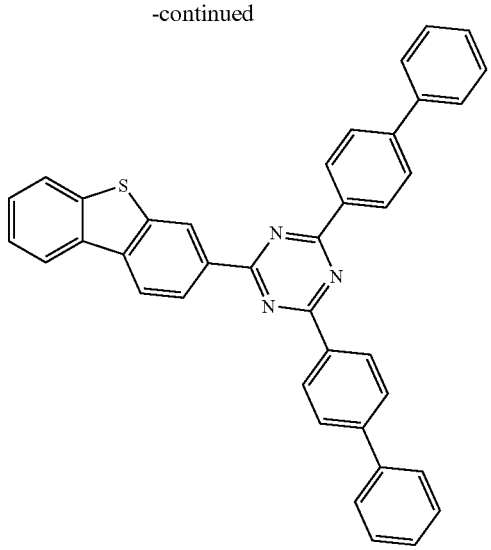

Comparative Compound 2 a) Synthesis of Comparative Compound 2

Comparative Compound 2 was synthesized according to the same method as b) of Synthesis Example 1 by using 2,4-bis([1,1'-biphenyl]-4-yl)-6-chloro-1,3,5-triazine and dibenzothiophene-3-boronic acid.

LC/MS calculated for: C39H25N3S Exact Mass: 567.1769 found for 568.18 [M+H].

Comparative Synthesis Example 3: Synthesis of Comparative Compound 3

[Reaction Scheme 11]

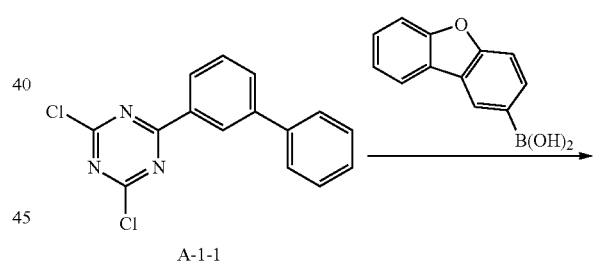

A-1-1

Comparative Compound 3 a) Synthesis of Comparative Compound 3

Comparative Compound 3 was synthesized according to the same method as b) of Synthesis Example 1 by using Intermediate A-1-1 and dibenzofuran-2-boronic acid.

LC/MS calculated for: C39H23N3O Exact Mass: 565.1790 found for 566.18 [M+H].

Comparative Synthesis Example 4: Synthesis of Comparative Compound 4

[Reaction Scheme 12]

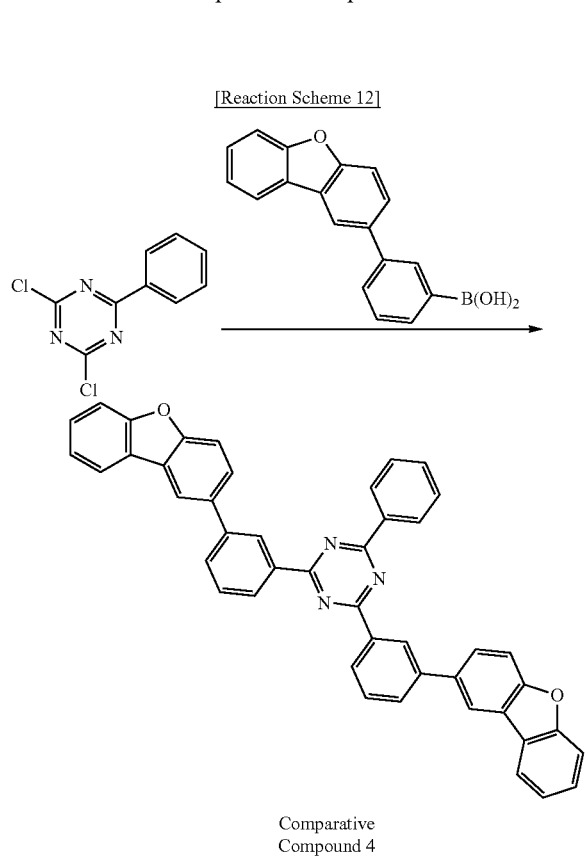

Comparative Compound 4 a) Synthesis of Comparative Compound 4

Comparative Compound 4 was synthesized according to the same method as b) of Synthesis Example 1 by using 2,4-dichloro-6-phenyl-1,3,5-triazine and dibenzofuran-2-yl-3-phenylboronic acid.

LC/MS calculated for: C39H23N3O Exact Mass: 565.1790 found for 566.18 [M+H].

Comparative Synthesis Example 5: Synthesis of Comparative Compound 5

[Reaction Scheme 13]

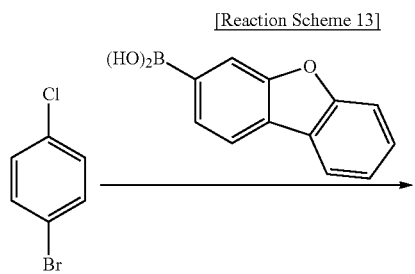

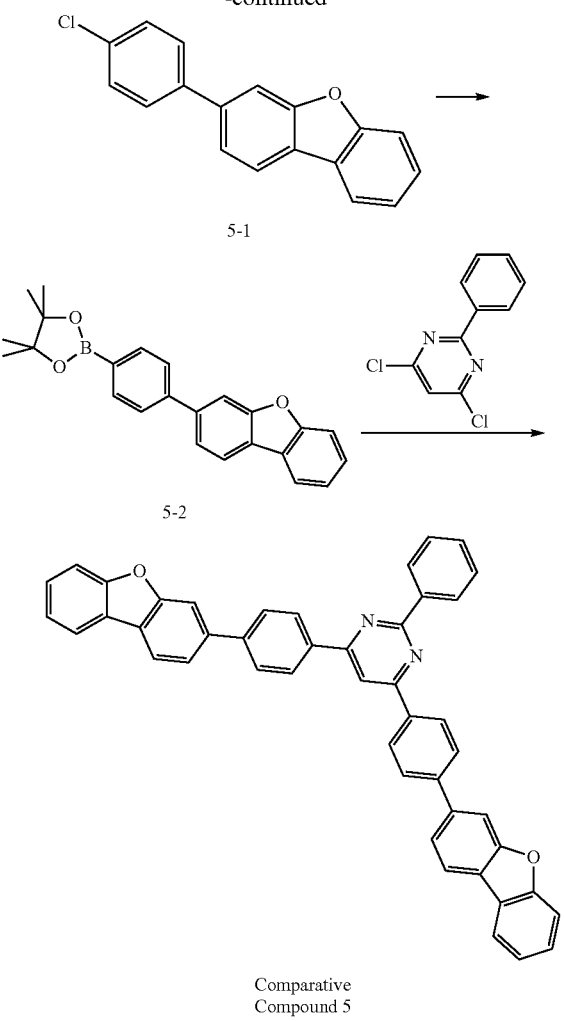

Comparative Compound 5 a) Synthesis of Intermediate 5-1

Intermediate 5-1 was synthesized according to the same method as b) of Synthesis Example 1 by using 1-bromo-4-chlorobenzene and dibenzofuran-3-boronic acid.

b) Synthesis of Intermediate 5-2

Intermediate 5-1 (328 mmol) was dissolved in dimethylformamide (DMF, 1.0 L), bis(pinacolato)diboron (100 g, 394 mmol), (1,1'-bis(diphenylphosphine)ferrocene)dichloropalladium (II) (2.68 g, 3.28 mmol), and potassium acetate (96.6 g, 984 mmol) were added thereto, and the mixture was heated and refluxed at 150° C. for 20 hours. After the reaction was complete, water was added to the reaction solution and the mixture was filtered and dried in a vacuum oven. The obtained residue was separated and purified through flash column chromatography to obtain Intermediate 5-2 (71%).

c) Synthesis of Comparative Compound 5

Comparative Compound 5 was synthesized according to the same method as b) of Synthesis Example 1 by using Intermediate 5-2 and 4,6-dichloro-2-phenyl-1,3-pyrimidine.

LC/MS calculated for: C46H28N2O2 Exact Mass: 640.2151 found for 641.22 [M+H].

Manufacture of Organic Light Emitting Diode

Example 1

A glass substrate coated with ITO (indium tin oxide) as a 1500 Å-thick thin film was washed with distilled water. After washed with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. A 400 Å-thick light-emitting layer was formed on the hole transport layer by vacuum-depositing Compound A-1 of Synthesis Example 1 and Compound E-130 of Synthesis Example 7 simultaneously as a host and 10 wt % of tris(2-phenylpyridine)iridium(III) [Ir(ppy)$_3$] as a dopant. Herein, Compound A-1 and Compound E-130 were used at a weight ratio of 3:7 and in the following examples, a ratio is separately described. Subsequently, Compound D and Liq were vacuum-deposited simultaneously at a 1:1 ratio on the light-emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer, and specifically
ITO/Compound A (700 Å)/Compound B (50 Å)/Compound C (1020 Å)/EML [Compound A-1:E-130:Ir(ppy)$_3$=27 wt %:63 wt %:10 wt %] (400 Å)/Compound D:Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline

Example 2

An organic light emitting diode according to Example 2 was manufactured according to the same method as Example 1 by using Compound A-2 alone.

Examples 3 to 10

Organic light emitting diodes according to Examples 3 to 10 were manufactured according to the same method as Example 1 by using first and second hosts of the present invention as shown in Tables 2 and 3.

Comparative Examples 1 and 2

Organic light emitting diodes according to Comparative Examples 1 and 2 were manufactured according to the same method as Example 1 by using Comparative Compound 1 and Comparative Compound 2 respectively alone.

Comparative Examples 3 to 7

Organic light emitting diodes according to Comparative Examples 3 to 7 were manufactured according to the same method as Example 1 by using either one of Comparative Compound 1 to Comparative Compound 5 with Compound E-31 with a ratio of 3:7 as shown in Tables 2 and 3.

Evaluation 1: Luminous Efficiency and Life-Span Improvement Effects

Luminous efficiency and life-span characteristics of each organic light emitting diode according to Examples 1 to 10 and Comparative Examples 1 to 7 were measured. Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and, the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

T90 life-spans of the organic light emitting diodes according to Examples 1 to 10 and Comparative Examples 1 to 7 were measured as a time when their luminance decreased down to 90% relative to the initial luminance (cd/m$^2$) after emitting light with cd/m$^2$ as the initial luminance (cd/m$^2$) and measuring their luminance decreases depending on a time with a Polanonix life-span measurement system.

TABLE 1

Single Host Device

| | First host | Color | Efficiency (Cd/A) | Life-span (T90) |
|---|---|---|---|---|
| Example 2 | Compound A-2 | green | 39 | 140 |
| Comparative Example 1 | Comparative Compound 1 | green | 32 | 60 |
| Comparative Example 2 | Comparative Compound 2 | green | 33 | 40 |

Referring to Table 1, comparing Examples and Comparative Examples 1 and 2 in case of using a single host, Examples having a structural feature of additionally including a meta-substituted aryl group showed greater than or equal to 1.2 times higher efficiency and at most greater than or equal to 4 times longer life-span than Comparative Examples despite dibenzofuran linked with triazine at the same position No. 3.

TABLE 2

Mixed Host Device Effect: Triazine

| | First host | Second host | First host + Second host ratio | Color | Efficiency Cd/A | Life-span (T90) |
|---|---|---|---|---|---|---|
| Example 1 | Compound A-1 | Compound E-130 | 3:7 | green | 51 | 460 |
| Example 3 | Compound A-2 | Compound E-130 | 3:7 | green | 52 | 530 |

TABLE 2-continued

Mixed Host Device Effect: Triazine

|  | First host | Second host | First host + Second host ratio | Color | Efficiency Cd/A | Life-span (T90) |
|---|---|---|---|---|---|---|
| Example 4 | Compound A-2 | Compound E-99 | 3:7 | green | 50 | 600 |
| Example 5 | Compound A-2 | Compound E-31 | 3:7 | green | 51 | 650 |
| Example 6 | Compound A-2 | Compound E-137 | 3:7 | green | 50 | 570 |
| Example 7 | Compound A-5 | Compound E-31 | 3:7 | green | 51 | 600 |
| Example 8 | Compound A-6 | Compound E-31 | 3:7 | green | 49 | 480 |
| Comparative Example 3 | Comparative Compound 1 | Compound E-31 | 3:7 | green | 48 | 160 |
| Comparative Example 4 | Comparative Compound 2 | Compound E-31 | 3:7 | green | 46 | 240 |
| Comparative Example 5 | Comparative Compound 3 | Compound E-31 | 3:7 | green | 46 | 130 |
| Comparative Example 6 | Comparative Compound 4 | Compound E-31 | 3:7 | green | 50 | 290 |

TABLE 3

Mixed Host Device Effect: Pyrimidine

|  | First host | Second host | First host + Second host ratio | Color | Efficiency Cd/A | Life-span (T90) |
|---|---|---|---|---|---|---|
| Example 9 | Compound A-15 | Compound E-31 | 3:7 | green | 52 | 340 |
| Example 10 | Compound A-21 | Compound E-31 | 3:7 | green | 53 | 380 |
| Comparative Example 7 | Comparative Compound 5 | Compound E-31 | 3:7 | green | 46 | 150 |

Referring to Tables 2 and 3, Examples using first and second hosts according to the present invention and having a structural feature of having dibenzofuran linked with triazine at the position No. 3 and/or additionally including a meta-substituted aryl group showed at most 5 times longer life-span than Comparative Example using a mixed host with the same second host.

This life-span increase effect was equally obtained in the pyrimidine core as well as the triazine core. Accordingly, referring to corresponding device data, a life-span of a corresponding material in a device turned out to be improved through effects of a LUMO expansion and a cyclic fusion, when dibenzofuran or dibenzothiophene is directly linked with an ET core group.

Evaluation 2: Driving Voltage Decrease Effect

[Measurement of Driving Voltage]

A driving voltage of each device was measured at 15 mA/cm$^2$ by using a current-voltage meter (Keithley 2400), and the results are shown in Table 4.

TABLE 4

|  | First host | Second host | First host + Second host ratio | Color | Vd |
|---|---|---|---|---|---|
| Example 4 | Compound A-2 | Compound E-99 | 3:7 | green | 3.75 |
| Example 5 | Compound A-2 | Compound E-31 | 3:7 | green | 3.90 |
| Example 8 | Compound A-6 | Compound E-31 | 3:7 | green | 3.85 |
| Comparative Example 5 | Comparative Compound 3 | Compound E-137 | 3:7 | green | 4.20 |
| Comparative Example 6 | Comparative Compound 4 | Compound E-137 | 3:7 | green | 4.40 |

Referring to Table 4, comparing Examples 4, 5, and 8 using a host combination according to the present invention with Comparative Examples 5 and 6, an excellent effect in terms of a driving voltage was obtained, when the position No. 3 of dibenzofuran or dibenzothiophene is directly substituted and liked with triazine compared with when other positions of dibenzofuran or dibenzothiophene were substituted and linked with triazine even though the aryl linker at a meta position was included and when the dibenzofuran or dibenzothiophene was substituted not directly but through the aryl linker and linked with triazine. Accordingly, the direct substitution of the position No. 3 of the dibenzofuran or dibenzothiophene turned out to bring about an excellent effect in terms of driving.

Example 11 (Electron Transport Auxiliary Layer)

ITO (indium tin oxide) was coated to be 1500 Å thick on a glass substrate, and the coated glass substrate was ultrasonic wave-washed with a distilled water. After the washing with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, a 700 Å-thick hole injection layer was formed on the ITO substrate by vacuum-depositing Compound A, and a hole transport layer was formed on the injection layer by depositing Compound B to be 50 Å thick and Compound C to be 1020 Å thick. Then, a 200 Å-thick light-emitting layer was formed thereon by vacuum-depositing BH113 and BD370 (Manufacturer: SFC Inc.) as a blue fluorescent luminescent host and a dopant in a dopant concentration of 5 wt %. On the light-emitting layer, Compound A-5 was vacuum-deposited to form a 50 Å-thick electron transport auxiliary layer. The electron transport auxiliary layer may be formed by using a material represented by Chemical Formula I alone or mixing the material with the compound of Group E. On the electron transport auxiliary layer, a 300 Å-thick electron transport layer was formed by vacuum-depositing Compound D and Liq simultaneously in a weight ratio of 1:1, and on the electron transport layer, a cathode was formed by sequentially vacuum-depositing Liq to be 15 Å thick and Al to be 1200 Å thick, manufacturing an organic light emitting diode. The organic light emitting diode had a structure of 5 organic thin film layers and specifically, ITO/Compound A (700 Å)/Compound B (50 Å)/Compound C (1020 Å)/EML [BH113:BD370=95:5 (wt:wt)] (200 Å)/Compound A-5 (50 Å)/Compound D:Liq (300 Å)=1:1/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline

Example 12

An organic light emitting diode was manufactured according to the same method as Example 11 except for using Compound A-15.

Comparative Example 8

An organic light emitting diode was manufactured according to the same method as Example 11 except for using Comparative Compound 1.
Evaluation 3

Current density change, luminance change, and luminous efficiency depending on a voltage of each organic light emitting diode according to Examples 11 and 12 and Comparative Example 8 were measured.

Specific measurement methods are the same as in Evaluation 1, a method of measuring life-span is as follows, and the results are shown in Table 5.

[Measurement of Life-Span]

T97 life-spans of the organic light emitting diodes according to Example 11, Example 12, and Comparative Example 8 were measured as a time when their luminance decreased down to 97% relative to the initial luminance (cd/m$^2$) after emitting light with 750 cd/m$^2$ as the initial luminance (cd/m$^2$) and measuring their luminance decrease depending on a time with a Polanonix life-span measurement system.

TABLE 5

| Devices | Electron transport auxiliary layer (weight ratio) | Luminous efficiency (cd/A) | Color coordinate (x, y) | T97 (h) @750 nit |
|---|---|---|---|---|
| Example 11 | compound A-5 | 6.7 | (0.132, 0.149) | 85 |
| Example 12 | compound A-15 | 7.1 | (0.133, 0.148) | 70 |
| Comparative Example 8 | Comparative Compound 1 | 5.9 | (0.132, 0.149) | 48 |

Referring to Table 5, the organic light emitting diodes according to Examples 11 and 12 showed simultaneously improved luminous efficiency and life-span characteristics compared with the organic light emitting diode according to Comparative Example 8.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound for an organic optoelectronic device, the compound being represented by Chemical Formula 1:

[Chemical Formula 1]

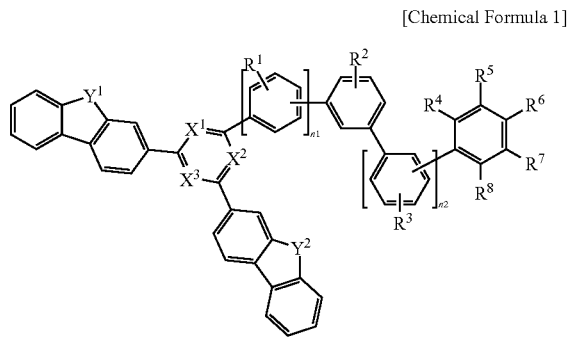

wherein, in Chemical Formula 1,
$X^1$ to $X^3$ are independently N or $CR^a$,
at least two of $X^1$ to $X^3$ are N,
$Y^1$ and $Y^2$ are independently O or S,
n1 and n2 are independently an integer of 0 or 1,
$R^1$ to $R^3$ are independently hydrogen, deuterium, a phenyl group, a biphenyl group, or a naphthyl group, and
$R^a$ and $R^4$ to $R^8$ are independently hydrogen or deuterium.

2. The compound for an organic optoelectronic device of claim 1, wherein the compound is represented by Chemical Formula 1-I, Chemical Formula 1-II, or Chemical Formula 1-III:

[Chemical Formula 1-I]

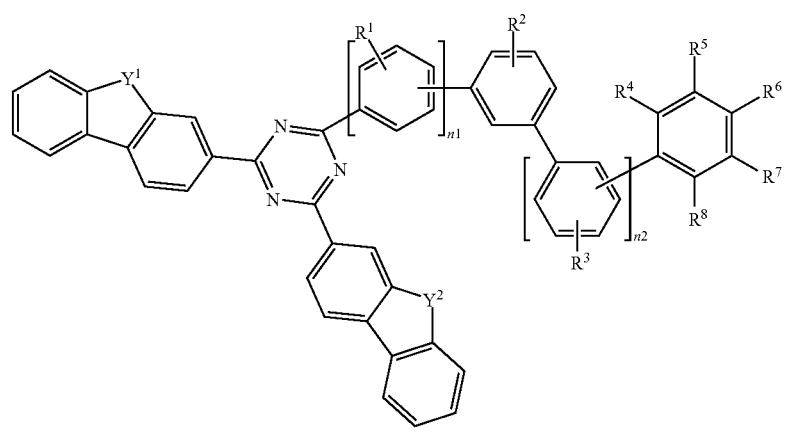

-continued

[Chemical Formula 1-II]

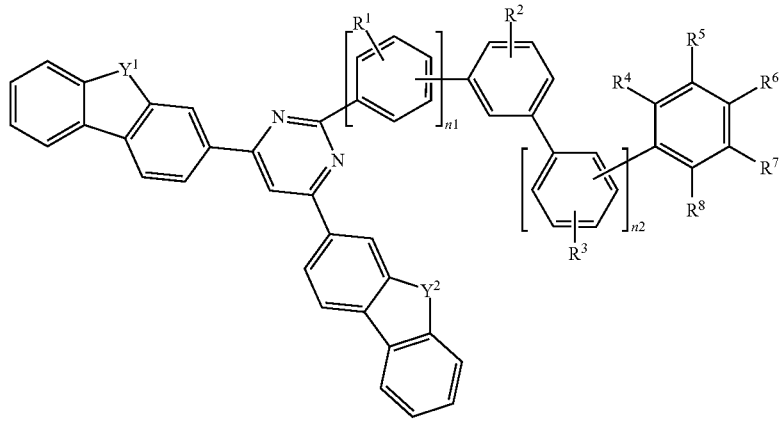

[Chemical Formula 1-III]

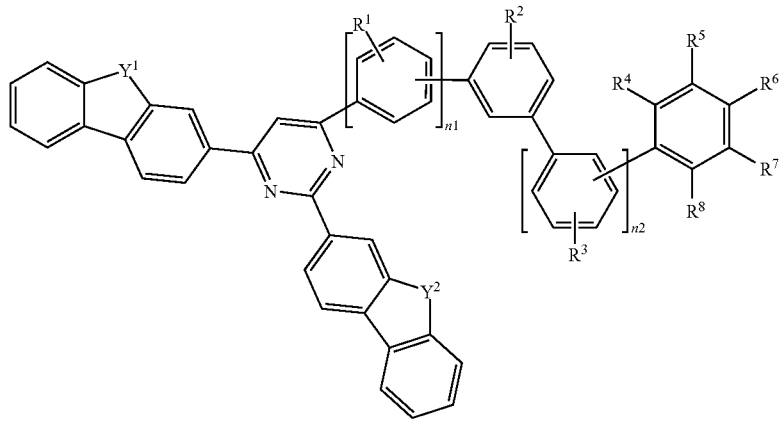

wherein, in Chemical Formula 1-1 Chemical Formula 1-II, and Chemical Formula 1-II,
$Y^1$ and $Y^2$ are independently O or S,
n1 and n2 are independently an integer of 0 or 1,
$R^1$ to $R^3$ are independently hydrogen, deuterium, a phenyl group, a biphenyl group, or a naphthyl group, and
$R^4$ to $R^8$ are independently hydrogen or deuterium.

3. The compound for an organic optoelectronic device of claim 1, wherein the compound is represented by Chemical Formula 1A, Chemical Formula 1B, or Chemical Formula 1C:

[Chemical Formula 1A]

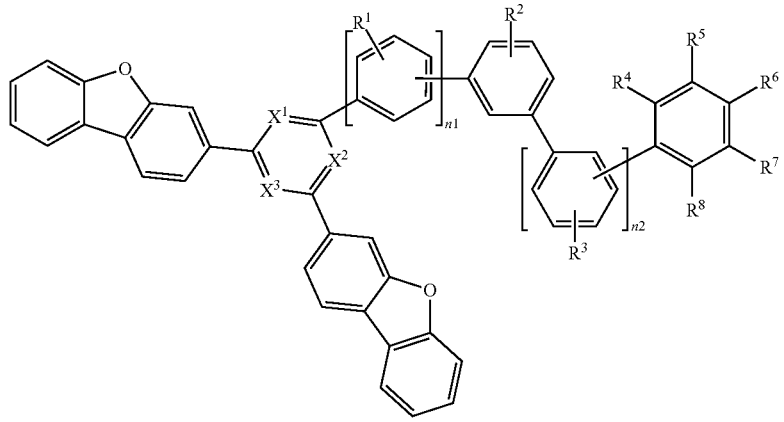

-continued

[Chemical Formula 1B]

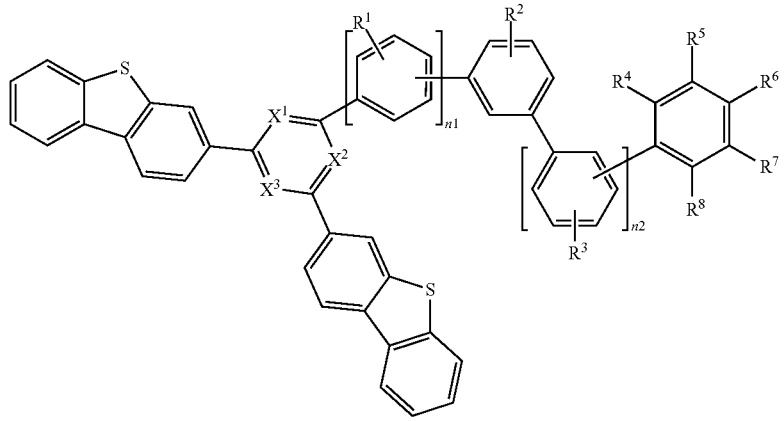

[Chemical Formula 1C]

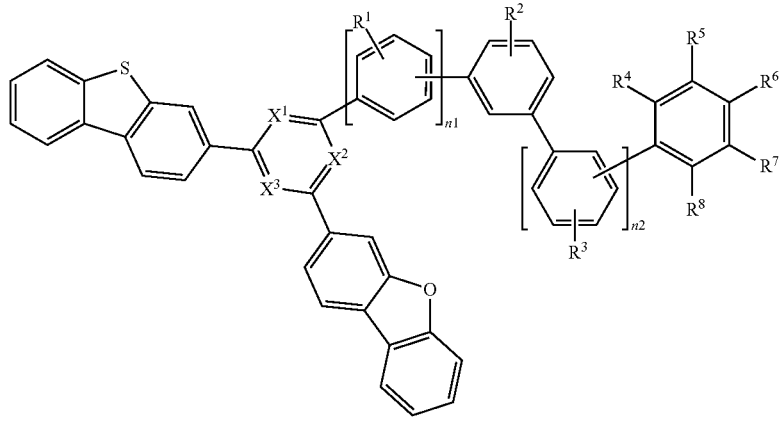

wherein, in Chemical Formula 1A, Chemical Formula 1B, and Chemical Formula 1C,
$X^1$ to $X^3$ are independently N or CH,
at least two of $X^1$ to $X^3$ are N,
n1 and n2 are independently an integer of 0 or 1,
$R^1$ to $R^3$ are independently hydrogen, deuterium, a phenyl group, a biphenyl group, or a naphthyl group, and
$R^4$ to $R^8$ are independently hydrogen or deuterium.

4. The compound for an organic optoelectronic device of claim 1, wherein the compound is represented by Chemical Formula 1-1 or 1-2:

[Chemical Formula 1-1]

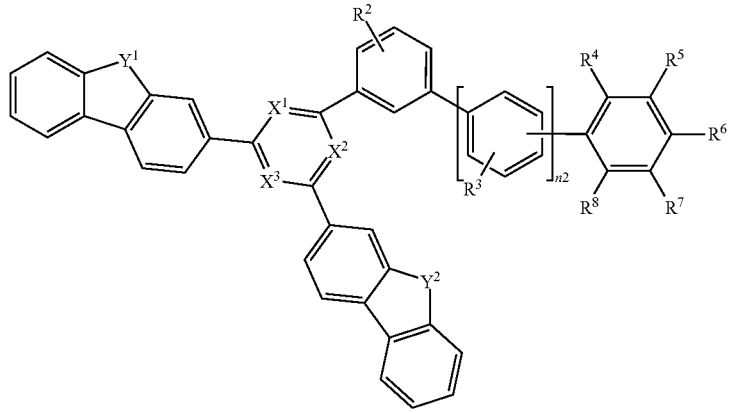

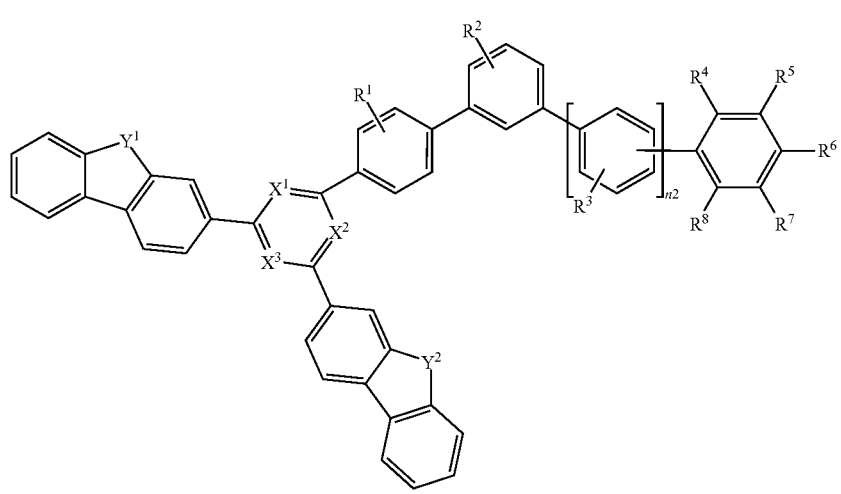

[Chemical Formula 1-2]

wherein, in Chemical Formulae 1-1 to 1-2,
$X^1$ to $X^3$ are independently N or CH,
at least two of $X^1$ to $X^3$ are N,
$Y^1$ and $Y^2$ are independently O or S,
n2 is an integer of 0 or 1,
$R^1$ to $R^3$ are independently hydrogen, deuterium, a phenyl group, a biphenyl group, or a naphthyl group, and
$R^4$ to $R^8$ are independently hydrogen or deuterium.

5. The compound for an organic optoelectronic device of claim 1, wherein the compound is selected from compounds of Group 1:

[Group 1]

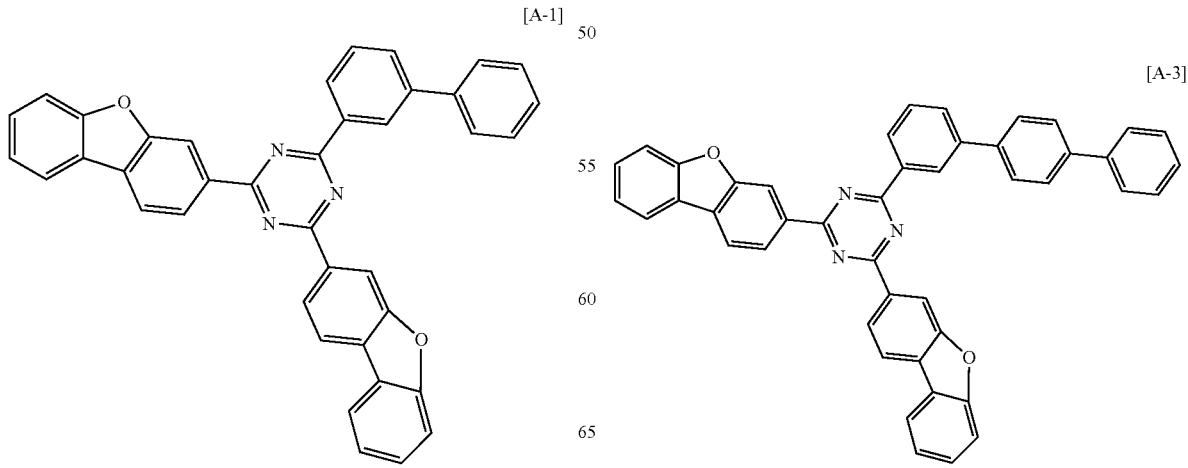

[A-1]

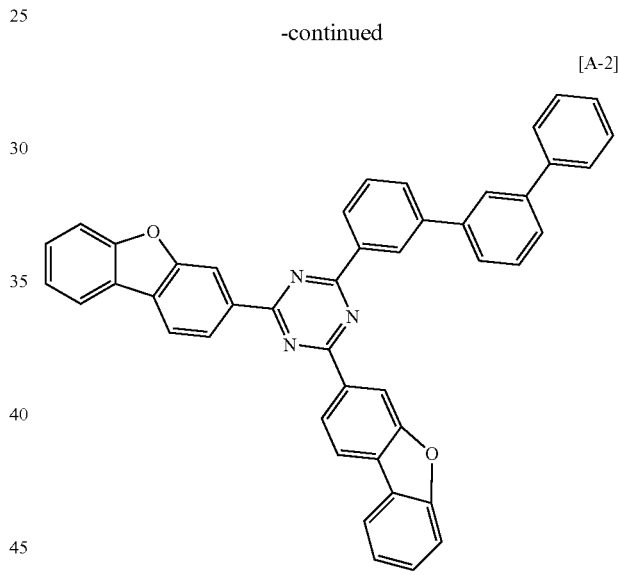

[A-2]

[A-3]

-continued
[A-4]
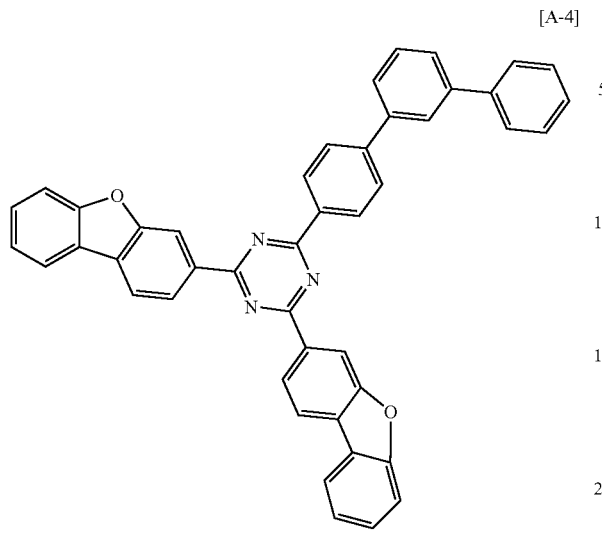
[A-5]
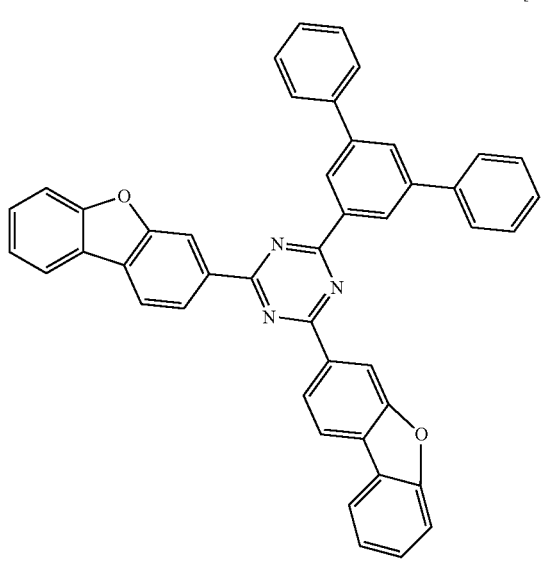
[A-6]
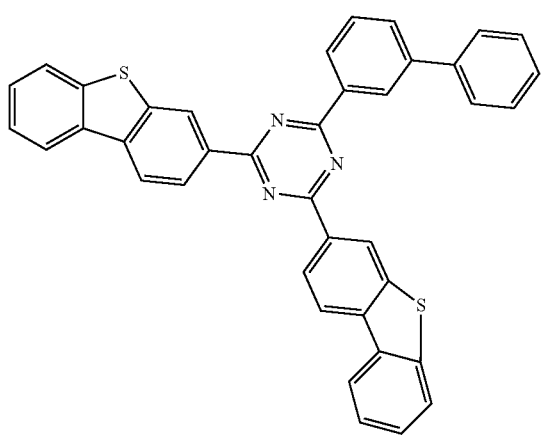
-continued
[A-7]
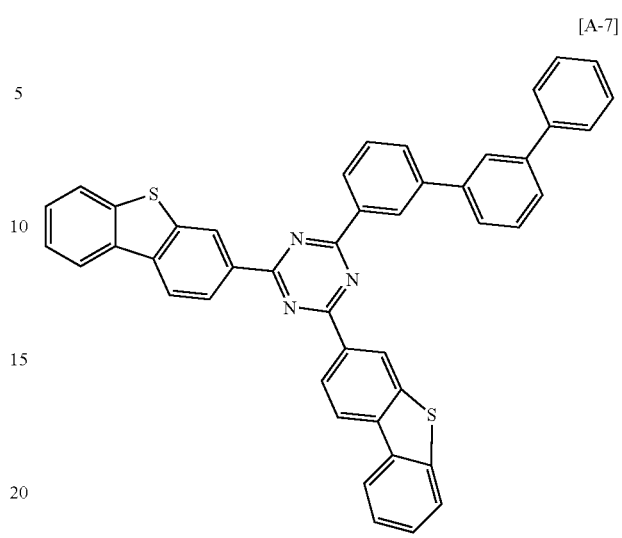
[A-8]
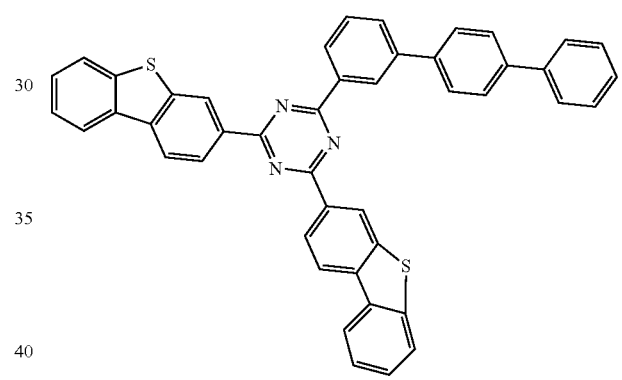
[A-9]
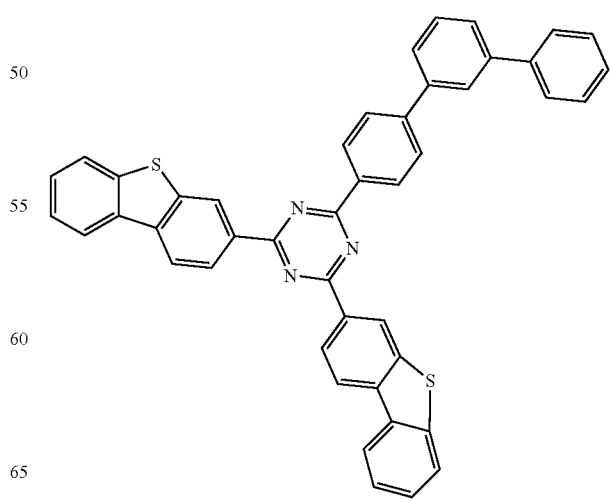

[A-10]
[A-11]
[A-12]
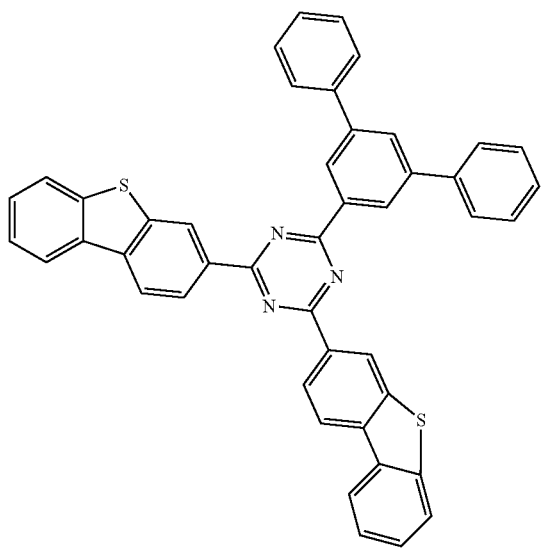
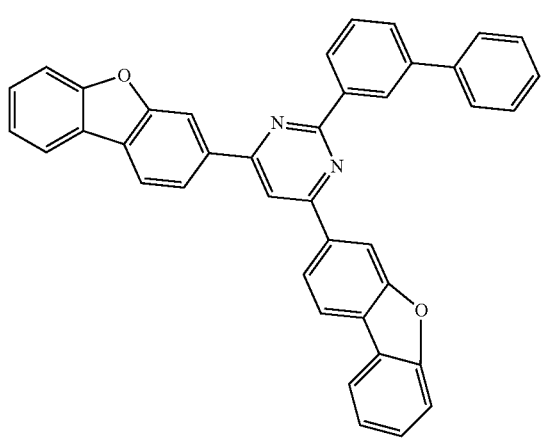
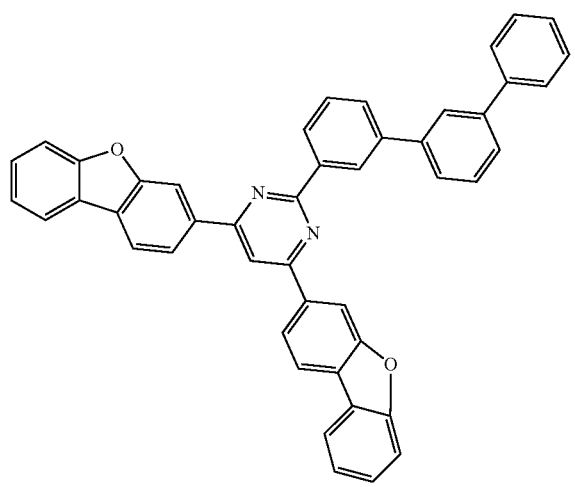
[A-13]
[A-14]
[A-15]
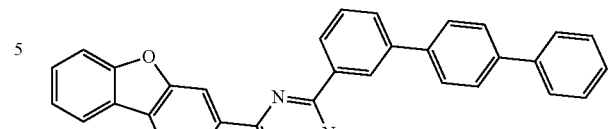
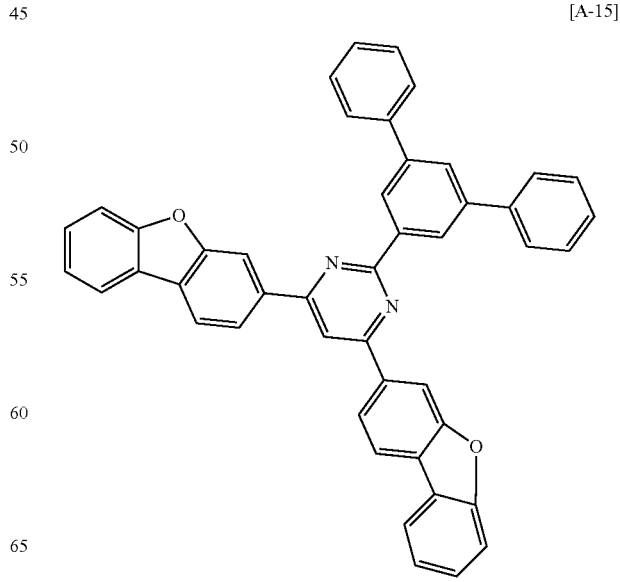

[A-16]
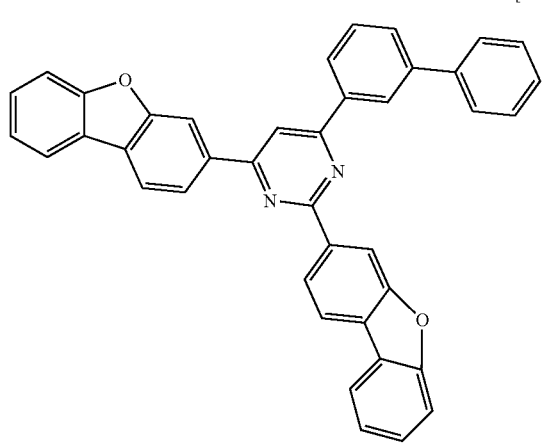
[A-17]
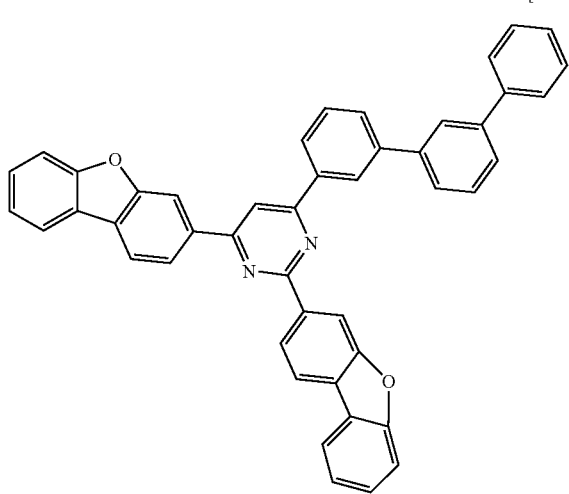
[A-18]
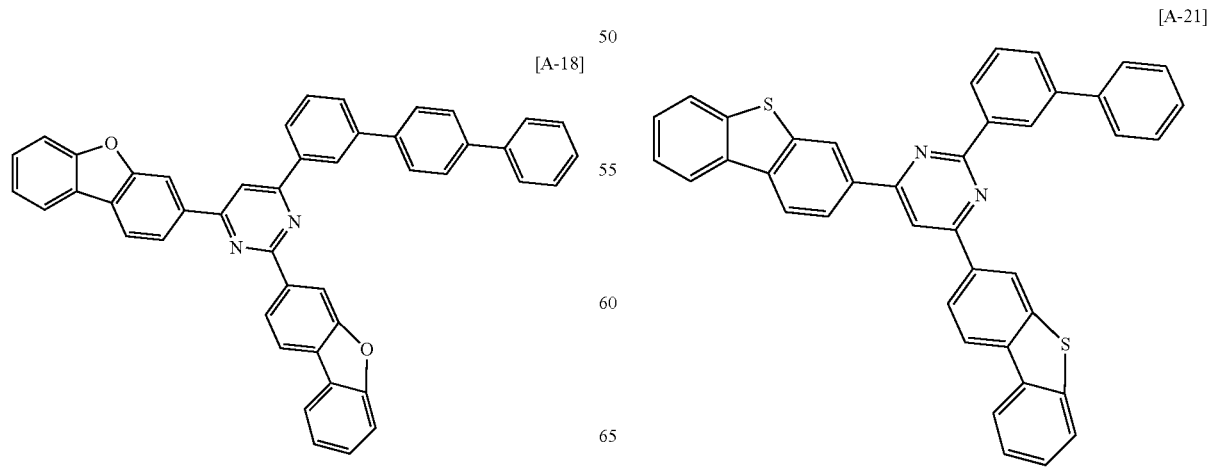
[A-19]
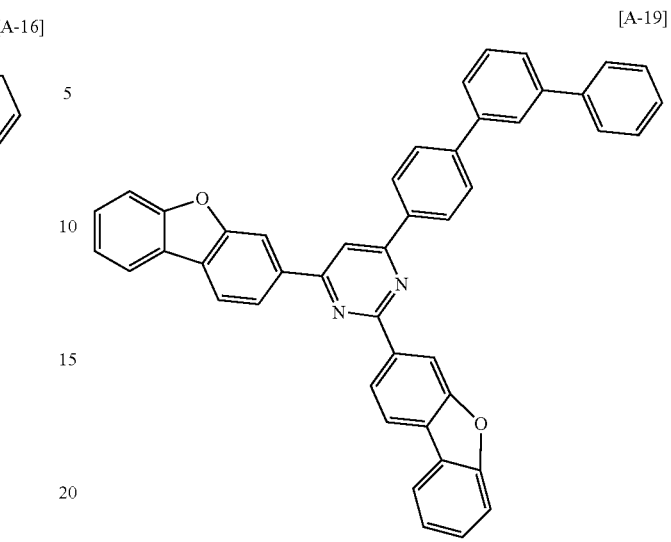
[A-20]
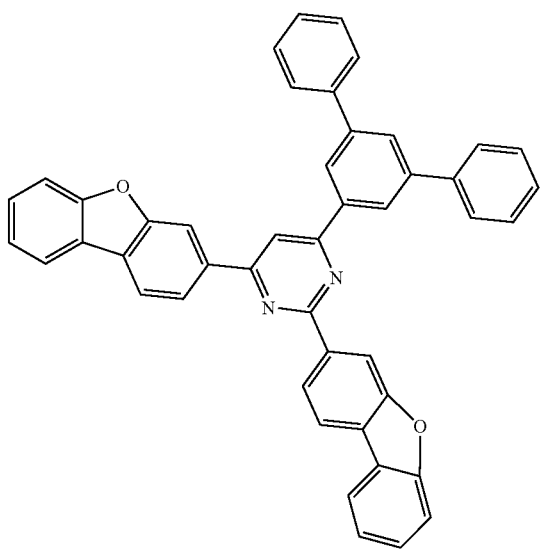
[A-21]

-continued
[A-22]
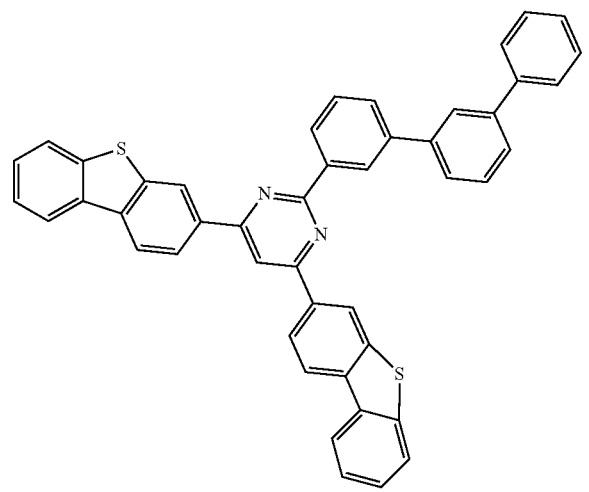
[A-23]
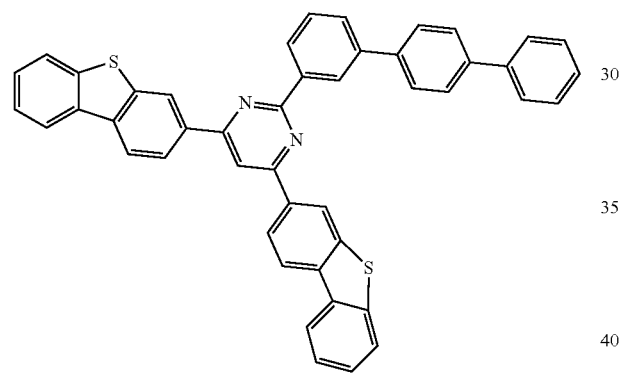
[A-24]
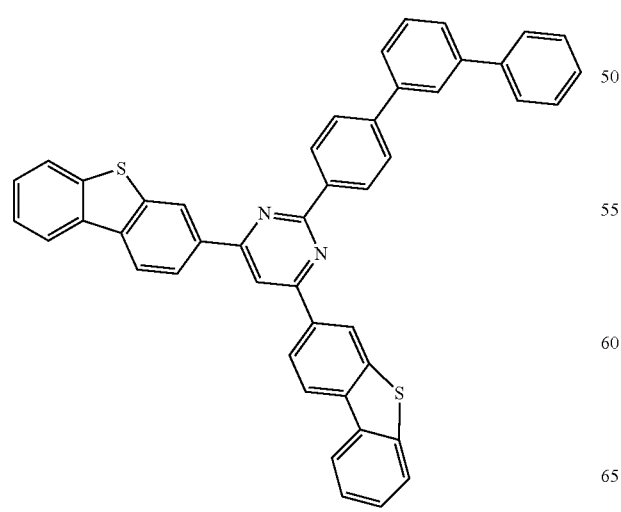
[A-25]
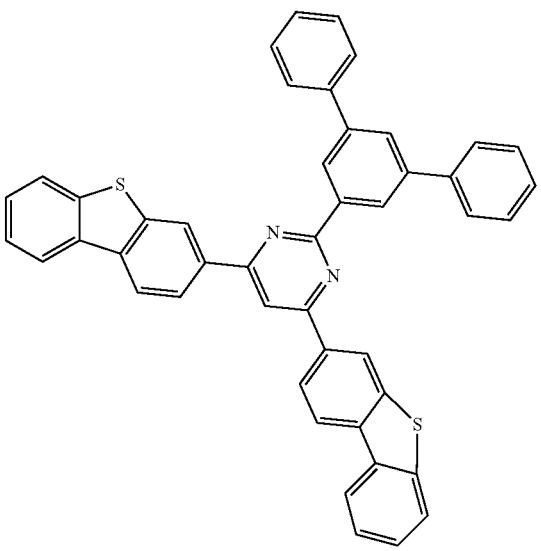
[A-26]
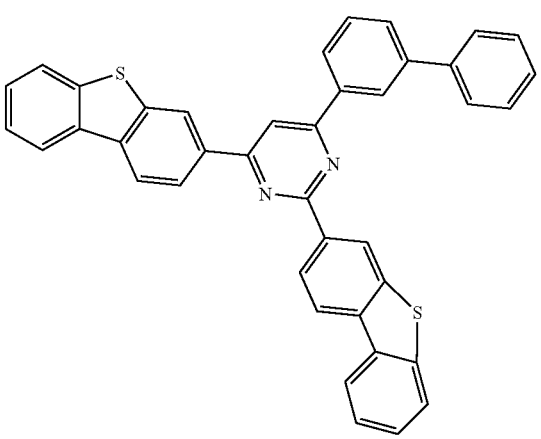
[A-27]
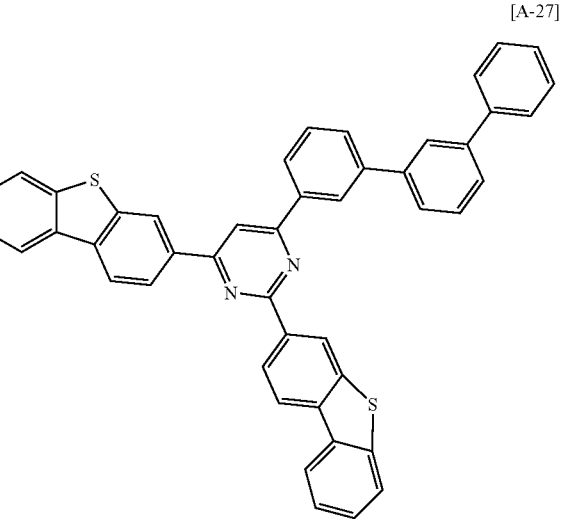

-continued

[A-28]
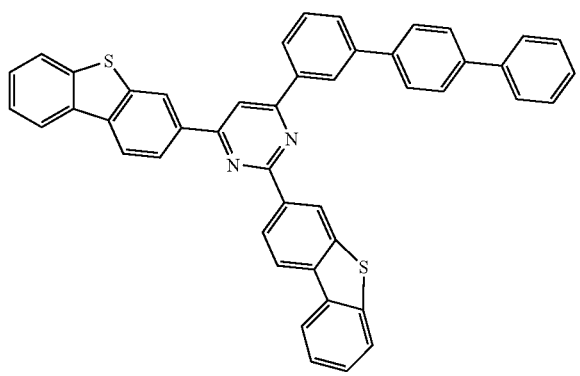

[A-29]
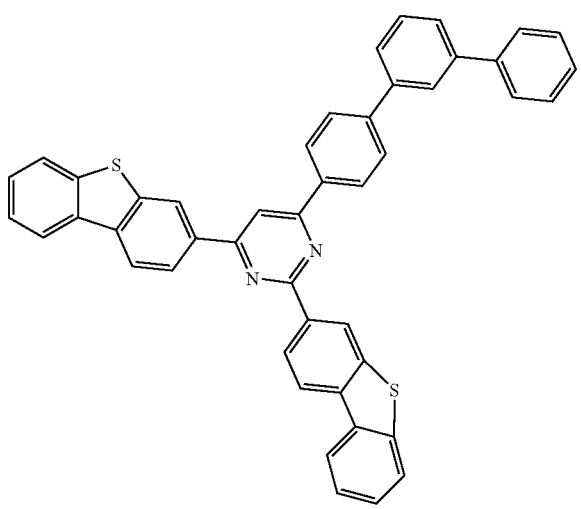

[A-30]
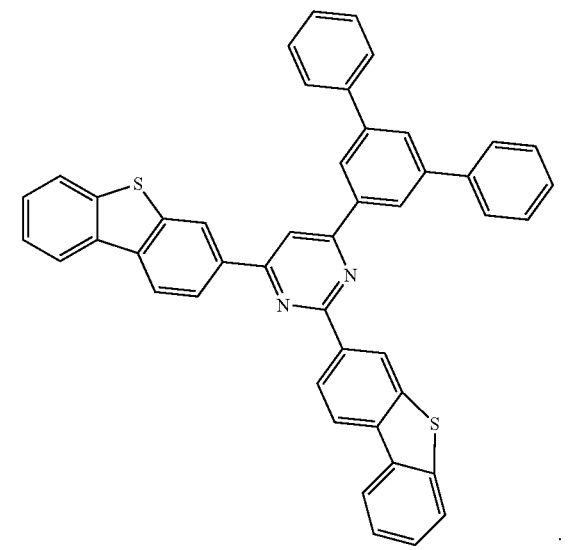

6. A composition for an organic optoelectronic device, comprising the compound for an organic optoelectronic device of claim 1; and a second compound for an organic optoelectronic device represented by Chemical Formula 2:

[Chemical Formula 2]

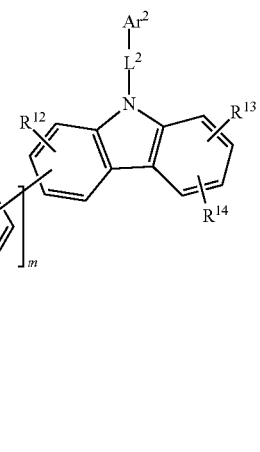

wherein, in Chemical Formula 2, $L^1$ and $L^2$ are independently a single bond, a substituted or unsubstituted C6 to C30 arylene group, a substituted or unsubstituted C2 to C30 heteroarylene group, or a combination thereof, $Ar^1$ and $Ar^2$ are independently a substituted or unsubstituted C6 to C30 aryl group, a substituted or unsubstituted C2 to C30 heterocyclic group, or a combination thereof, $R^9$ to $R^{14}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is an integer of 0 to 2;

wherein the "substituted" refers to replacement of at least one hydrogen by deuterium, a C1 to C4 alkyl group, a C6 to C18 aryl group, or a C2 to C30 heteroaryl group.

7. The composition for an organic optoelectronic device of claim 6, wherein $Ar^1$ and $Ar^2$ of Chemical Formula 2 are independently, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

8. The composition for an organic optoelectronic device of claim 6, wherein:
Chemical Formula 2 includes one of structures of Group II, and
*-L$^1$-Ar$^1$ and *-L$^2$-Ar$^2$ of Chemical Formula 2 are one of substituents of Group III:
[Group II]
C-1
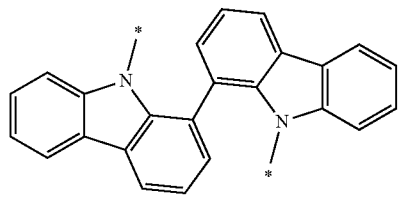
C-2
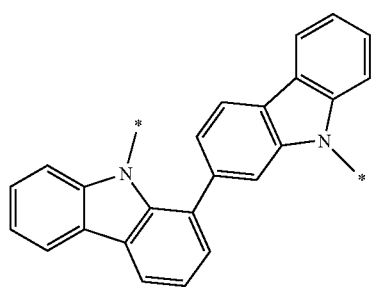
C-3
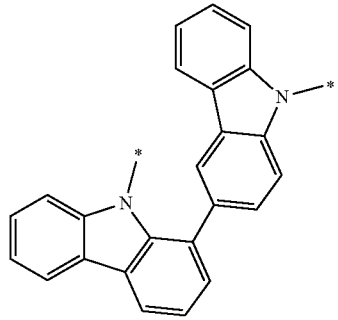
C-4
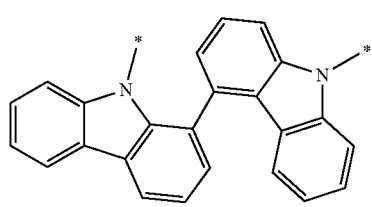
C-5
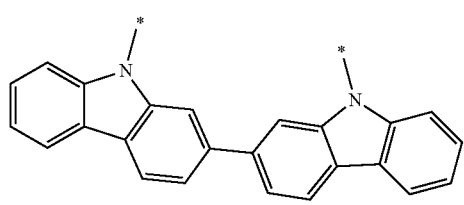
-continued
C-6
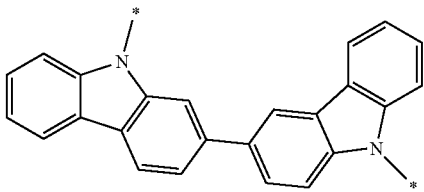
C-7
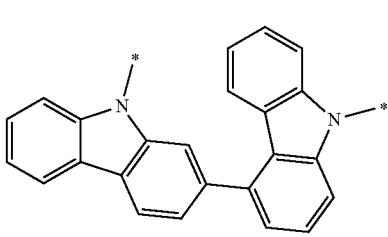
C-8
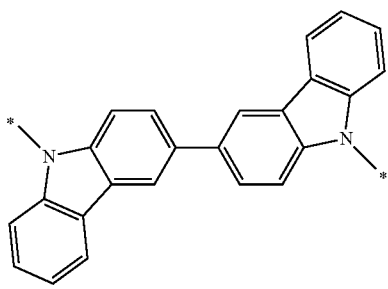
C-9
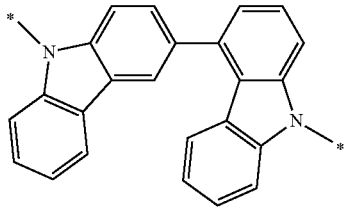
C-10
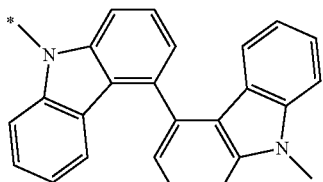
C-11
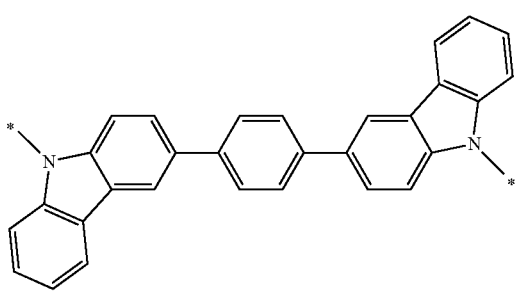

C-12
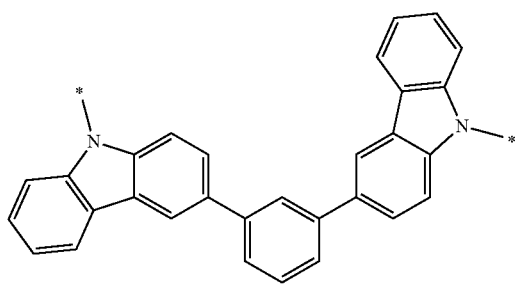
C-13
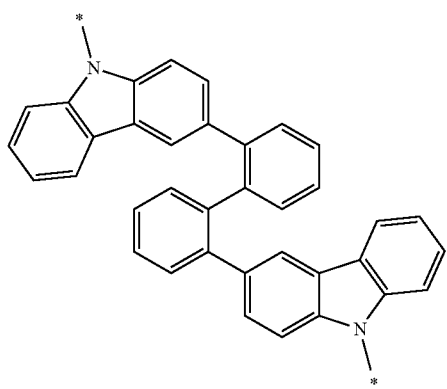
C-14
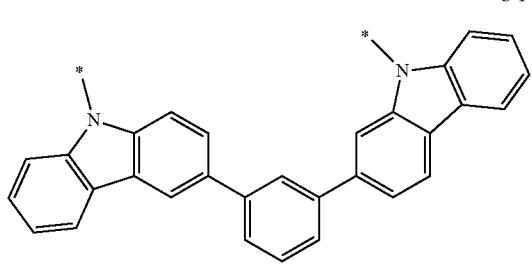
C-15
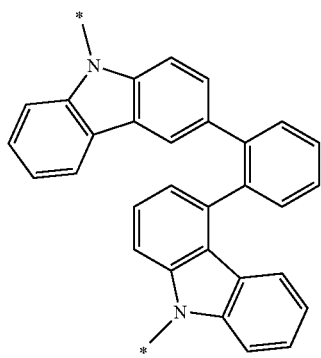
C-16
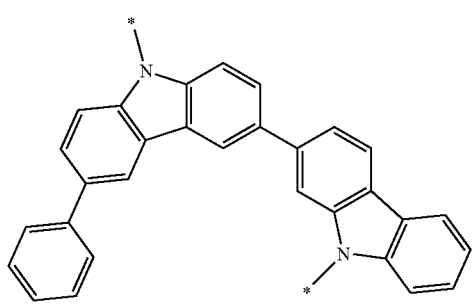
C-17
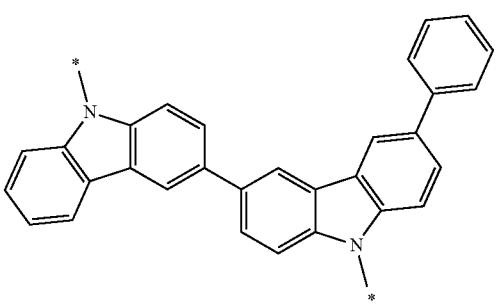
C-18
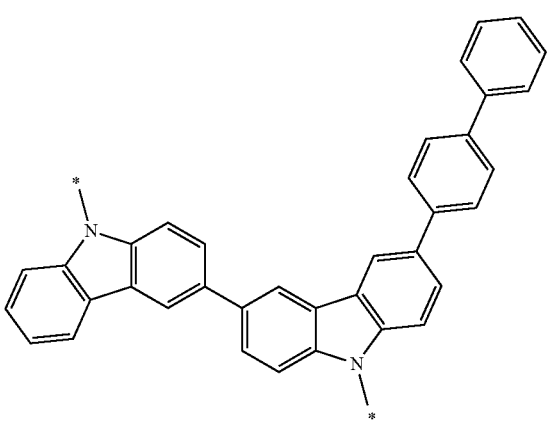
[Group III]
B-1
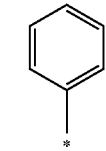
B-2
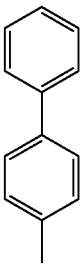
B-3
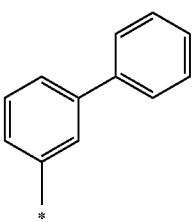

-continued
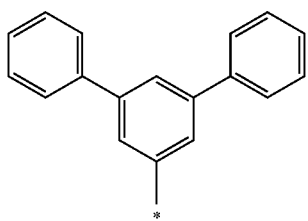
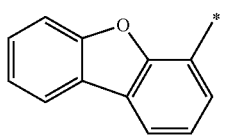
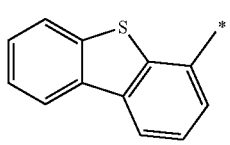
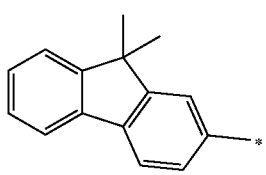
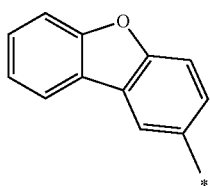
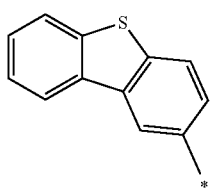
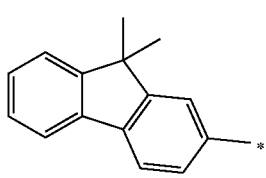
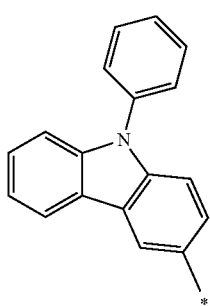
-continued
B-4
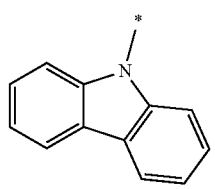
B-5
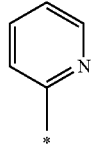
B-6
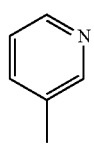
B-7
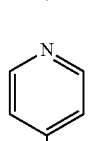
B-8
B-9
B-10
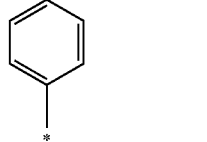
B-11
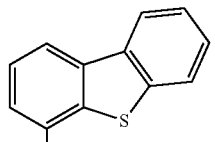
B-12
B-13
B-14
B-15
B-16
B-17
B-18
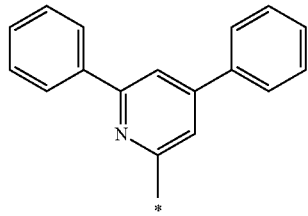

B-19

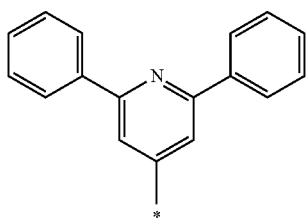

B-20

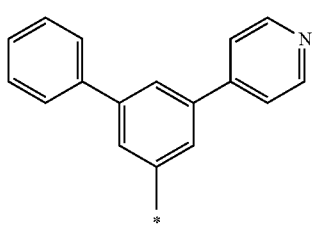

B-21

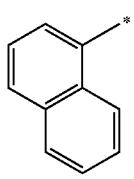

B-22

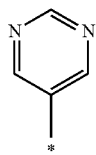

B-23

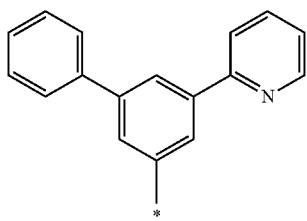

B-24

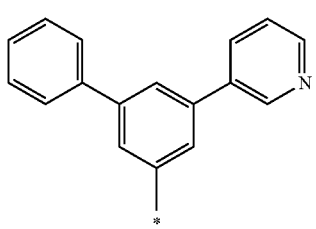

B-25

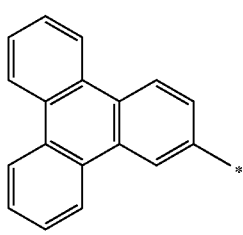

B-26

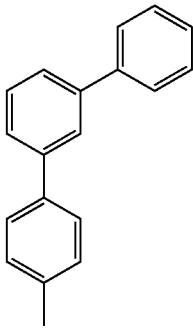

B-27

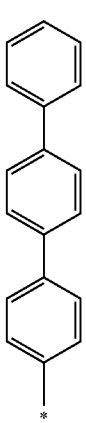

B-28

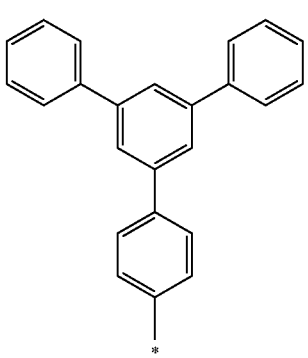

wherein, in Groups II and III, * is a linking point.

9. The composition for an organic optoelectronic device of claim 8, wherein:

Chemical Formula 2 includes structure C-8 or structure C-17 of Group II, and

*-L¹-Ar¹ and *-L²-Ar² of Chemical Formula 2 are selected from substituents B-1, B-2, B-3, and B-16 of Group III.

10. An organic optoelectronic device, comprising
an anode and a cathode facing each other, and
at least one organic layer disposed between the anode and the cathode,
wherein the organic layer includes the compound for an organic optoelectronic device of claim 1.

11. The organic optoelectronic device of claim 10, wherein the organic layer includes a light-emitting layer, and
the light-emitting layer includes the compound for an organic optoelectronic device.

12. The organic optoelectronic device of claim 11, wherein the compound for an organic optoelectronic device is included as a host of the light-emitting layer.

13. The organic optoelectronic device of claim 11, wherein the organic layer further includes at least one auxiliary layer selected from a hole injection layer, a hole transport layer, an electron blocking layer, an electron transport layer, an electron injection layer, and a hole blocking layer, the auxiliary layer further includes an electron transport auxiliary layer that is adjacent to the light-emitting layer, and the electron transport auxiliary layer includes the compound for an organic optoelectronic device.

14. A display device comprising the organic optoelectronic device of claim 10.

15. An organic optoelectronic device, comprising
an anode and a cathode facing each other, and
at least one organic layer disposed between the anode and the cathode,
wherein the organic layer includes the composition for an organic optoelectronic device of claim 6.

16. A display device comprising the organic optoelectronic device of claim 15.

* * * * *